(12) United States Patent
Moore et al.

(10) Patent No.: US 9,980,982 B2
(45) Date of Patent: May 29, 2018

(54) HE4 BASED THERAPY FOR MALIGNANT DISEASE

(75) Inventors: Richard G. Moore, Cranston, RI (US); Rakesh K. Singh, Barrington, RI (US)

(73) Assignee: Women & Infants Hospital of Rhode Island, Providence, RI (US)

( * ) Notice: Subject to any disclaimer, the term of this patent is extended or adjusted under 35 U.S.C. 154(b) by 141 days.

(21) Appl. No.: 14/124,595

(22) PCT Filed: Jun. 6, 2012

(86) PCT No.: PCT/US2012/041080
§ 371 (c)(1),
(2), (4) Date: Aug. 11, 2014

(87) PCT Pub. No.: WO2012/170513
PCT Pub. Date: Dec. 13, 2012

(65) Prior Publication Data
US 2014/0348854 A1 Nov. 27, 2014

Related U.S. Application Data

(60) Provisional application No. 61/541,663, filed on Sep. 30, 2011, provisional application No. 61/493,881, filed on Jun. 6, 2011.

(51) Int. Cl.
| | | |
|---|---|---|
| *C07K 14/47* | (2006.01) | |
| *A61K 31/4745* | (2006.01) | |
| *A61K 31/568* | (2006.01) | |
| *G01N 33/574* | (2006.01) | |
| *C07K 16/18* | (2006.01) | |
| *C12N 15/113* | (2010.01) | |
| *A61K 31/7105* | (2006.01) | |
| *A61K 31/713* | (2006.01) | |
| *A61K 31/592* | (2006.01) | |
| *A61K 38/17* | (2006.01) | |
| *A61K 39/00* | (2006.01) | |
| *A61K 31/337* | (2006.01) | |
| *A61K 45/06* | (2006.01) | |
| *A61K 33/24* | (2006.01) | |
| *A61K 31/704* | (2006.01) | |

(52) U.S. Cl.
CPC .......... *A61K 33/24* (2013.01); *A61K 31/337* (2013.01); *A61K 31/4745* (2013.01); *A61K 31/568* (2013.01); *A61K 31/592* (2013.01); *A61K 31/704* (2013.01); *A61K 31/713* (2013.01); *A61K 31/7105* (2013.01); *A61K 38/17* (2013.01); *A61K 45/06* (2013.01); *C07K 14/47* (2013.01); *C07K 16/18* (2013.01); *C12N 15/113* (2013.01); *G01N 33/57484* (2013.01); *G01N 33/57496* (2013.01); *A61K 2039/505* (2013.01); *G01N 2333/811* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,552,390 A | 9/1996 | Scholar et al. | |
| 5,674,872 A * | 10/1997 | Johnson | A61K 31/4745 514/233.2 |
| 2005/0095592 A1* | 5/2005 | Jazaeri | C12Q 1/6886 435/6.16 |
| 2007/0286865 A1 | 12/2007 | Moore et al. | |
| 2008/0020473 A1 | 1/2008 | Moore et al. | |
| 2008/0254048 A1* | 10/2008 | Cheek | C07K 16/3069 424/184.1 |
| 2009/0192101 A1* | 7/2009 | Hung | A61K 48/0058 514/44 R |
| 2009/0221529 A1 | 9/2009 | Brard et al. | |
| 2010/0144687 A1 | 6/2010 | Glaser | |
| 2011/0038883 A1 | 2/2011 | Cheek et al. | |
| 2011/0104120 A1 | 5/2011 | Xiao et al. | |

FOREIGN PATENT DOCUMENTS

| | | |
|---|---|---|
| CN | 1813188 A | 8/2006 |
| CN | 1823995 A | 8/2006 |
| CN | 101480399 A | 7/2009 |
| WO | WO-0116354 A1 | 3/2001 |
| WO | WO-03021273 A2 | 3/2003 |
| WO | WO-07081767 A2 | 7/2007 |
| WO | WO-07081768 A2 | 7/2007 |
| WO | WO-2008030979 A2 | 3/2008 |
| WO | WO-2010061393 A1 | 6/2010 |

OTHER PUBLICATIONS

Curly et al. (Frontiers in Bioscience Jan. 1, 2011, 16: 368-392).*
Muggia, F. (Gynecologic Oncology 2009 112: 275-281).*
Gura (Science, 1997, 278:1041-1042).*
Kaiser (Science, 2006, 313: 1370).*
Gerdes et al. (Front. Oncol. Dec. 18, 2014 doi: 10.3389/fonc.2014.00366, pp. 1-12).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Tan et al. (Ovarian Cancer: Can We Reverse Drug Resistance? In: Ovarian Cancer: State of the Art and Future Directions in Translational Research, Coukos et al. eds., Springer New York, NY, 2008, pp. 153-167).*
Thibodeaux and Curiel (International Rev. Immunology 2011, 30-102-119).*
Wang et al. (Expert Opinion Biol. Ther. 2009 9(1)): 1357-1368).*
American Cancer Society (Ovarian Cancer 2014, pp. 1-63).*

(Continued)

*Primary Examiner* — Peter J Reddig
(74) *Attorney, Agent, or Firm* — Saul Ewing Arnstein & Lehr LLP; Peter C. Lauro, Esq.

(57) ABSTRACT

The invention provides compositions and methods for utilizing human epididymal secretion protein E4 (HE4) in the prevention and treatment of cancer and other human diseases.

28 Claims, 31 Drawing Sheets

(56) References Cited

OTHER PUBLICATIONS

Bignotti et al. "Diagnostic and Prognostic Impact of Serum HE4 Detection in Endometrial Carcinoma Patients." *Br. J. Cancer.* 104.9(2011):1418-1425.
Bilsland et al. "Selective Ablation of Human Cancer Cells by Telomerase-Specific Adenoviral Suicide Gene Therapy Vectors Expressing Bacterial Nitroreductase." *Oncogene.* 22.3(2003):370-380.
Broggini et al. "Cell Cycle-Related Phosphatases CDC25A and B Expression Correlates With Survival in Ovarian Cancer Patients." *Anticancer Res.* 20(2000):4835-4840.
Clauss et al. "A Locus on Human Chromosome 20 Contains Several Genes Expressing Protease Inhibitor Domains with Homology to Whey Acidic Protein." *Biochem. J.* 368(2002):233-242.
Clauss et al. "Overexpression of Elafin in Ovarian Carcinoma is Driven by Genomic Gains and Activation of the Nuclear Factor κB Pathway and is Associated with Poor Overall Survival." *Neoplasia.* 12.2(2010):161-172.
Cong et al. "The Human Telomerase Catalytic Subunit hTERT: Organization of the Gene and Characterization of the Promoter." *Hum. Mol. Genet.* 8.1(1999):137-142.
D'Andrilli et al. "Cell Cycle Genes in Ovarian Cancer: Steps Toward Earlier Diagnosis and Novel Therapies." *Clin. Cancer Res.* 10.24(2004):8132-8141.
Garver et al. "Strategy for Achieving Selective Killing of Carcinomas." *Gene Ther.* 1.1(1994):46-50.
Gilks et al. "Distinction Between Serous Tumors of Low Malignant Potential and Serous Carcinomas Based on Global mRNA Expression Profiling." *Gynecol. Oncol.* 96.3(2005):684-694.
Hartwell et al. "Cell Cycle Control and Cancer." *Science.* 266.5192(1994):1821-1828.
Hiyama et al. "Clinical Utility of Telomerase in Cancer." *Oncogene.* 21.4(2002):643-649.
Hough et al. "Large-Scale Serial Analysis of Gene Expression Reveals Genes Differentially Expressed in Ovarian Cancer." *Cancer Res.* 60.22(2000):6281-6287.
Kern. "Heterogeneity of Drug Resistance in Human Breast and Ovarian Cancers." *Cancer J. Sci. Am.* 4.1(1998):41-45.
Kirchhoff et al. "A Major Human Epididymis-Specific cDNA Encodes a Protein with Sequence Homology to Extracellular Proteinase Inhibitors." *Biol. Reprod.* 45.2(1991):350-357.
Kristjánsdóttir et al. "Cdc25 Phosphatases and Cancer." *Chem. Biol.* 11.8(2004):1043-1051.
Lange et al. "Anti-Proliferative and Pro-Apoptotic Properties of 3-Bromoacetoxy Calcidiol in High-Risk Neuroblastoma." *Chem. Biol. Drug Des.* 70.4(2007):302-310.
Lange et al. "Iron(III)-Salophene: An Organometallic Compound with Selective Cytotoxic and Anti-Proliferative Properties in Platinum-Resistant Ovarian Cancer Cells." *PLoS One.* 3.5(2008):e2303.
Lidor et al. "In Vitro Expression of the Diphtheria Toxin A-Chain Gene Under the Control of Human Chorionic Gonadotropin Gene Promoters as a Means of Directing Toxicity to Ovarian Cancer Cell Lines." *Am. J. Obstet. Gynecol.* 177.3(1997):579-585.
Moore et al. "A Novel Multiple Marker Bioassay Utilizing HE4 and CA125 for the Prediction of Ovarian Cancer in Patients with a Pelvic Mass." *Gynecol. Oncol.* 112.1(2009):40-46.
Moore et al. "Utility of a Novel Serum Tumor Biomarker HE4 in Patients with Endometrioid Adenocarcinoma of the Uterus." *Gynecol. Oncol.* 110.2(2008):196-201.
Parker et al. "A Prospective Blinded Study of the Predictive Value of an Extreme Drug Resistance Assay in Patients Receiving CPT-11 for Recurrent Glioma." *J. Neurooncol.* 66.3(2004):365-375.
Robertson et al. "Use of a Tissue-Specific Promoter for Targeted Expression of the Herpes Simplex Virus Thymidine Kinase Gene in Cervical Carcinoma Cells." *Cancer Gene Ther.* 5.5(1998):331-336.
Singh et al. "Isothiocyanate NB7M Causes Selective Cytotoxicity, Pro-Apoptotic Signalling and Cell-Cycle Regression in Ovarian Cancer Cells." *Br. J. Cancer.* 99.11(2008):1823-1831.
Tanyi et al. "Identification of Tissue- and Cancer-Selective Promoters for the Introduction of Genes into Human Ovarian Cancer Cells." *Gynecol. Oncol.* 85.3(2002):451-458.
Wang et al. "Monitoring Gene Expression Profile Changes in Ovarian Carcinomas Using cDNA Microarray." *Gene.* 229.1-2(1999):101-108.
Yano et al. "High Ambient Glucose Induces Angiotensin-Independent AT-1 Receptor Activation, Leading to Increases in Proliferation and Extracellular Matrix Accumulation in MES-13 Mesangial Cells." *Biochem. J.* 423.1(2009):129-143.
Drapkin et al. "Human Epididymis Protein 4 (HE4) is a Secreted Glycoprotein that is Overexpressed by Serous and Endometrioid Ovarian Carcinomas." *Cancer Res.* 65.6(2005):2162-2169.
Gocek et al. "Vitamin D and Differentiation in Cancer." *Crit. Rev. Clin. Lab. Sci.* 46.4(2009):190-209.
Huang et al. "Nanoparticle-Delivered Suicide Gene Therapy Effectively Reduces Ovarian Tumor Burden in Mice." *Cancer Res.* 69.15(2009):6184-6191.
Braicu et al., Preoperative HE4 expression in plasma predicts surgical outcome in primary ovarian cancer patients: results from the OVCAD study. Gynecol Oncol. Feb. 2013;128(2):245-51.
GenBank Accession No. X63187.1.
Moore et al.,The use of multiple novel tumor biomarkers for the detection of ovarian carcinoma in patients with a pelvic mass. Gynecol Oncol. Feb. 2008;108(2):402-8.

* cited by examiner

MT19c:R=Me
PT19c:R=ph
X=Br, Cl, F, I or R
R= H, alkyl, aryl, heteroaryl
or derivatives thereof

*Pairwise group differences (Turkey-adjusted p values)
Clone vs WT p=0.007; Clone vs null vector p<0.0001
WT vs Null vector p=0.3 (not significant)

| SKOV-3 (wt) | | Empty Vector | | HE4+ clone-1 | |
|---|---|---|---|---|---|
| Vehicle* | Treatment* | Vehicle* | Treatment* | Vehicle* | Treatment* |
| <15 | 15.73 | <15 | <15 | 286.08 | 413.94 |
| 26.41 | 54.67 | <15 | <15 | 144.08 | 142.08 |
| <15 | <15 | <15 | <15 | 409.06 | 386.48 |
| <15 | <15 | <15 | <15 | 422.26 | 422.07 |
| <15 | <15 | <15 | <15 | 327 | 145.81 |
| <15 | <15 | <15 | <15 | 144 | <15 |
| <15 | <15 | <15 | <15 | 225 | 309.9 |

* pM units of HE4

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Synthesized nucleotide oligo
<220> FEATURE:
<221> NAME/KEY: misc_feature
<222> LOCATION: (1)..(20)
<223> OTHER INFORMATION: each nucleotide is connected via a
      phosphorothioate internucleotide linkage

<400> SEQUENCE: 1
gacaccttcc cacagccatt                                              20

<210> SEQ ID NO 2
<211> LENGTH: 21
<212> TYPE: DNA
<213> ORGANISM: Artificial Sequence
<220> FEATURE:
<223> OTHER INFORMATION: Synthesized nucleotide oligo
<220> FEATURE:
<221> NAME/KEY: misc_feature
<222> LOCATION: (1)..(21)
<223> OTHER INFORMATION: each nucleotide is connected via a
      phosphorothioate internucleotide linkage

<400> SEQUENCE: 2
gacaccttcc cacagccatt g                                            21

<210> SEQ ID NO 3
<211> LENGTH: 19
<212> TYPE: DNA
<213> ORGANISM: Artificial Sequence
<220> FEATURE:
<223> OTHER INFORMATION: Synthesized nucleotide oligo
<220> FEATURE:
<221> NAME/KEY: misc_feature
<222> LOCATION: (1)..(19)
<223> OTHER INFORMATION: each nucleotide is connected via a
      phosphorothioate internucleotide linkage

<400> SEQUENCE: 3
gacaccttcc cacagccat                                               19

<210> SEQ ID NO 4
<211> LENGTH: 20
<212> TYPE: DNA
<213> ORGANISM: Artificial Sequence
<220> FEATURE:
<223> OTHER INFORMATION: Synthesized nucleotide oligo
<220> FEATURE:
<221> NAME/KEY: misc_feature
<222> LOCATION: (1)..(20)
<223> OTHER INFORMATION: each nucleotide is connected via a
      phosphorothioate internucleotide linkage

<400> SEQUENCE: 4
acaccttccc acagccattg                                              20

<210> SEQ ID NO 5
<211> LENGTH: 19
<212> TYPE: DNA

```
<213> ORGANISM: Artificial Sequence
<220> FEATURE:
<223> OTHER INFORMATION: Synthesized nucleotide oligo
<220> FEATURE:
<221> NAME/KEY: misc_feature
<222> LOCATION: (1)..(19)
<223> OTHER INFORMATION: each nucleotide is connected via a
      phosphorothioate internucleotide linkage

<400> SEQUENCE: 5
acaccttccc acagccatt                                                    19

<210> SEQ ID NO 6
<211> LENGTH: 124
<212> TYPE: PRT
<213> ORGANISM: Homo sapiens

<400> SEQUENCE: 6

Met Pro Ala Cys Arg Leu Gly Pro Leu Ala Ala Ala Leu Leu Leu Ser
1               5                   10                  15

Leu Leu Leu Phe Gly Phe Thr Leu Val Ser Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
    50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
            100                 105                 110

Gly Cys Gly Lys Val Ser Cys Val Thr Pro Asn Phe
        115                 120

<210> SEQ ID NO 7
<211> LENGTH: 22
<212> TYPE: PRT
<213> ORGANISM: Homo sapiens

<400> SEQUENCE: 7

Leu Gln Val Gln Val Asn Leu Pro Val Ser Pro Leu Pro Thr Tyr Pro
1               5                   10                  15

Tyr Ser Phe Phe Tyr Pro
            20

<210> SEQ ID NO 8
<211> LENGTH: 10
<212> TYPE: PRT
<213> ORGANISM: Homo sapiens

<400> SEQUENCE: 8

Leu Leu Cys Pro Asn Gly Gln Leu Ala Glu
1               5                   10

<210> SEQ ID NO 9
<211> LENGTH: 28
<212> TYPE: PRT
<213> ORGANISM: Homo sapiens

<400> SEQUENCE: 9

Ala Leu Phe His Trp His Leu Lys Thr Arg Arg Leu Trp Glu Ile Ser
```

```
                1               5                  10                 15
Gly Pro Arg Pro Arg Pro Thr Trp Asp Ser Ser
            20                  25
```

<210> SEQ ID NO 10
<211> LENGTH: 73
<212> TYPE: PRT
<213> ORGANISM: Homo sapiens

<400> SEQUENCE: 10

```
Met Leu Gln Val Gln Val Asn Leu Pro Val Ser Pro Leu Pro Thr Tyr
1               5                   10                  15

Pro Tyr Ser Phe Phe Tyr Pro Asp Lys Glu Gly Ser Cys Pro Gln Val
            20                  25                  30

Asn Ile Asn Phe Pro Gln Leu Gly Leu Cys Arg Asp Gln Cys Gln Val
        35                  40                  45

Asp Ser Gln Cys Pro Gly Gln Met Lys Cys Cys Arg Asn Gly Cys Gly
    50                  55                  60

Lys Val Ser Cys Val Thr Pro Asn Phe
65                  70
```

<210> SEQ ID NO 11
<211> LENGTH: 22
<212> TYPE: PRT
<213> ORGANISM: Homo sapiens

<400> SEQUENCE: 11

```
Pro Ala Cys Arg Leu Gly Pro Leu Ala Ala Ala Leu Leu Leu Ser Leu
1               5                   10                  15

Leu Leu Phe Gly Phe Thr
            20
```

<210> SEQ ID NO 12
<211> LENGTH: 9
<212> TYPE: PRT
<213> ORGANISM: Homo sapiens

<400> SEQUENCE: 12

```
Ser Leu Pro Asn Asp Lys Glu Gly Ser
1               5
```

<210> SEQ ID NO 13
<211> LENGTH: 28
<212> TYPE: PRT
<213> ORGANISM: Homo sapiens

<400> SEQUENCE: 13

```
Asp Lys Glu Gly Ser Cys Pro Gln Val Asn Ile Asn Phe Pro Gln Leu
1               5                   10                  15

Gly Leu Cys Arg Asp Gln Cys Gln Val Asp Ser Gln
            20                  25
```

<210> SEQ ID NO 14
<211> LENGTH: 60
<212> TYPE: PRT
<213> ORGANISM: Homo sapiens

<400> SEQUENCE: 14

```
Met Leu Gln Val Gln Val Asn Leu Pro Val Ser Pro Leu Pro Thr Tyr
1               5                   10                  15

Pro Tyr Ser Phe Phe Tyr Pro Asp Lys Glu Gly Ser Cys Pro Gln Val
```

```
            20                  25                  30
Asn Ile Asn Phe Pro Gln Leu Gly Leu Cys Arg Asp Gln Cys Gln Val
            35                  40                  45

Asp Ser Gln Cys Pro Gly Gln Met Lys Cys Cys Arg
        50                  55                  60

<210> SEQ ID NO 15
<211> LENGTH: 10
<212> TYPE: PRT
<213> ORGANISM: Homo sapiens

<400> SEQUENCE: 15

Met Pro Ala Cys Arg Leu Gly Pro Leu Ala
1               5                   10

<210> SEQ ID NO 16
<211> LENGTH: 10
<212> TYPE: PRT
<213> ORGANISM: Homo sapiens

<400> SEQUENCE: 16

Ala Ala Leu Leu Leu Ser Leu Leu Leu Phe
1               5                   10

<210> SEQ ID NO 17
<211> LENGTH: 10
<212> TYPE: PRT
<213> ORGANISM: Homo sapiens

<400> SEQUENCE: 17

Gly Phe Thr Leu Val Ser Gly Thr Gly Ala
1               5                   10

<210> SEQ ID NO 18
<211> LENGTH: 10
<212> TYPE: PRT
<213> ORGANISM: Homo sapiens

<400> SEQUENCE: 18

Glu Lys Thr Gly Val Cys Pro Glu Leu Gln
1               5                   10

<210> SEQ ID NO 19
<211> LENGTH: 10
<212> TYPE: PRT
<213> ORGANISM: Homo sapiens

<400> SEQUENCE: 19

Ala Asp Gln Asn Cys Thr Gln Glu Cys Val
1               5                   10

<210> SEQ ID NO 20
<211> LENGTH: 10
<212> TYPE: PRT
<213> ORGANISM: Homo sapiens

<400> SEQUENCE: 20

Ser Asp Ser Glu Cys Ala Asp Asn Leu Lys
1               5                   10

<210> SEQ ID NO 21
<211> LENGTH: 10
<212> TYPE: PRT
<213> ORGANISM: Homo sapiens
```

```
<400> SEQUENCE: 21

Cys Cys Ser Ala Gly Cys Ala Thr Phe Cys
1               5                   10

<210> SEQ ID NO 22
<211> LENGTH: 10
<212> TYPE: PRT
<213> ORGANISM: Homo sapiens

<400> SEQUENCE: 22

Ser Leu Pro Asn Asp Lys Glu Gly Ser Cys
1               5                   10

<210> SEQ ID NO 23
<211> LENGTH: 10
<212> TYPE: PRT
<213> ORGANISM: Homo sapiens

<400> SEQUENCE: 23

Pro Gln Val Asn Ile Asn Phe Pro Gln Leu
1               5                   10

<210> SEQ ID NO 24
<211> LENGTH: 10
<212> TYPE: PRT
<213> ORGANISM: Homo sapiens

<400> SEQUENCE: 24

Gly Leu Cys Arg Asp Gln Cys Gln Val Asp
1               5                   10

<210> SEQ ID NO 25
<211> LENGTH: 10
<212> TYPE: PRT
<213> ORGANISM: Homo sapiens

<400> SEQUENCE: 25

Ser Gln Cys Pro Gly Gln Met Lys Cys Cys
1               5                   10

<210> SEQ ID NO 26
<211> LENGTH: 10
<212> TYPE: PRT
<213> ORGANISM: Homo sapiens

<400> SEQUENCE: 26

Arg Asn Gly Cys Gly Lys Val Ser Cys Val
1               5                   10

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
aggagcagag aagactgg                                                  18

<210> SEQ ID NO 28
<211> LENGTH: 18
<212> TYPE: DNA
<213> ORGANISM: Artificial Sequence
<220> FEATURE:
```

```
<223> OTHER INFORMATION: Primer

<400> SEQUENCE: 28
ttatcattgg gcagagag                                                    18

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
aatcccatca ccatcttcc                                                   19

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gtccttccac gataccaaag                                                  20
```

US 9,980,982 B2

HE4 BASED THERAPY FOR MALIGNANT DISEASE

RELATED APPLICATIONS

This application is a national stage application, filed under 35 U.S.C. § 371, of International Application No. PCT/US2012/041080, filed Jun. 6, 2012, which claims the benefit of priority under 35 U.S.C. § 119(e) to U.S. Provisional Application No: 61/493,881, filed Jun. 6, 2011, and U.S. Provisional Application No. 61/541,663, filed Sep. 30, 2011, each of which are incorporated herein by reference in their entireties.

GOVERNMENT INTERESTS

This invention was made with government support under CA083639 and R01 CA136491 awarded by National Institutes of Health. The government has certain rights in this invention.

INCORPORATION BY REFERENCE

The contents of the text file named "35947007001WO_ST25.txt", which was created on Jun. 6, 2012 and is 9 KB in size, are hereby incorporated by reference in their entireties.

FIELD OF THE INVENTION

The invention relates generally to the field of cancer therapeutic strategies.

BACKGROUND OF THE INVENTION

Cancer is the leading cause of death in the United States for individuals in between the ages of forty and seventy-nine. In the United States alone, approximately 1,500 people die each day as a result of cancer. As such, there is a compelling need to develop new therapeutic strategies and methods for early detection and prognosis to improve treatment outcomes and overall patient survival.

SUMMARY OF THE INVENTION

The present invention is based on the discovery that modulation of human epididymal secretory protein E4 (HE4) suppresses and/or treats cancer. Optionally, HE4 is administered as combinatorial therapy in conjunction with other chemotherapeutic agents, surgery, or radiation therapy. The methods described herein are useful in the treatment of cancer in a mammal. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

The invention provides methods of suppressing tumor cell growth in a subject by identifying a subject with at least one tumor cell (e.g., at least 2, at least 10, at least 100, or at least 1,000 tumor cells). Preferably, the tumor cell is a solid tumor mass or microscopic tumor mass that may be present after excision of a primary tumor mass. For example, a surgeon removes a tumor mass from an ovary, which sometimes leaves single cells or microscopic tumor masses. The level of human epididymal secretory protein E4 (HE4) in the tumor cell is modulated. For example, the subject to be treated is diagnosed with cancer, e.g., the tumor cell is a malignant tumor cell. Suitable types of tumor cells include cancer progenitor cells and cancer stem cells. In preferred embodiments, the tumors to be treated include ovarian cancer, endometrial cancers, lung cancer and breast cancer (e.g., adenocarcenoma, squamous cell carcinoma, or small cell carcinoma).

In one aspect, the level of HE4 in the tumor cell is modulated by administering an HE4 inhibitor to the tumor cell. Preferably, the HE4 inhibitor is a neutralizing anti-HE4 antibody, an antisense macromolecule, a small interfering ribonucleic acid (siRNA), a small hairpin RNA (shRNA), or a small molecule inhibitor. Optionally, a testosterone compound is co-administered.

For example, an antisense molecule or HE4 modulating phosphorothio oligo comprises a nucleotide sequence of SEQ ID NOs: 1, 2, 3, 4, or 5.

```
                                           (SEQ ID NO: 1)
5' G*A*C*A*C*C*T*T*C*C*C*A*C*A*G*C*C*A*T*T 3'

(SEQ ID NO: 2)
5' G*A*C*A*C*C*T*T*C*C*C*A*C*A*G*C*C*A*T*T*G 3'

(SEQ ID NO: 3)
5' G*A*C*A*C*C*T*T*C*C*C*A*C*A*G*C*C*A*T 3'

(SEQ ID NO: 4)
5' A*C*A*C*C*T*T*C*C*C*A*C*A*G*C*C*A*T*T*G 3'

(SEQ ID NO: 5)
5' A*C*A*C*C*T*T*C*C*C*A*C*A*G*C*C*A*T*T 3'
```

The * indicates a phosphorothioate internucleotide linkage. Phosphorothioates (or S-oligos) are a variant of normal DNA in which one of the nonbridging oxygens is replaced by a sulfur. The sulfurization of the internucleotide bond dramatically reduces the action of endo- and exonucleases2 including 5' to 3' and 3' to 5' DNA POL 1 exonuclease, nucleases S1 and P1, RNases, serum nucleases and snake venom phosphodiesterase.

A pharmaceutical composition for suppressing tumor growth or reducing tumor burden in a subject comprises one or more of the oligonucleotides described above, e.g, SEQ ID NO: 4 or SEQ ID NO:2. In another example, a pharmaceutical composition for suppressing tumor growth comprises a combination of at least two compounds selected from the group consisting of an HE-4 specific oligonucleotide (e.g., SEQ ID NO: 1, 2, 3, 4, or 5), an HE4-specific antibody or antigen binding fragment thereof, and a testosterone compound.

Alternatively, the level of HE4 in the tumor cell is modulated by over-expressing HE4 in the tumor cell. The HE4 is over-expressed in the tumor cell by administering an HE4 gene under the control of an HE4 promoter to the tumor cell. Also provided are methods of modulating the level of HE4 in the tumor cell by administering synthetic HE4, recombinant HE4, or a fragment thereof to the tumor cell. Alternatively, the level of HE4 in the tumor cell is modulated with MT19c or PT19c.

Optionally, the HE4 modulators are administered in conjunction with a chemotherapeutic agent. Suitable methods of administration include oral, intrathecal, intravenous, intraperitoneal (i.e., throughout 6 cycles over 6 months), intramuscular, or subcutaneous administration or as per the need and technologies in vogue. Preferably, the chemotherapeutic agent is selected from the group consisting of an alkylating agent, an antimetabolite, an anthracycline, an antitumor antibiotic, a monoclonal antibody, a platinum agent, a plant alkaloid, a topoisomerase inhibitor, a vinca alkaloid, a taxane, and an epipodophyllotoxin. Specifically, the chemotherapeutic agent is selected from the group consisting of platinum based chemotherapeutics cisplatin and carboplatin), taxanes (i.e., paclitaxel and docetaxel), doxorubicin, camptothecin, etoposide, and a vitamin D analog or derivative such as a non-hypercalcemic heterocyclic analog of vitamin D2, e.g., MT19C; or others discussed in U.S. Ser. No. 12/096,857 (U.S. Publication No. US 2009-0221529 A1), which is incorporated herein by reference. In some cases, therapeutic genes are administered under the control of an HE4 promoter. For example, a TP53 gene (encoding P53) under the control of an HE4 promoter is administered to the tumor cell. For example, HE4 modulators are administered before, after, or simultaneously with chemotherapeutic agents such as alkylating agents (e.g., chlorambucil, cyclophosphamide, ccnu, melphalan, procarbazine, thiotepa, bcnu, and busulfan), antimetabolites (e.g., 6-mercaptopurine and 5-fluorouracil), anthracyclines (e.g., daunorubicin, doxorubicin, idarubicin, epirubicin, and mitoxantrone), antitumor antibiotics (e.g., bleomycin), monoclonal antibodies (e.g., alemtuzumab, bevacizumab, cetuximab, gemtuzumab, ibritumomab, panitumumab, rituximab, tositumomab, and trastuzumab), platinums (e.g., cisplatin, oxaliplatin, and carboplatin), plant alkaloids (e.g., vincristine), topoisomerase I or II inhibitors (e.g., irinotecan, topotecan, amsacrine, etoposide, etoposide phosphate, and teniposide), vinca alkaloids (e.g., vincristine, vinblastine, vinorelbine, and vindesine), taxanes (e.g., paclitaxel and docetaxel), epipodophyllotoxins (e.g., etoposide and teniposide), nucleoside analogs, and angiogenesis inhibitors (e.g., Avastin (beracizumab), a humanized monoclonal antibody specific for VEGF-A).

This invention also provides for a method of therapy utilizing a recombinant HE4-based active antitumor immunity vaccine against cancer, e.g., ovarian cancer, endometrial cancer, breast cancer, lung cancer or prostate cancer. Part of the invention includes design and production of glutathione s-transferase (GST)-HE4 and involves priming or pulsing dendritic cells with HE4 or GST-HE4. These HE4-primed dendritic cells are employed to generate immunity in animals against tumors that express HE4 or against tumors that are under the influence of HE4-induced signaling.

HE4 vaccine-based immunity elicited by immunization with the recombinant HE4 antigen is administered to individuals diagnosed as suffering from viral infections, fungal infections, bacterial infections, autoimmune disorders, immune compromised disorders, inflammatory disorders, and genetic disorders. The treatment is also useful for the management of pain. Such antigen may include the full length or part peptidic length of the known HE4 amino acid sequences. For example, the sequence is described in UniProtKB/Swiss-Prot, Q14508 (WFDC2_HUMAN; Last modified Apr. 18, 2012. Version 117, the entire listing including alternative splice variants and isoforms is hereby incorporated by reference).

MPACRLGPLA AALLLSLLLF GFTLVSGTGA EKTGVCPELQ ADQNCTQECV SDSECADNLK CCSAGCATFC SLPNDKEGSC PQVNINFPQL GLCRDQCQVD SQCPGQMKCC RNGCGKVSCV TPNF (SEQ ID NO:6, known as "isoform 1" or "canonical sequence"; residues 1-30 correspond to signal sequence; 31-124 represents mature protein; WAP1 domain corresponds to residues 31-73 and WAP2 domain corresponds to residues 74-123).

The nucleic acid sequence (mRNA, cDNA) is described in GENBANK Accession No. X63187.1 GI:32050 (hereby incorporated by reference). Five isoforms are produced by alternative splicing. In isoform 2, the sequence differs from the canonical sequence as follows: 2-23 (of SEQ ID NO:6): PACRLGPLAAALLLSLLLFGFT (SEQ ID NO: 11)→LQVQVNLPVSPLPTYPYSFFYP (SEQ ID NO: 7) and 24-74 of SEQ ID NO:6 are missing. Isoform 3 isoform differs from the canonical sequence as follows: 27-74 of SEQ ID NO: 6 are missing. Isoform 4 differs from the canonical sequence as follows: 71-79 (of SEQ ID NO:6) SLPNDKEGS (SEQ ID NO: 12)→LLCPNGQLAE (SEQ ID NO: 8) and 80-124 of SEQ ID NO:6 are missing. Isoform 5 differs from the canonical sequence as follows: 75-102 (of SEQ ID NO: 6) DKEGSCPQVNINFPQLGLCRDQCQVDSQ (SEQ ID NO: 13)→ALFHWHLKTRRLWEISGPRPRRPTWDSS (SEQ ID NO:9) and 103-124 of SEQ ID NO:6 are missing.

With regard to isoform 1, there is one glycosylation site at residue 44, and disulfide bonds occur between the following residues: 36←→62, 45←→66, 49←→61, 55←→70, 80←→110, 93←→114, and 97←→109 (coordinates are based on the sequence of SEQ ID NO:6)

Useful antibodies are characterized by a binding specificities to the epitope sequences described above (e.g., 10, 20, 30, 40, 50, 60, 70, 80, 90 or all 94 amino acids of SEQ ID NO:6) as well as the full sequence or any part of a HE4 sequence such as: MLQVQVNLPVSPLPTYPYSFFYPDKEGSCPQVNINFPQLGLCRDQCQVDSQCPGQMKCCRNGCGKVSCVTPNF (SEQ ID NO:10) e.g. MLQVQVNLPVSPLPTYPYSFFYPDKEGSCPQVNINFPQLGLCRDQCQVDSQCPGQMK CCR (of SEQ ID NO:10) (SEQ ID NO: 14), or MPACRLGPLA (of SEQ ID NO: 6) (SEQ ID NO: 15), AALLLSLLLF (of SEQ ID NO:6) (SEQ ID NO: 16), GFTLVSGTGA (of SEQ ID NO:6) (SEQ ID NO: 17), EKTGVCPELQ (of SEQ ID NO:6) (SEQ ID NO: 18), ADQNCTQECV(of SEQ ID NO:6) (SEQ ID NO: 19), SDSECADNLK (of SEQ ID NO:6) (SEQ ID NO: 20), CCSAGCATFC (of SEQ ID NO:6) (SEQ ID NO: 21), SLPNDKEGSC (of SEQ ID NO:6) (SEQ ID NO: 22), PQVNINFPQL (of SEQ ID NO: 6) (SEQ ID NO: 23), GLCRDQCQVD (of SEQ ID NO:6) (SEQ ID NO: 24), SQCPGQMKCC (SEQ ID NO:6) (SEQ ID NO: 25), RNGCGKVSCV (of SEQ ID NO:6) (SEQ ID NO: 26) or any combination thereof in both forward and reverse direction can be used as an antigen to develop HE4 neutralizing antibody or vaccine. Similarly, glycosylation at various residues (e.g. residue-44) and disulfide bond modifications amino acid residues (at 36 to 62, 45 to 66, 49 to 61, 55 to 70, 80 to 110, 93 to 114, 97 to 109, 103 to 119 or to reverse of it) or alternative splice variants such as PACRL . . . LFGFT (SEQ ID NO: 11)→LQVQVNLPVSPLPTYPYSFF YP (SEQ ID NO: 7) in isoform 2; SLPNDKEGS (SEQ ID NO: 12)→LLCPNGQLAE (SEQ ID NO: 8) in isoform 4; DKEGS . . . QVDSQ (SEQ ID NO: 13)→ALFHWHLKTRRLWEISGPRPRRPTWDSS (SEQ ID NO:9)in isoform 5. Alternatively, the amino acids missing in other splice variants 24-74 (in isoform-2), 27-74 in isoforms-3, 71-79 in the isoform-4, 80-124 in isoform-4, 103-124 in isoform-5 can be used to generate neutralizing antibody or vaccine. The invention includes a pharmaceutical composition comprising one or more antibodies that bind to HE4, e.g., neutralizing monoclonal antibodies specific for an epitope of mature HE4. The antibody is a polyclonal antisera or monoclonal antibody. The invention encompasses not only an intact monoclonal antibody, but also an immunologically-active antibody fragment such as one that binds to an HE4 epitope, e.g., a Fab or (Fab)$_2$ fragment; an engineered single chain FV molecule; or a chimeric molecule, e.g., an antibody which contains the binding specificity of one antibody, e.g., of murine origin, and the remaining portions of another antibody, e.g., of human origin.

The invention provides i) methods for altering HE4 expression levels (e.g., over-expression, over production or suppression) in tumors or tumor cells or cancer progenitor or cancer stem cells (CSCs), ii) applications of altered HE4 expression in the treatment of cancer and other pathological conditions in human patients, iii) delivery of therapeutic or functional genes or gene components or isoforms thereof via HE4 promoter, and iv) HE4 antibodies to treat human diseases and malignancies. For example, the HE4 gene/gene product is over-expressed to suppress tumor onset and growth, induce apoptosis, suppress the pro-survival and antiapoptotic genes or proteins, arrest cell cycle progression, metastasis, angiogenesis, and to correct proliferative disorders to suppress tumor growth. Therapeutic HE4 overexpression according to the described methods also leads to an enhanced response to other therapeutic agents such as MT19c. For example, the MT19c response is enhanced by 20%, 50%, 2-fold, 4-fold, or more when coupled with therapeutic overexpression of HE4.

The invention also relates to the treatment of inflammatory and opportunistic infections by altering HE4. Also included in the invention is the protection from bacterial or fungal or viral infections in human organs by altering the HE4 or related family member gene(s). The over-expression of HE4 is achieved by various means, such as incorporating or delivering a strategically designed complementary deoxyribonucleic acid (cDNA) through over-expression vectors, or an inducible or conditional vector and by other genetic or gene-product manipulations. Additionally, HE4 expression levels are altered by using small molecules as well. Suppression of HE4 is achieved by applications of antisense macromolecules, small interfering ribonucleic acid (siRNA), small hairpin RNA (shRNA), or by specific inhibitors of HE4 or pan whey acidic protein (WAP) family genes (e.g., HE4, HE4a or Elafin) inhibitors. Suppression or overexpression of HE4 is transient or permanent/stable. In one aspect, HE4 or related family gene's expression is suppressed indirectly by enforcing down-regulation of proteins upstream to HE4 in various signal transduction pathway.

In another aspect, intracellular HE4 expression is altered through inhibition or enhancement of the N-glycosylation of HE4 and its isoforms. Optionally, the inhibition of HE4 N-glycosylation is achieved by known N-glycosylation inhibitors (e.g., Tunicamycin or amphomycin). Other commonly used methods to inhibit N-glycosylation involve the use of N-glycosidase enzymes or use of commercially available deglycosylation kits. The enhanced glycosylation of HE4 is also achieved by commercially available glycosylation kits.

The invention provides methods of suppressing tumor cell growth in a subject by diagnosing a subject with an HE4-expressing tumor, and modulating the level of HE4 in or on the tumor in the subject. Also included are methods of suppressing tumor cell growth in a subject by identifying a subject that has been diagnosed with an HE4-expressing tumor, and modulating the level of HE4 in or on the tumor in the subject.

Also provided are methods of identifying a subject who is responsive to HE4 modulation. First, an HE-4 modulating agent is administered to a subject having an HE-4 expressing tumor or a population of HE-4 expressing tumor cells obtained from the subject is contacted with the HE-4 modulating agent. Subsequently, (b) the level of HE-4 in the subject or expressed by the tumor cells is determined, wherein a change the level of HE-4 indicates that the subject is responsive to HE-4 modulating therapy.

Suitable methods of detecting HE4 include western blot and enzyme-linked immunosorbent assay (ELISA). Exemplary methods of detecting HE4 include an immunoassay kit or a fluorescent antibody. For example, HE4 is detected via an enzyme immunoassay (EIA) kit, radioimmunoassay (RIA) kit, a fluorescein isothiocyanate (FITC) anti-rabies monoclonal antibody, or an angiotensin converting enzyme assay.

The invention also provides methods of monitoring therapeutic efficacy of an HE4 modulating agent. First, an HE-4 modulating agent is administered to a subject diagnosed as comprising an HE-4 expressing tumor. Subsequently, the level of HE4, CA125, or both is detected in or on a tumor cell obtained from the subject or in a sample of bodily fluid obtained from the subject, wherein a decrease in the level of HE4 in the tumor cell or the bodily fluid indicates the HE4 modulator suppressed tumor cell growth in the subject.

The invention also provides application of HE4 gene modulation in the i) enhancement of sensitivity or re-sensitization or priming of the chemotherapy resistant tumor or tumor cells to chemotherapeutics, ii) sensitization of molecular targets of drugs or agents or desensitization of the chemoresitance targets and their functions (e.g., glycoprotein-P), iii) enhancement of efficacy or outcome of surgery, chemotherapy or radiation therapy in combination with HE4 gene level alterations, iv) suppression of resistance factors against chemotherapy, v) analyses of HE4 gene signatures or gene products in healthy human subjects to determine their predisposition or resistance to various pathological conditions such as cancer, e.g., ovarian, endometrial and or lung cancers.

Yet another part of the invention encompasses the delivery of a gene or multiple genes, or components of genes, gene products, promoters, repressor, co-promoters, co-repressors via HE4 (e.g., via HE4 promoters) in cells or tissues or tumors or tissue showing afflictions or diseases. HE4 can be upstream or downstream of the gene to be delivered. Included are the vectors, conditional vectors both on/off vectors with variety of antibiotic resistant genes. For example, p53 or diphtheria toxin gene is delivered using a HE4 promoter.

Yet another part of this disclosure relates to the use of recombinant HE4 to suppress the tumor cell proliferation either as single agent or in combination with chemotherapeutic agent(s), surgery or radiation.

The invention provides for the induction of the HE4 gene/gene product over-expression or activation to suppress the tumor onset and growth, induce apoptosis, suppress the expression of pro-survival and anti-apoptotic genes or proteins, arrest cell cycle progression, reduce or inhibit metastasis and angiogenesis and to correct proliferative disorders to suppress tumor growth via various apoptotic or necrotic pathways leading to cancer cell death or reduction or disappearance of tumor. The suppression of HE4 is achieved by HE4 inhibitors, siRNA, or shRNA or oligos. Such tumors are treatment-naïve or treatment experienced tumors and cancer cells including the cancer progenitors or cancer stem cells. Another art included in this invention relates to the treatment of inflammatory and opportunistic infections by altering HE4. Included in this invention is the protection from bacterial or fungal or viral infections in human organs by altering the HE4 or related family member gene(s).

Also included in the use of HE4 in the treatment of human diseases (e.g., cancer, especially ovarian cancer) by altering HE4 levels in the body or delivering other therapeutic genes (e.g., p53 gene) via HE4 promoters in a human patient. The compositions and methods described herein are also used to predict the predisposition of a human being to a diseases (e.g., cancer, autoimmune disorders, inflammatory disorders, or preeclampsia) on the basis of pre-HE4 levels.

Also provided are methods to enhance the therapy or surgery outcome of a patient via alteration of HE4 levels and methods to reduce the toxicity or side effects related to chemotherapy in a human subject via alteration of HE4 levels.

Also included are methods to enhance the immune response or correct the altered immune response of human subjects via alteration of HE4. The invention also includes methods for developing immunity in immune-depleted or healthy human subjects against approaching disease states, as well as the use of recombinant HE4, a fragment thereof, or a neutralizing HE4 antibody to treat human patients.

As used herein, an "isolated" or "purified" nucleotide or polypeptide (e.g., an HE4 nucleotide or polypeptide) is substantially free of other nucleotides and polypeptides. Purified nucleotides and polypeptides are also free of cellular material or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified nucleotides and polypeptides, e.g., HE4 is one that is at least 90%, 91%, 92%, 93%, 94%, 95%, 96%, 97%, 98%, 99%, or 100% (w/w) of the desired oligosaccharide by weight. Purity is measured by any appropriate standard method, for example, by column chromatography, thin layer chromatography, or high-performance liquid chromatography (HPLC) analysis. The nucleotides and polypeptides are purified and used in a number of products for consumption by humans as well as animals, such as companion animals (dogs, cats) as well as livestock (bovine, equine, ovine, caprine, or porcine animals, as well as poultry). "Purified" also defines a degree of sterility that is safe for administration to a human subject, e.g., lacking infectious or toxic agents.

Similarly, by "substantially pure" is meant a nucleotides and polypeptides that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The terms "express" and "over-express" are used to denote the fact that, in some cases, a cell useful in the method herein may inherently express some of the factor that it is to be genetically altered to produce, in which case the addition of the polynucleotide sequence results in over-expression of the factor. That is, more factor is expressed by the altered cell than would be, under the same conditions, by a wild type cell. Similarly, if the cell does not inherently express the factor that it is genetically altered to produce, the term used would be to merely "express" the factor since the wild type cell did not express the factor at all.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a sufficient amount of the formulation or component to provide the desired effect. For example, by "an effective amount" is meant an amount of an HE4 modulator to treat cancer. Ultimately, the attending physician or veterinarian decides the appropriate amount and dosage regimen.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIG. 1 is a series of bar charts demonstrating HE4 production by ovarian cancer cells. FIG. 1A shows HE4 concentrations in supernatants, while

FIG. 2 is a photomicrograph and a bar chart demonstrating the expression of HE4 and cell growth of SKOV-3 ovarian cancer cells after stable transfection with WFDC2/pCMV6.

FIG. 4 is a series of bar charts demonstrating HE4 production and secretion by WFDC2/pCMV6 transfected SKOV-3 ovarian cancer cell clones. The production and secretion of HE4 by overexpressing SKOV-3 clones HE4C1, -C3, -C7 in comparison to WT cells was determine by comparative EIA analysis.

FIG. 6 is a photomicrograph and a bar chart demonstrating the effect of biological or chemotherapeutic agents on HE4 expression or cellular production/secretion. Various agents were examined by RT-PCR or by a sandwich ELISA.

FIG. 10 is a line graph and a bar graph demonstrating that recombinant HE4 is cytotoxic to SKOV-3 cells.

FIG. 22 shows that screening of small molecule anticancer agents afforded MT19c as a class of antitumor agent that showed 4-8 fold higher sensitivity opposed to standard chemotherapeutics such as Cisplatin and Paclitaxel that faced strong chemoresistance upon HE4 overexpression.

FIG. 23 is a schematic, a photomicrograph, and a line graph showing the development of stable HE4 overexpressing ovarian cancer cells and the evaluation of the response to cisplatin.

DETAILED DESCRIPTION

Figure 1A:
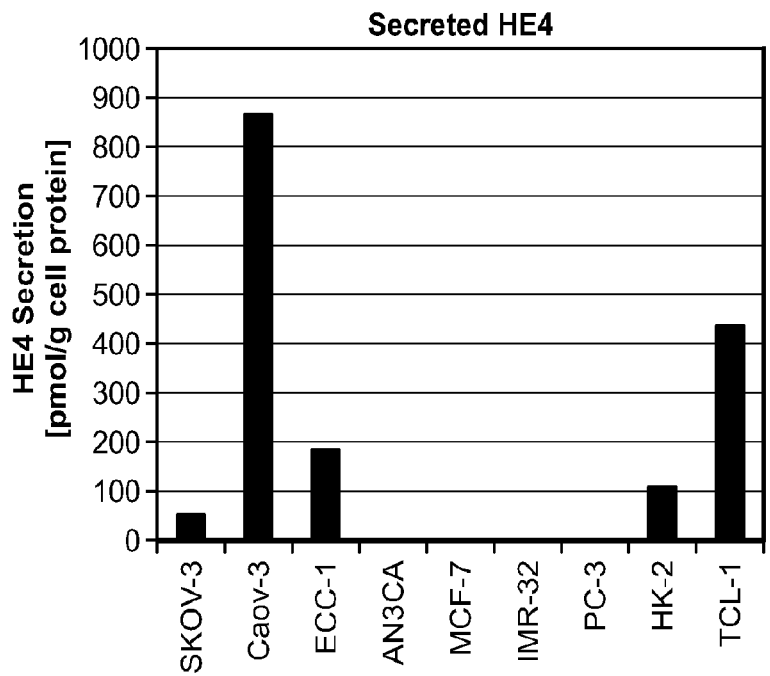

Approximately 1,500,000 new cancer cases were diagnosed in 2010, excluding the carcinoma in situ (noninvasive cancer), and basal and squamous cell skin cancer cases, which are not required to be reported to cancer registries. As such, there is a compelling need to develop new therapeutic strategies and methods for early detection and prognostication to improve treatment outcomes and overall patient survival.

Human epididymis protein 4 (HE4) was identified in the epithelium of the distal epididymis using Northern blot analysis and in situ transcript hybridization (Kirchhoff et al, 1991 Biol Reprod, 45:350-357). Subsequent studies using RNA dot blots, reverse transcription polymerase chain reaction (RT-PCR) and Northern blot analysis suggested that HE4 RNA expression is widespread (Clauss et al, 2002 Biochem J, 368:233-242). Previous studies using comparative genomic hybridization and in silico chromosomal clustering reported that human chromosome 20q12-13.2 is consistently amplified in ovarian carcinomas and harbors genes that may play causal roles in the pathogenesis of the disease. This region contains a cluster of 14 genes with homology to whey acidic protein (WAP). Among these genes is HE4 that is overexpressed in ovarian and endometrial cancers. The expression of HE4 protein is highly restricted in normal human tissues and is largely limited to the epithelium of the reproductive tracts and to the respiratory epithelium of the proximal airways. In malignant neoplasms, gene expression profiling has consistently identified up-regulation of HE4 in carcinoma of the ovary (Wang et al, 1999 Gene, 229:101-108; Hough C D et al, 2000 Cancer Res, 60:6281-6287; Gilks C B et al, 2005 Gynecol Oncol, 96:684-694).

In malignant tumor tissues, HE4 is considered biomarker for epithelial ovarian carcinoma (WO/2007/081768; WO/2007/081767; Moore R G et al., 2008 Gynecologic Oncology, 110:196-201; Moore R G et al., 2009 Gynecologic Oncology, 112:40-46 and others). Similarly, malignancies of corpus uteri are also positive for HE4. (Drapkin R et al, 2005 Cancer Res, 65:2162-2169). HE4 is also a marker for other Müllerian-derived tumors. In cell line studies, secreted HE4 was also seen in cell lines that express endogenous HE4 RNA (e.g., CaOV-3 and OVCAR5). Intracellular immunofluorescence studies revealed that HE4 is distributed in a region of the cytoplasm, or endoplasmic reticulum and the Golgi apparatus organelles (Drapkin R et al, 2005 Cancer Res, 65:2162-2169).

HE4 gene expression as a marker for inflammatory diseases and renal disorders in healthy and disease samples have been described. Described herein are results demonstrating that HE4 over-expression causes selective apoptosis and cell death in ovarian and endometrial cancer cells. Also described herein are results demonstrating that HE4 overexpression caused significant cell death in Human Umbilical Vein Endothelial cells (HUVEC), while MES 13 (mouse misangial cells) and HK2 (human kidney cells) did not undergo apoptosis or cell death under similar conditions. Described herein are results demonstrating that activation of HE4 induced caspases (-3, -8 and -9), MAP kinase (SAP/JNK, p38) activation, followed by down-regulation of pro-survival mitochondrial proteins such as BCl2, MCl-1 and BCl-xL in ovarian cancer (SKOV-3) cells. Activation of HE4 also caused PARP-1 cleavage in both ovarian cancer cells (SKOV-3) and endometrial cancer cells (ECC-1).

The invention provides a variety of diverse biological or chemical tools to achieve HE4 modulation (e.g. upregulation and downregulation) to affect cancer progression in humans and animals. For example, overexpression of HE4 using a pCMV-6-HE4 plasmid induced significant cell death as measured by caspase-3 cleavage, SAPK/JNK phohsphorylation and loss of cell viability in cancer cells. On the contrary, the data revealed that slightly higher levels of HE4 than basal can promote chemoresistance against chemotherapies. Moreover, we acheived the knock-down of HE4 via phosphoro-thio oligos (HE4 PTOs) with the sequences (e.g., SEQ ID NO: 4 or 2 as well as other sequences listed herein such as SEQ ID NO: 1, 3, or 5) or via neutralizing antibodies against the peptide sequences outlined elsewhere in this application or by chemical agents such as testosterone, or its analogs.

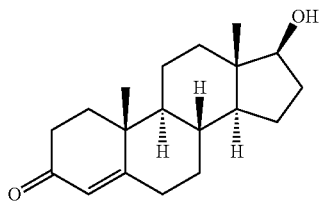

Testosterone (structure provided above) has the molecular formula $C_{19}H_{28}O_2$. Testosterone compounds are available in a number of formulations such as testosterone propionate (Oreton) and of methyl testosterone (Oreton-M), which are available from Schering. Other formulations include Androderm, Androlin, Mertestate, Testoderm, Testosteron, Oreton, Synandrol F, trans-Testosterone, Andronaq. A number of synthetic analogs of testosterone have also been developed. Some analogs have improved bioavailability and metabolic half life relative to testosterone. Many of these analogs have an alkyl group introduced at the C-17 position in order to prevent conjugation and hence improve oral bioavailability. These are the so-called "17-aa" (17-alkyl androgen) family of androgens such as fluoxymesterone and methyltestosterone.

The knock-down of HE4 by siRNA, HE4-PTOs, testosterone or its chemical analogs or neutralizing antibodies have demonstrated significant tumor burden reduction in animals or reduced the proliferation of cancer cells either as single entities, or combinations thereof. Remarkably, the combinations that use multiple HE4 targeting agents has demonstrated significant cell viability reduction in cultured cancer cell experiments.

As described in detail below, a FACS analysis of SKOV-3 cells induced with a HE4 over-expression vector showed that activation of HE4 resulted in a significant increase in Propidinium Iodide (PI) positive population (apoptosis) along with concomitant decrease in Rhodamine123 population. Another FACS analysis of SKOV-3 cells induced with HE4 overexpressed vector showed that activation of HE4 caused significant arrest of cells in sub-G1/G0 phase population compared to vehicle or transfection reagent (Lipofectamine).

Additionally, as described in detail below, recombinant HE4 treatment results in the reduction of cell viability of proliferating ovarian cancer cells (SKOV-3; IC50~1-8 uM). Further, SKOV-3 cells treated with recombinant HE4 and cisplatin, concomitantly or separately showed synergized or enhanced suppression of cell-viability in comparison to vehicle, HE4 or cisplatin alone.

On the basis of the experiments described herein, it was determined that activation of HE4 gene presents features of gene therapy or vaccine therapy to treat cancer in humans. Prior to the invention described herein, the implications of HE4 over-expression in the pathology of ovarian cancers were not known. Rather, prior to the invention described herein, the literature on HE4 concentrated in efforts to extend application of HE4 as a biomarker for variety of cancers. As described herein, HE4 is a cytotoxic/cytostatic gene, and over-expression of HE4 reduced the growth of ovarian and endometrial cancer in vitro. HE4 based gene therapy is applied to a variety of human cancers, including ovarian cancer, endometrial cancer, and lung cancer. The invention provides for treatment of ovarian cancer with HE4 activation alone. Alternatively, HE4 activation can be utilized to increase the sensitivity of the cancer cells (priming) to existing therapies to overcome chemotherapy resistance or enhance the treatment outcome. HE4 based gene therapy is especially applicable to ovarian and endometrial cancers, because the disease remains confined mainly to the abdominal cavity even in the advanced stages (Robertson III M W et al., 1998 Cancer Gene Ther, 5:331-336), and the abdominal cavity remains highly accessible in ovarian cancer patients. Further, HE4 based gene therapy is a tool to treat lung and prostate cancer because it is possible to achieve higher vector concentrations with minimal tissue distribution and toxicity (Tanyi J L L R et al., 2002 Gynecol Oncol, 85:451-458).

The advantage of delivering the therapeutic HE4 vector significantly reduces the limitations that exist for ovarian and other cancer gene therapy, i.e., toxicity due to nonspecific transduction of normal tissues. The most direct approach to overcoming this limitation is the utilization of tissue- and tumor-specific promoters. Several candidate promoters (other than HE4 and its isoforms) control therapeutic gene expression in ovarian cancer cells. The human chorionic gonadotropin (hCG) promoter, when sub-cloned upstream of the diphtheria toxin-A chain gene in a retrovirus, showed selective killing of ovarian cancer cell lines with minimal toxicity to normal ovary and fibroblasts (Lidor Y J et al., 1997 Am J Obstet Gynecol, 177:579-85). The serine leukocyte protease inhibitor-1 (SLP1) promoter has also been used to drive herpes simplex virus thymidine kinase (HSVTK) in SKOV-3 cells (Garver Jr R I. 1994 Gene Therapy, 1:46-50). Furthermore, cancer-specific promoters such as the telomerase gene promoter (human telomerase reverse transcriptase, hTERT) (Cong Y S et al., 1999 Hum Mol Genet, 8:137-142) have been examined for gene therapy of ovarian cancer (Bilsland A E et al., 2003 Oncogene, 22:370-380; Hiyama E and Hiyama K, 2002 Oncogene, 21:643-649). Additional approaches, including artificial promoters combined with highly efficient gene transfer vectors, may increase the therapeutic index and reduce toxicity, but have not yet been tested for ovarian cancer gene therapy. Promoters of genes frequently up-regulated in ovarian cancer provide a means to direct expression of a therapeutic gene specifically in ovarian cancer cells. Preferably, HE4 is not expressed or overexpressed using the vectors described in US Publication No. 2011/0104120 A1.

The present invention relates to: i) the development of methods to alter HE4 expression levels including over-expression in tumors or tumor cells; and ii) applications of altered HE4 expression (e.g., over-expression) in the treatment of pathological conditions in human patients. This invention provides a method and a therapeutic approach to treat mammals suffering from a diseases such as cancer. The subject is preferably a mammal in need of such treatment, e.g., a subject that has been diagnosed with cancer or a predisposition thereto. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

As described herein, activation of the HE4 gene is as a potent cytotoxic method to treat ovarian cancer and endometrial cancer cell without any toxicity to cells. For example, IC50 values demonstrated by such agent in the treatment of ovarian and endometrial cancer or other cancer cells cover a concentration range (100 μM-1 pM) correlated to the treatment time (1 min-7 days). Cancers treated by delivery of the HE4 gene, or expression of the HE4 gene, or conditional activation of the HE4 gene, or modulation of HE4 gene expression, or application of HE4 gene products (mRNA, proteins) in single treatment or combinational treatment with other drugs may be of primary, secondary, metastatic, or cancer progenitor, or cancer stem cell origin. Generally, cancer includes benign tumors, malignant tumors, solid tumors or other cancers. Examples of solid cancers can be any type or subtype of breast, ovarian, endometrial, cervical, neuroblastoma, lung cancer, colon cancer, CNS cancer, melanoma, renal, prostate, medulloblastoma, head and neck cancer, esophagus cancer, pancreatic cancer, skin cancer, thyroidal cancer, peripheral nerve sheath cancer, ependymoma, craniopharyngiom, astrocytoma (juvenile pilocytic astrocytoma, subependymal giant cell astrocytoma, pleomorphic xanthoastrocytoma, anaplastic astrocytoma, or gliomatosis cerebri), meningioma, germinoma, glioma, mixed glioma, choroid plexus tumor, oligodendroglioma, peripheral neuroectodermal tumors, CNS lymphoma, pituitary adenoma, or Schwannoma. Activation of HE4 gene to suppress the tumor burden is also applied against types or subtypes of non-solid tumors such as cancers of blood or lymphatic systems, e.g., Leukemia or lymphoma. In another aspect, these approaches can be applied as a neoadjuvant, in combination with existing therapies, or as adjuvant therapies. Optionally, the methods additionally comprise treating the subject with chemotherapy, surgery or radiation.

In one embodiment, the invention relates to the use of recombinant HE4 protein or its modified forms as a selective cytotoxic or cytostatic, agent. As described herein, recombinant HE4 selectively caused apoptosis and cell death among ovarian and endometrial cancer cells. The immortalized human trophoblasts (HTR) or mouse kidney cells were comparatively less sensitive to the cytotoxic effects of HE4. Various other antitumor features of recombinant HE4 include: i) arresting the cell cycle progression of ovarian cancer cells; ii) activation of apoptotic bio-markers such as cleaved caspases-3, parp-1 cleavage and activation of MAP kinases; iii) in-activation of pro-survival markers such as MAP kinases and, iii) synergizing the efficacy of the anti-cancer agents, which may involve synergized activation of apoptosis and or suppression of the resistance or efflux biomarkers against the chemotherapeutic agents. One such example is the possible suppression of HE4 induced EGF1R or glycoprotein-1, BRCA-1/2, AKT, PI-3K expression and/or activation that accounts for cisplatin resistance in ovarian cancer cells or tumors. Other well characterized chemoresistance factors include multi-drug resistance gene-1, glutathione S-transferase pi (GSTP1), O(6)-methylguanine-DNA methyltransferase (MGMT), and mutant p53 (Kern D H., 1998 Cancer J Sci Am., 4:41-45). A substantial percentage of tumors over-expressed biomarkers associated with drug resistance, including MGMT (67%), GSTP1 (49%), and mutant p53 (41%) (Parker R J et al., 2004 J Neurooncol, 66:365-375).

In another embodiment, the invention relates to the induction of HE4 gene and/or protein over-expression to suppress the proliferation of cancer cells and tumor growth. Such cancer cells are or are derived from human organs such as ovarian, breast, nervous system (CNS and peripheral), blood, lung, bone, liver, renal, pancreas, colorectal system, excretory system, skin, endometrium, esophagus and may be part of metastatic cancer spread over multiple organs in the same subject. In one aspect, the over-expression of HE4 in cancer cells is accomplished by delivering an HE4 vector (cDNA or promoter of HE4) using various methods known in the literature, e.g., using transfection chemicals (lipofectamine, surefect etc), heat shock, electroporation or liposomes. Optionally, the vector is further coupled with other suicide genes, apoptotic genes, cell cycle regulatory genes or MAP kinases or genes that can suppress the chemoresistance factors in the cancer cells and make them more sensitive to the chemotherapy. The vector can co-deliver other diagnostic genes, e.g., luciferases, CA125, mesothelin that can enhance the diagnostic and chemotherapeutic efficiency of the HE4 in various cancer cell-types.

This invention also encompasses monitoring the levels of pre-HE4 protein levels in serum, or tissues in healthy/subjects with familial history of cancer, or viral or autoimmune diseases especially females. The comparison of the genetic fingerprints/configuration of pre-HE4 in the subject with historical familial/global data/databases of the cancer patients using bio-informatics approaches determine the degree of pre-disposability of the subject to ovarian, endometrial, breast or lung cancer or other cancers or pathologies such as cystic fibrosis where pre-HE4 expression and localization is significantly enhanced.

This invention also relates to the induction of HE4 gene and or protein expression to suppress the metastasis of tumor cells to other organs from the originating source. An example of the present art is HE4 induced suppression of ovarian cancer metastasis to neighboring organs, liver, lungs, colon (>50%), or lymph nodes. Also described herein is the inhibition of angiogenesis in tumors by modulating expression of HE4 gene or gene product. The invention provides a method of inhibiting angiogenesis in mammal, preferably human, subjects. The method comprises delivery of the HE4 gene, expression of the HE4 gene, conditional activation of the HE4 gene, delivery of a HE4 gene product in the tumor (s) or cancer cells including cancer stem cells of a subject to inhibit angiogenesis and secondary pathological outcomes. Angiogenesis, the formation of new vessels from preexisting vasculature, is critical to tumor survival, growth and metastasis in ovarian or other human cancers. Deregulation of normal angiogenic processes occurs with the cancer's acquisition of the ability to secrete pro-angiogenic factors. The local imbalance of endogenous angio-stimulators and angio-inhibitors promotes vascularization and vascular leak that feed the ever starved tumors.

The subject may have a cancer, an ocular disease (e.g., macular degeneration, a maculopathy, diabetic retinopathy or retinopathy of prematurity (retrolental fibroplasia)); a skin disease (e.g., infantile hemangioma, verruca vulgaris, psoriasis, neurofibromatosis, or epidermolysis bullosa), an autoimmune disease (e.g., rheumatoid arthritis), a gynecologic disease (e.g., endometrial polyp, endometriosis, ovarian hyperstimulation syndrome, polycystic ovarian syndrome (PCO), or preeclampsia) or a cardiovascular disease (e.g., coronary artery disease, ischemic cardiomyopathy, myocardial ischemia, arteriosclerosis, atherosclerosis, atherosclerotic plaque, neovascularization, arterial occlusive disease, ischemia, ischemic or post myocardial ischemia revascularization, peripheral vascular disease or intermittent claudication), or a gastrointestinal disease (e.g., Crohn's disease and ulcerative colitis, Buerger disease, thromboangiitis obliterans, arteriolosclerosis obliterans, ischemic ulcers, multiple sclerosis, idiopathic pulmonary fibrosis, HIV infection, plantar fasciitis, Von-Hippel Landau disease, CNS hemangioblastoma, retinal hemangioblastoma, thyroiditis, benign prostate hyperplasia, glomerulonephritis, ectopic pregnancy and ectopic bone formation or keloid). In one aspect, the cancer is biliary tract cancer, bladder cancer, bone cancer, brain cancer, choriocarcinoma, breast cancer, cervical cancer, colon and rectum cancer, connective tissue cancer, cancer of digestive system, endometrial, esophageal, eye cancer, fibromael, cancer of head and neck, gastric cancer, intraepithelial neoplasm, kidney cancer, larynx cancer, leukemia including acute myeloid leukemia, acute lymphoid leukemia, chronic lymphoid leukemia, liver cancer, lung cancer (e.g., small cell and non-small cell), lymphoma (including Hodgkin's or non-Hodgkin), melanoma, oral cavity cancer (lip, tongue, mouth and pharynx), ovarian cancer, pancreatic cancer, prostate cancer, retinoblastoma, rhabdomyosarcoma, rectal cancer, renal cancer and cancers of the respiratory tract, sarcoma, skin cancer, stomach cancer, testicular cancer, thyroid cancer, uterine cancer, cancers of the urinary system, a sarcoma or carcinoma. The cancer may be a metastatic cancer. The method may additionally comprise treating the subject with additional surgery, chemotherapy or radiation therapy. In another embodiment, this invention relates to the suppression of HE4 N-glycosylation in cancer cells by using N-glycosylation inhibitors. Suitable examples of such inhibitors are Tunicamycin and Amphomycin. HE4 is secreted in serum as N-glycosylated protein post endoplasmic reticulum (ER) or Golgi apparatus processing in the cancer cells. This kind of cellular processing reduces the HE4 cellular levels. Tunicamycin or amphomycin can inhibit the HE4 secretion by blocking its N-glycosylation that can enhance intracellular HE4 half life. The enhanced intracellular retention due to suppressed excretion of HE4 (e.g., as N-glycosylated HE4) can induce various layers of cytotoxic or cytostatic effects in cancer cells.

Exemplary tumors to be treated include all HE4-expressing or overexpressing tumors, e.g., ovarian cancers (for example, germ cell cancer, stromal cell cancer, and epithelial cell cancer) and endometrial cancers (for example, endometrioid cancer and clear cell cancer). Approximately 80% of serous cancer cells, 100% of endometrioid cancer cells, 50% of clear cancer cells, and 30-40% of mucinous cancer cells express HE4.

The invention also provides for the modulation of HE4 gene or gene product expression to suppress cancer cell proliferation. Alteration of HE4 expression in cancer cells blocks the cell-cycle progression in various phases of the cell-cycle by altering the cell cycle regulatory machinery in the cells. The cell cycle, or cell-division cycle, is the series of events that takes place in a cell leading to its division and duplication (replication). The molecular events that control the cell cycle are ordered and directional, i.e., each process occurs in a sequential fashion and it is impossible to "reverse" the cycle. The cell-cycle arrest can be targeted to inhibit cancer cell proliferation Inhibition of cell cycle progression or cell cycle regulators (such cyclins, cyclin dependent kinases) can also be targeted.

In one aspect, HE4 expression is targeted to suppress other hyperproliferative disorders in humans. Hyperproliferative disorders that are targeted based on HE4 over/under-expression include psoriasis, kidney, liver and hyperthyroid disorders. The over-expression of HE4 is achieved by cDNA, specific or non-specific over expression vectors, inducible or conditional vectors and by genetic or gene-product manipulations or using small molecules. Suitable inducible factors include tetracycline (tet), Doxyclin, and Puromycin. In another aspect, the invention provides the pharmaceutical composition for the treatment of foregoing diseases, disorders or conditions. The composition comprises delivering one or more ligands mentioned in this disclosure in conjunction with HE4 expression modulation. An appropriate vector is utilized to deliver HE4, while another pharmaceutical carrier is utilized to deliver the ligands or chemotherapeutic agent. For example, one of the compounds (cisplatin) can be formulated with approved pharmaceutical carriers, while a tet-inducible HE4 vector is delivered through liposomal, electroporation or CaCl2 or through various transfecting agents (e.g., Lipofectamine, surefect, other cationic transfection lipids: DOTMA, DOTAP, DMRIE, DCRIE, DOSPA, DMDHP or DOGS; DharmaFECT, HiPERfect) to treat gynecologic cancers such as breast, ovarian or endometrial or non gynecologic cancers that afflict both males and females. The unit doses are preferably between 1 nanogram/kg body weight to 10 gram/kg body weight of medicament with a suitable pharmaceutical carrier. In another aspect, the HE4 gene expression vector described in this invention are co-formulated with other medicament(s) using various delivery platforms in vogue. These formulations are formulated for oral, intrathecal, intravenous, intraperitoneal (i.e., throughout 6 cycles over 6 months), intramuscular, subcutaneous administrations or as per the need and technologies in vogue.

Carcinomas are cancers of epithelial origin. Carcinomas intended for treatment with the method of this invention include, but not limited to, acinar carcinoma, acinous carcinoma, alveolar adenocarcinoma, carcinoma adenomatosum, adenocarcinoma, carcinoma of adrenal cortex, alveolar carcinoma, alveolar cell carcinoma, basal cell carcinoma, carcinoma basocellular, basaloid carcinoma, basosquamous cell carcinoma, breast carcinoma, bronchioalveolar carcinoma, bronchiolar carcinoma, cerebriform carcinoma, cholangiocellular carcinoma, chorionic carcinoma, colloid carcinoma, comedocarcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliate adenoids, carcinoma exulcere, carcinoma fibrosum, gelatinform carcinoma, gelatinous carcinoma, giant cell carcinoma, gigantocellulare, glandular carcinoma, granulose cell carcinoma, hair matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lentivular carcinoma, carcinoma lenticulare, lipomatous carcinoma, lymphoepithelial carcinoma, carcinoma mastotoids, carcinoma medullare, medullary carcinoma, carcinoma melanodes, melanotonic carcinoma, mucinous carcinoma, carcinoma muciparum, carcinoma mucocullare, mucoepidermoid carcinoma, mucous carcinoma, carcinoma myxomatodes, masopharyngeal carcinoma, carcinoma nigrum, oat cell carcinoma, carcinoma ossificans, osteroid carcinoma, ovarian carcinoma, papillary carcinoma, periportal carcinoma, pre-invasive carcinoma, prostate carcinoma, renal cell carcinoma of kidney, reserve cell carcinoma, carcinoma sarcomatodes, scheinderian carcinoma, scirrhous carcinoma, carcinoma scrota, signet-ring cell carcinoma, carcinoma simplex, small cell carcinoma, solandoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberrosum, tuberous carcinoma, verrucous carcinoma, carcinoma vilosum.

The invention also provides methods and agents to treat sarcomas. Sarcomas are mesenchymal neoplasms that arise in bone and soft tissues. Different types of sarcomas are recognized and these include: liposarcomas (including myxoid liposarcomas and pleomorphic liposarcomas), leiomyosarcomas, rhabdomyosarcomas, neurofibrosarcomas, malignant peripheral nerve sheath tumors, Ewing's tumors (including Ewing's sarcoma of bone, extraskeletal or non-bone) and primitive neuroectodermal tumors (PNET), synovial sarcoma, hemangioendothelioma, fibrosarcoma, desmoids tumors, dermatofibrosarcoma protuberance (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) and osteosarcoma (also known as osteogenic sarcoma-skeletal and extra-skeletal, and chondrosarcoma.

Optionally, the cancers to be treated are a refractory or a responding cancer. As used herein, a refractory cancer is a cancer that is resistant to the ordinary standards of care prescribed. These cancers, although initially responsive to treatment, recur and/or may be completely non responsive to the treatment. This invention can also be used to treat cancers that are immunogenic. Examples of immunogenic cancers include malignant melanoma and renal cell carcinoma, Mantel cell lymphoma, follicular lymphoma, diffuse large B-cell lymphoma, T-cell acute lymphoblastic leukemia, Burkitt Lymphoma, myeloma, immunocytoma, acute promyelocytic leukemia, chronic myeloid/acute lymphoblastic leukemia, acute leukemia, B-cell acute lymphoblastic leukemia, anaplastic large cell leukemia, myelodysplastic syndrome/acute myeloid leukemia, non-Hodgkin's lymphoma, chronic lymphocytic leukemia, acute myelogenous leukemia (AML), common (pre-B) acute lymphocytic leukemia, malignant melanoma, T-cell lymphoma, leukemia, B-cell lymphoma, epithelial malignancies, lymphoid malignancies, gynecologic carcinoma, biliary adenocarcinomas and ductal adenocarcinomas of the pancreas.

This invention also provides a method to inhibit angiogenesis in human subjects. Angiogenesis, the rapid proliferation of epithelial cells resulting in formation of new blood vessels, supports the progression and survival of tumors. As a secondary effect, angiogenesis may damage the various organs and tissues, eyes, skin, heart, blood vessels, lung, GI tract and genitourinary tract. Various methods or techniques available to assess angiogenesis, are not described herein may be used for the purpose of this invention. Methods and techniques to assess angiogenesis are known to those of ordinary skill in the art.

The methods and agents derived from this invention may be administered in combination with other therapies such as for example, radiation therapy, surgery, conventional chemotherapy or with a combination of one or more additional therapies. The agents derived from this invention may be administered alone in a pharmaceutical composition or combined with therapeutically effective and physiologically acceptable amount of one or more other active ingredients or agents. Such other active ingredient includes, but are not limited to glutathione antagonists, angiogenesis inhibitors, chemotherapeutic agent(s) and antibodies (e.g., cancer antibodies). The agents described in this invention may be administered simultaneously or sequentially. The separation in time between administrations may be minutes, hours, days or it may be longer.

For example, HE4 modulators are administered before, after, or simultaneously with chemotherapeutic agents such as alkylating agents (e.g., chlorambucil, cyclophosphamide, ccnu, melphalan, procarbazine, thiotepa, bcnu, and busulfan), antimetabolites (e.g., 6-mercaptopurine and 5-fluorouracil), anthracyclines (e.g., daunorubicin, doxorubicin, idarubicin, epirubicin, and mitoxantrone), antitumor antibiotics (e.g., bleomycin), monoclonal antibodies (e.g., alemtuzumab, bevacizumab, cetuximab, gemtuzumab, ibritumomab, panitumumab, rituximab, tositumomab, and trastuzumab), platinums (e.g., cisplatin, oxaliplatin, and carboplatin), plant alkaloids (e.g., vincristine), topoisomerase I or II inhibitors (e.g., irinotecan, topotecan, amsacrine, etoposide, etoposide phosphate, and teniposide), vinca alkaloids (e.g., vincristine, vinblastine, vinorelbine, and vindesine), taxanes (e.g., paclitaxel and docetaxel), epipodophyllotoxins (e.g., etoposide and teniposide), nucleoside analogs, and angiogenesis inhibitors (e.g., Avastin (beracizumab), a humanized monoclonal antibody specific for VEGF-A).

Examples of glutathione antagonists include but are not limited to buthionine sulfoximine, cyclophosphamide, ifosphamide, actinomycin-d and N-(4-hydroxyphenyl) retinamide (4-HPR). Examples of angiogenesis inhibitors include but are not limited to 2-methoxyestradiol (2-ME), AG3340, Angiostatin, antithrombin-III, Anti-VEGF antibody, Batimastat, bevacizumab (Avastin), BMS-275291, CA1, Canstatin, combretastatin, Combretastatin-A4 phosphate, CC-5013, captopril, celecoxib, Dalteparin, EMD121974, Endostatin, Erlotinib, Gefitinib, Genistein, Halofuginone, ID1, ID3, IM862, Imatinib mesylate, Inducible protein-10, Interferon-alpha, Interleukin-12, Lavendustin-a, LY317615, or AE-941, Marimastat, Mapsin, Medroxyprogesterone acetate, Meth-1, Meth-2, Neovastat, Osteopontin cleaved product, PEX, Pigment epithelium growth factor (PEGF), platelet growth factor 4, prolactin fragment, proliferin-related protein (PRP), PTK787/ZK222584, recombinant human platelet factor-4(rPF4), restin, squalamine, SU5416, SU6668, Suramin, Taxol, Tecogalan, Thalidomide, Tetrathiomolybdate (TM), Thrombospondin, TNP-470, Troponin I, Vasostatin, VEGF1, VEGF-TRAP and ZD6474. In some embodiment the angiogenesis inhibitor is a VEGF antagonist. The VEGF antagonist may be a VEGF binding molecule. VEGF binding molecule include VEGF antibodies, or antigen binding fragment (s) thereof. One example of a VEGF antagonist is NeXstar.

Examples of categories of chemotherapeutic agents that may be used as an additional active ingredient include, but are not limited to, DNA damaging agents and these include topoisomerase inhibitors (e.g., etoposide, camptothecin, topotecan, irinotecan, teniposide, mitoxantrone), anti-microtubule agents (e.g., vincristine, vinblastine), antimetabolite agents (e.g., cytarabine, methotrexate, hydroxyurea, 5-fluorouracil, flouridine, 6-thioguanine, 6-mercaptompurine, fludarabine, pentostatin, chlorodeoxyadenosine), DNA alkylating agents (e.g., cisplatin, mecholorethamine, cyclophosphamide, ifosphamide, melphalan, chlorambucil, busulfan, thiotepa, carmustine, lomustine, carboplatin, dacarbazine, procarbazine) and DNA strand break inducing agents (e.g., bleomycin, doxorubicin, daunorubicin, idarubicin, mitomycin C). Chemotherapeutic agents include synthetic, semisynthetic and naturally derived agents. Important chemotherapeutic agents include, but are not limited to, Avicine, Aclarubicin, Acodazole, Acronine, Adozelesin, Adriamycin, aldesleukin, Alitretinoin, Allopurinol sodium, Altretamine, Ambomycin, Ametantrone acetate, Aminoglutethimide, Amsacrine, Anastrazole, Annonaceous Acetogenins, Anthramycin, Asimicin, Asparaginase, asperlin, Azacitidine, azetepa, Azotomycin, batimastat, benzodepa, bexarotene, Bicalutamide, Bisantrene, Bisnafide, Bizelesin, Bleomycin, Brequinar, Bropirimine, Bullatacin, Busulfan, Cabergoline, cactinomycin, calusterone, caracemide, carbetimer, carboplatin, carmustine, carubicin, carzelesin, cedefingol, chlorambucil, celecoxib, cirolemycin, cisplatin, cladribine, crisnatol, cyclophosphamide, cytarabine, dacarbazine, DACA, dactinomycin, Daunorubicin, daunomycin, Decitabiue, denileukin, Dexormaplatin, Dezaguanine, Diaziquone, Docetaxel, Doxorubicin, Droloxifene, Dromostalone, Duazomycin, Edatrexate, Eflornithine, Elsamitrucin, Estramustine, Etanidazole, Etoposide, Etoprine, Fadrozole, Fazarabine, Fenretinide, Floxuridine, Fludarabine, Fluorouracil, Fluorocitabine, 5-FdUMP, Fosquidone, Fosteuecine, FK-317, FK-973, FR-66979, FR-900482, Gemcitabine, Gemtuzumab, Ozogamicin, Gold Au198, Goserelin, Guanacone, Hydroxyurea, Idarubicin, Ilmofosine, Interferon alpha and analogs, Iproplatin, irinotecan, Lanreotide, Letrozole, Leuprolide, Liarozole, Lometrexol, Lomustine, Losoxantrone, masoprocol, Maytansine, Mechlorethamine, Megestrol, Melengestrol, Melphalan, Menogaril, Metoprine, maturedepa, mitindomide, Mitocarcin, Mitogillin, Mitomalacin, Mitomycin, Mitomycin C, Mitosper, Mitotane, Mitoxantrone, Mycophenolic acid, Nocodazole, Nogalamycin, Oprelvekin, ormaplatin, Oxisuran, Paclitaxel, pamidronate, pegaspargase, Peliomycin, Pentamustine, Peplomycin, Perfosfamide, Pipobroman, Piposulfan, Piroxantrone, Plicamycin, Plomestane, Porfimer, Porfiromycin, Prednimustine, procarbazine, Puromycin, Pyrazofurin, Riboprine, Rituximab, Rogletimide, Rolliniastatin, safingol, Samarium, Semustine, Simtrazene, Sparfosate, Sparsomycin, spirogermanium, Spiromustine, Spiroplatin, Squamocin, Squamotacin, streptonigrin, streptozocin, SrCl2, Sulphofenur, Talisomycin, Taxane, Toxoid, Tecoglan, Tegafur, teloxantrone, Temoporfin, teniposide, Teroxirone, Testolactone, Thiamiprine, Thiotepa, Thymitaq, Tiazofurin, Tirapazamine, Tomudex, Top-53, Topotecan, Toremixifine, Trastuzumab, Trestolone, triciribine, Triciribine, Trimetrexate, trimetrexate glucuronate, Triptorelin, Tubulozole, uracil mustard, Uredepa, valrubicin, vapreotide, Vinblastine, Vincristine, Vindesine, Vinepidine, Vinglycinate, Vinleurosine, Vinorelbine, Vinrosidine, Vinzolidine, Vorozole, Zeniplatin, Zinostatin, Zorubicin, 2-cholrodeoxyrubicine, 2'-deoxyformycin, 9-aminocamptothecin, raltitrexed, N-propargyl-5,8-didezafolic acid, 2-cholo-2' arabinofluoro-2' deoxyadenosine, 2-cholo-2'-deoxyadenosine, anisomycin, Trichostatin, hPRL-G129R, CEP-751, Linomide, Sulfur mustard, nitrogen mustard, N-methyl-N-nitrosourea, fotemustine, Streptozotocin, dacarbazine, mitozolomide, temozolomide, AZQ, ormaplatin, CI-973, DWA2114R, JM216, JM335, Bisplatinum, Tomudex, azacitidine, cytrabincine, gemcitabine, 6-mercaptopurine, Hypoxanthine, Teniposide, CPT-11, Doxorubicin, Daunorubicin, Epirubicin, darubicin, losoxantrone, amsacrine, pyrazoloacridine, all trans retinol, 14-hydroxy-retro-retinol, all-trans retinoic acid, N-(4-hydroxyphenyl)retinamide, 13-cisretinoic acid, 3-methyl TTNEB, 9-cisretenoic acid, fludarabine, and 2-Cda. Other chemotherapeutic agent include: 20-epi1,25-dihydroxyvitamin-D3,5-ethynyl uracil, abiraterone, aclarubicin, acylfulvene, adecylpenol, adozelesin, aldesleukin, ALL-TK antagonists, altretamine, ambumastine, amidox, amifostine, amino levulinic acid, anagrelide, anastrozole, andrographolide, angiogenesis inhibitors, antagonist D, antagonists D, antarelix, anti-dorsalizing morphogenetic protein-1, antiandrogen, antiestrogen, antineoplastone, antisense oligonucleotides, aphidicolin, apoptosis gene modulators, apoptosis regulators, apurinic acid, ara-cdp-dl-PTBA, arginine aminase, asulacrine, atamestine, atrimustine, axinamastine 1 and axinamastine 2, axinamastine 3, azasetron, azatoxin, azatyrosine, baccatin III derivatives, balanol, BCR/ABL antagonist, benzochlorins, benzoylsaurosporine, beta lactam derivatives, beta-alethine. Perillyl alcohol, phenozenomycin, phenyl acetate, phosphatase inhibitors, picibanil, pilocarbine and salts or analogs thereof, pirarubucin, piritrexim, placetin A, placetin B, plasminogen activator inhibitor, platinum complex, phenyl ethyl isothiocyanate and analogs thereof, platinum compounds, platinum triamine complex, podophylotoxin, porfimer sodium, porphyromycin, propyl bis acridones, prostaglnadins J2, protease inhibitors, protein A based immune modulators, PKC inhibitors, microalgal, protein tyrosine phosphatase inhibitors, purine neucleoside phosphorylase inhibitors, purpurins, pyrazoloacridines, pyridoxylated haemoglobn polyoxyethylene conjugate, raf antagonists, raltitrexed, ramosetron, ras farnesyl protein tranaferase inhibitors, rasinhibitors, ras-GAP inhibitors, ratellitptine demethylated, Rhenium Re186 etidronate, rhizoxine, ribozyme, RII retinide, rogletimide, rosagliatazone and analogs and derivatives thereof, rohitukine, romurtide, roquinimex, rubiginone B1, ruboxyl, safingol, saintopin, SarCNU, sarcophytol A, sargrmostim, sdi 1 mimetics, semustine, senescence derived inhibitor 1, sense oligonucleotide, signal transduction inhibitors, signal transduction modulators, single chain antigen binding protein, sizofiran, sobuzoxane, sodium borocaptate, sodium phenyl acetate, solverol, somatomedin binding protein, sonermin, sparfosic acid, spicamycin D, spiromustin, splenopentine, spongistatin 1, squalamine, stem cell inhibitor, stem cell division inhibitor, stipiamide, stromelysin, sulfinosine, superactive vasoactive intestinal peptide antagonists, suradista, siramin, swainsonine, synthetic glycosaminoglycans, tallimustine, tamoxifen methiodide, tauromustine, tazarotene, tacogalan sodium, tegafur, tellurapyrilium, telomerase inhibitors, temoporfin, tmeozolomide, teniposide, tetrachlorodecaoxide, tetrazomine, thaliblastine, thalidomide, thiocoraline, thrombopoetin and mimetics thereof, thymalfasin, thymopoetin receptor agonist, thymotrinan, thyroid stimulating harmone, tin ethyl etiopurpin, tirapazamine, titanocene and salts thereof, topotecan, topsentin, toremifene, totipotent stem cell factors, translation inhibitors, tretinoin, triacetyluridine, tricribine, trimetrexate, triptorelin, tropisetron, turosteride, tyrosine kinase inhibitors, tyrphostins, UBC inhibitors, ubenimex, urogenital sinus derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozol, zanoterone, zeniplatin, zilascorb and zinostatin.

Other chemotherapeutic agents include: antiproliferative agents (e.g., piritrexim isothiocyanate), antiprostatic hypertrophy agents (sitogluside), Benign prostatic hyperplasia therapy agents (e.g., tomsulosine, RBX2258), prostate growth inhibitory agents (pentomone) and radioactive agents: Fibrinogen I125, fludeoxyglucose F18, Fluorodopa F18, Insulin I125, Iobenguane I123, Iodipamide sodium I131, Iodoantipyrine I131, Iodocholesterol I131, Iodopyracet I125, Iofetamine HCL I123, Iomethin I131, Iomethin I131, Iothalamate sodium I125, Iothalamate I131, Iotyrosine I131, Liothyronine I125, Merosproprol Hg197, Methyl iooodobenzo guanine (MIBG-I131 or MIBGI123) selenomethionine Se75, Technetium Tc99m furifosmin, technetium Tc99m gluceptate, Tc99m Biscisate, Tc99m disofenin, TC99m gluceptate, Tc99m lidofenin, Tc99m mebrofenin, Tc99m medronate and sodium salts thereof, Tc99m mertiatide, Tc99m oxidronate, Tc99m pentetate and salts thereof, Tc99m sestambi, Tc99m siboroxime, Tc99m succimer, Tc99m sulfur colloid, Tc 99m teboroxime, Tc 99m Tetrofosmin, Tc99m Tiatide, Thyroxine I125, Thyroxine I131, Tolpovidone I131, Triolein I125 and Treoline I125, and Treoline 131, MIBG-I123 and MIBG I131 are especially preferred chemotherapeutic agents for co-administration with the nitrofuran containing pharmaceutical composition of invention.

Another category of chemotherapeutic agents are anticancer supplementary potentiating agents, e.g., antidepressant drugs (Imipramine, desipramine, amitriptyline, clomipramine, trimipramine, doxepin, nortriptyline, protriptyline, amoxapine, and maprotiline), or no-trycyclic anti-depressant drugs (sertraline, trazodone and citalopram), Ca++ antagonists (verapamil, nifedipine, nitrendipine and caroverine), calmodulin inhibitors (prenylamine, trifluoperazine and clomipramine), Amphotericin B, Triparanol analogs (e.g., Tamoxifen), antiarrhythmic drugs (e.g., quinidine), antihypertensive drugs (e.g., reserpine), thiol depleters (e.g., buthionine and sulfoximine) and multiple drug resistance reducing agents such as Cremophor EL.

Another chemotherapeutic agents include: annoceous acetogenins, ascimicin, rolliniastatin, guanocone, squamocin, bullatacin, squamotacin, taxanes, baccatin. One important class of chemotherapeutic agents are taxanes (paclitaxel and docetaxel). The compounds of this invention in combination with tamoxifen and aromatase inhibitors arimidex (e.g., anastrazole) are particularly useful for treatment of cancers.

Another important class of molecules that is used to treat cancer in combination with compounds of this invention include but are not limited to anti-CD20 mAB, rituximab, Rituxan, Tositumoman, Bexxar, anti-HER2, Trastuzumab, Herceptin, MDX20, antiCA125 mAB, antiHE4 mAB, oregovomab mAB, B43.13 mAB, Ovarex, Breva-REX, AR54, GivaRex, ProstaRex mAB, MDX447, gemtuzumab ozoggamycin, Mylotarg, CMA-676, anti-CD33 mAB, anti-tissue factor protein, Sunol, IOR-C5, C5, anti-EGFR mAB, anti-IFR1R mAB, MDX-447, anti-17-1A mAB, edrecolomab mAB, Panorex, anti-CD20 mAB, (Y-90 lebelled), Ibritumomab Tiuxetan (IDEC-Y2B8), Zevalin, anti-Idiotypic mAB.

EXAMPLE 1

HE4 Over Expression Promotes Chemoresistance in Ovarian Cancer Cells

As described in detail below, patients with epithelial ovarian cancers have elevated serum levels of the biomarker HE4 (WFDC2). Described herein are experiments that measured HE4 production in ovarian cancer cell lines to establish stably transfected HE4 overexpressing ovarian cancer cell clones to determine putative cellular functions of this protein. HE4 production and secretion was measured by a non-competitive EIA assay. SKOV-3 cells were transfected with WFDC2/pCMV6 and cloned. HE4 expression was quantitated and growth and cell-cycle progression was analyzed along with cell viability when treated with chemotherapeutic agents. As described in detail below, HE4 overexpressing cell clones displayed a slightly higher growth rate and had a 7 to 16 fold increased expression of HE4 over that of their parental cell line. There were differences in cell-cycle progression (through S and G2/M phase) and regulator expression (cdc25, cdc2, CyclinB) compared with the parental cell line. HE4 over-expressing ovarian cancer cells displayed chemoresistance to cisplatin, paclitaxel, doxorubicin and camptothecin. The present study indicates that cellular functions of the biomarker HE4 are linked to the resistance of gynecological cancer cells to chemotherapeutic drugs.

Human epidymal secretory protein E4 (HE4), also called whey-acidic-protein (WAP), four-disulfide core domain protein 2 (WFDC2), or putative protease inhibitor WAP5, was initially found expressed in the epididymis. HE4 is also expressed in a limited number of other organs, including the female reproductive tract, breast tissue, kidney and regions of the respiratory tract and nasopharynx. Alternative splicing of HE4 can lead to 5 putative isoforms of this protein. HE4 in human ovarian cancer cells is produced as a ~13 kD protein and converted to a ~25 kD secreted glycosylated protein. Attention to the putative functions of HE4 arose with the discovery of HE4 overexpression in a subset of pulmonary tumor cell lines and in serous and endometrioid ovarian carcinomas. HE4 is located in the chromosomal region 20q13.12-13.1 which is frequently amplified in these gynecological cancers and has been developed as a biomarker for ovarian and endometrial cancer detection and management.

The majority of women with epithelial ovarian cancer (EOC) are diagnosed with advanced stage disease and have tumors that are initially sensitive to platinum chemotherapy. However, approximately twenty percent of EOC tumors are platinum resistant disease and most tumors will eventually develop chemoresistant cells. The treatment of patients with tumors resistant to cytotoxic agents presents a therapeutic challenge and requires a further understanding of the biochemical background of drug resistance and improvement of chemotherapeutic regimens. The molecular structure of EOC tumor marker HE4 suggests a biologic function for this protein. Therefore, the putative role of HE4 expression was investigated in ovarian cancer cells in vitro. SKOV-3 cells were stably transfected with an HE4 expressing integrative expression vector to determine if HE4 overexpression modulates cell growth and the response to chemotherapeutic drugs.

Cell Culture

Human cell lines SKOV-3 and CaOV-3 (ovarian epithelial adenocarcinoma), ECC-1 and AN3CA (endometrial adenocarcinoma), PC-3 (prostate adenocarcinoma), MCF-7 (breast adenocarcinoma), IMR-32 (neuroblastoma) and HK-2 (proximal tubular kidney cells) were obtained from American-Type-Culture-Collection (Manassas, Va.) and TCL-1 (immortalized trophoblasts) were provided by a colleague. Cells were grown in complete medium in T75 cell culture flasks (Corning, New York, N.Y.) according to the providers recommendations.

Calculation of Cellular HE4 Production

Cells were grown for 24 h in 100 mm cell culture dishes (Corning, New York, N.Y.), supernatant collected and lysates of washed and scraped cells prepared as described previously (Lange T S et al., 2007Chem Biol Drug Design, 70:302-10). Total protein of lysates was quantitated (BioRad protein estimation kit, Hercules, Calif.), and HE4 levels were determined using the HE4 EIA assay (Fujirebio Diagnostics, Malvern, Pa.), a solid-phase, non-competitive immunoassay using two mouse monoclonal antibodies, directed against two epitopes in the C-WFDC domain. Calibration curves were used to measure HE4 concentrations in both cell lysates and culture media allowing for the calculation of production and secretion of HE4 in pmol/g total cellular protein.

Cell Transfection

Figure 11:
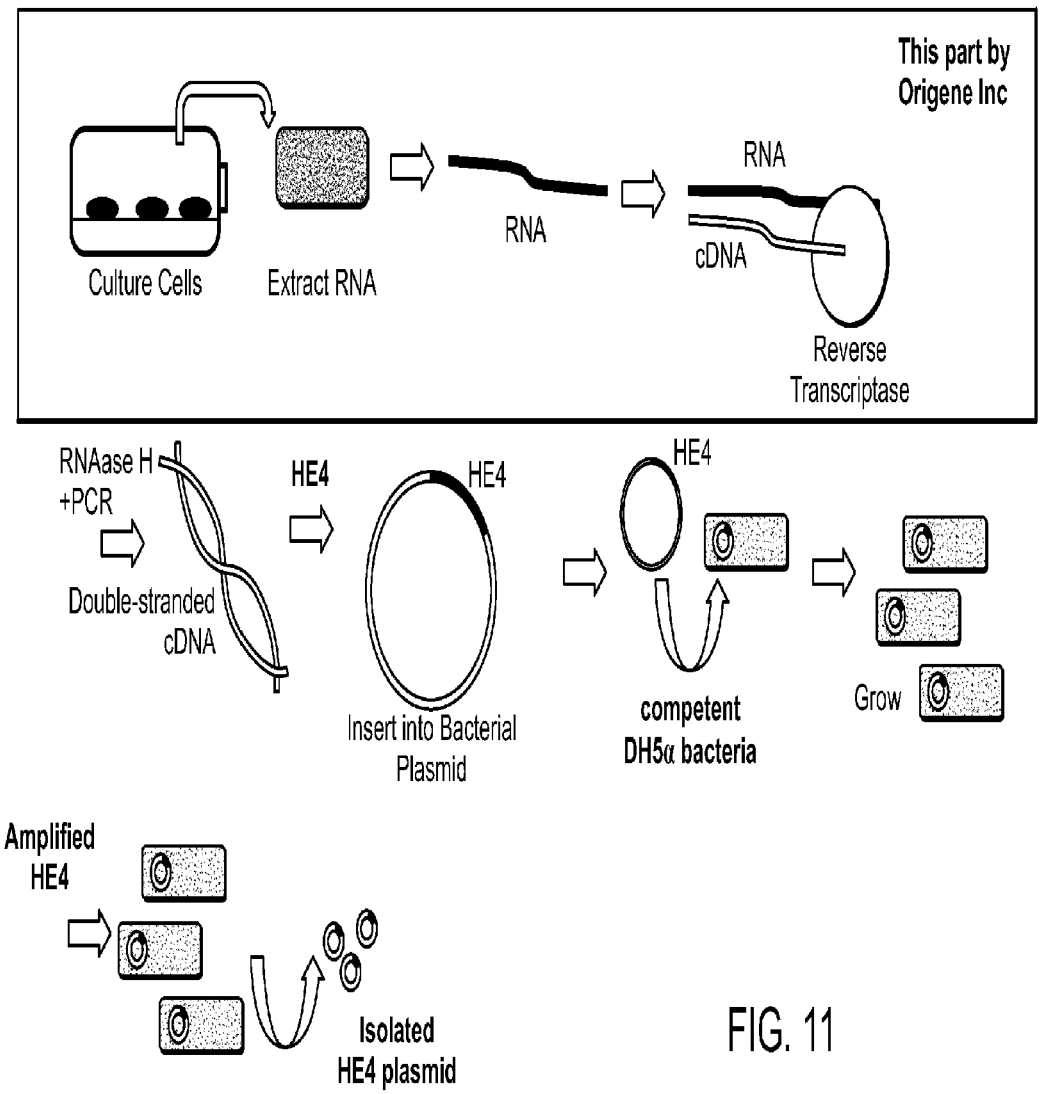
FIG. 11 is a schematic design of the amplification of the HE4 gene and isolation of HE4 cDNA.

A schematic design of the amplification of the HE4 gene and isolation of HE4 cDNA is shown in FIG. 11. An HE4 overexpressing vector for stable expression was engineered by inserting a coding sequence of human WAP four-disulfide core domain 2 (WFDC2) cDNA into a multiple cloning site of an eukaryotic expression vector, pCMV6-entry (Origene, Rockville, Md.). Transfection of the constructs in SKOV-3 cells was performed using Lipofectamine 2000 (Invitrogen, Carlsbad, Calif.) according to the manufacturer's instructions. Stably transfected cells were selected by resistance to G-418 (500 µg/ml) (Research Products International, Mount Prospect, Ill.), applied 48 h after transfection and continued during cell culture. G-418 resistant cells were resuspended (density 5 cells/ml) in complete medium/G-418 and seeded as 200 µl/well on a 96 well cell culture plate (Corning, New York, N.Y.). Cells growing from single colonies (cloned; stable transfection) were isolated.

RT-PCR

Total RNA isolation from cells was carried out using TRIzol and Reverse transcription on 3 µg RNA using SuperScript III transcriptase according to the manufacturers protocol (Invitrogen, Carlsbad, Calif.) followed by 30 cycles of PCR using the following primer pairs: HE4 sense, 5'-AGG AGC AGA GAA GAC TGG-3' (SEQ ID NO: 27); HE4 antisense, 5'-TTA TCA TTG GGC AGA GAG-3' (SEQ ID NO: 28); GAPDH sense, 5'-AAT CCC ATC ACC ATC TTC C-3' (SEQ ID NO: 29); GAPDH antisense, 5'-GTC CTT CCA CGA TAC CAA AG-3' (SEQ ID NO: 30). Cycle conditions: 94° C./1 min; 55° C./2 min, 72° C./2 min. PCR products were separated on 2% agarose gels containing 0.4 mg/ml of ethidium bromide.

MTS Assay

Cell growth and viability of cell lines (complete medium, 24 h incubation) was determined by the CellTiter 96® AQueous One Solution Assay (Promega Corp, Madison, Wis.) following the manufacturer's recommendations with modifications (Lange T S et al., 2008 PLOS One, 3(5): e2303). Experiments are expressed as the mean of triplicate determinations (X±SD) of a representative experiment in OD (cell growth) or % of absorbance by drug-treated versus untreated cells [=100%] (cell viability). Cisplatin (CDDP), paclitaxel, doxorubicin and camptothecin (CPT) were purchased from (Sigma Aldrich, St. Louis, Mo.).

Cell-cycle Analysis

Cell-cycle analysis was carried out by flow cytometry as described previously (Lange T S et al., 2008 PLOS One, 3(5):e2303), data were acquired on a BD FACSort flow cytometer using CellQuest software (BD Immunocytometry Systems, San Jose, Calif.) and analyzed by using ModFit LT software (Verity Software House, Inc., Topsham, Me.). Standardized gating was applied; $1\times10^4$ events were analyzed for each sample.

Western Blot Analysis

Preparation of cell lysates, PAGE and immunoblotting was carried out as described previously (Lange T S et al., 2007Chem Biol Drug Design, 70:302-10) in Cell Extraction Buffer (BioSource International, Inc., CA) supplemented with protease inhibitor cocktail and phenylmethylsulfonyl fluoride (Sigma-Aldrich, St. Louis, Mo.). Samples (50 µg/sample) were separated using the Xcell SureLock™ mini-cell electrophoresis system (Invitrogen, Carlsbad, Calif.) on NuPAGE® 4-12% Tris-Bis Gel in NuPAGE® MES SDS running buffer, transferred onto a PVDF membrane, blocked with 5% nonfat dry milk in PBS-Tween and probed against various primary antibodies (against cdc2 #9112, cyclinB1 #4138, cdk6 #3136—all from rabbit in a dilution of 1:1000, Cell Signaling Technologies, Danvers, Mass.; or against cdc25 sc#6946 from rabbit, GAPDH #sc-47724 from goat at a dilution 1:3000, Santacruz Biotechnology, Santa Cruz, Calif.). The bands were visualized using horseradish peroxidase-conjugated secondary antibody (Amersham-Pharmacia Biotech, Piscataway, N.J.), followed by enhanced chemiluminescence (Upstate, Waltham, Mass.) and documented by autoradiography (F-Bx810 Film, Phenix, Hayward, Calif.).

Figure 1B:
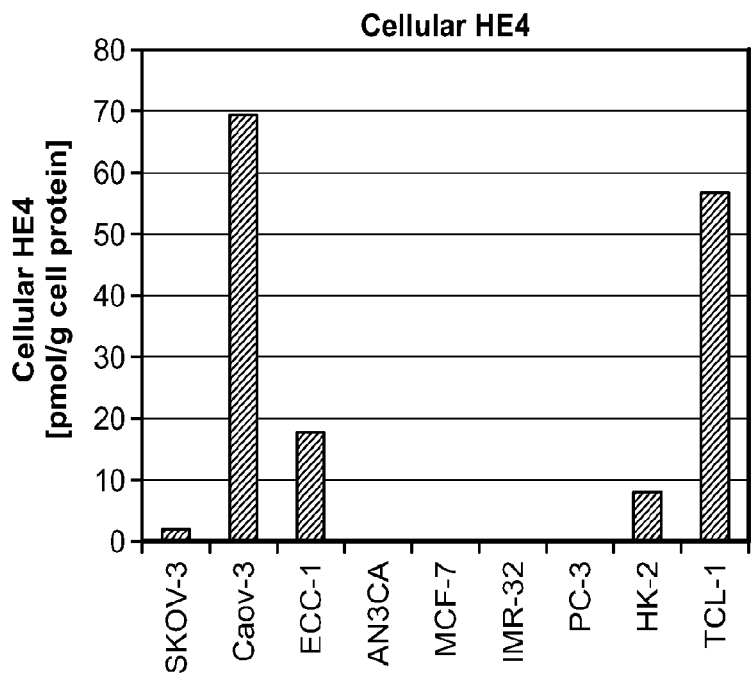
FIG. 1B shows HE4 concentrations in cellular lysates. Production and secretion of HE4 was calculated as pmol HE4/g total cellular protein. Comparative EIA analysis of the production and secretion of HE4 by SKOV-3 and CaOV-3 ovarian cancer cells, various human cancer cell lines from different tissues, normal HK-2 kidney cells and TCL-1 trophoblasts was carried out. Lysate and media of ovarian (SKOV-3, CaOV-3), endometrial (ECC-1, AN3CA), breast (MCF-7), neuroblastoma (IMR-32), prostate (PC-3) and human kidney (HK2) and third trimester trophoblasts (TC1-1) were assessed by HE4 sandwich ELISA. The values are normalized to unit protein concentration.

Comparative Analysis of HE4 Production and Secretion by Various Gynecological Cancer Cell Lines To determine the amount of HE4 produced and secreted by gynecological cancer cell lines in comparison to a panel of other cancer cells as well as normal cells known to express HE4 (HK-2, normal kidney) or non-malignant immortalized cells (TCL-1, trophoblasts) an EIA analysis was performed. FIG. 1 depicts the amounts of secreted HE4 (FIG. 1A) and in cellular lysates (FIG. 1B) of cells incubated for 24 h in complete medium (w/o FCS), calculated as mol HE4/g total cellular protein. PC-3 (prostate cancer), MCF-7 (breast cancer), IMR-32 (neuroblastoma) and AN3CA (poorly differentiated, steroid receptor defective serous type 2 endometrial carcinoma) did not produce detectable amounts of HE4. ECC-1 endometrial cancer cells (differentiated, steroid-responsive) expressed and secreted high amounts of HE4 (lysate: 18 pmol HE4/g protein, secreted: 187 pmol/g protein). Significant HE4 amounts were detected for SKOV-3 (lysate: 2 pmol HE4/g protein, secreted: 53 pmol/g protein) and high amounts for CaOV-3 (lysate: 69 pmol HE4/g protein, secreted: 870 pmol/g protein) ovarian cancer cell lines. HE4 production by HK-2 cells was significant (lysate: 8.1 pmol HE4/g protein, secreted: 113 pmol HE4/g protein) and TCL-1 cells produced remarkably high HE4 levels (lysate: 57 pmol HE4/g protein, secreted: 438 pmol/g protein).

Figure 2A:
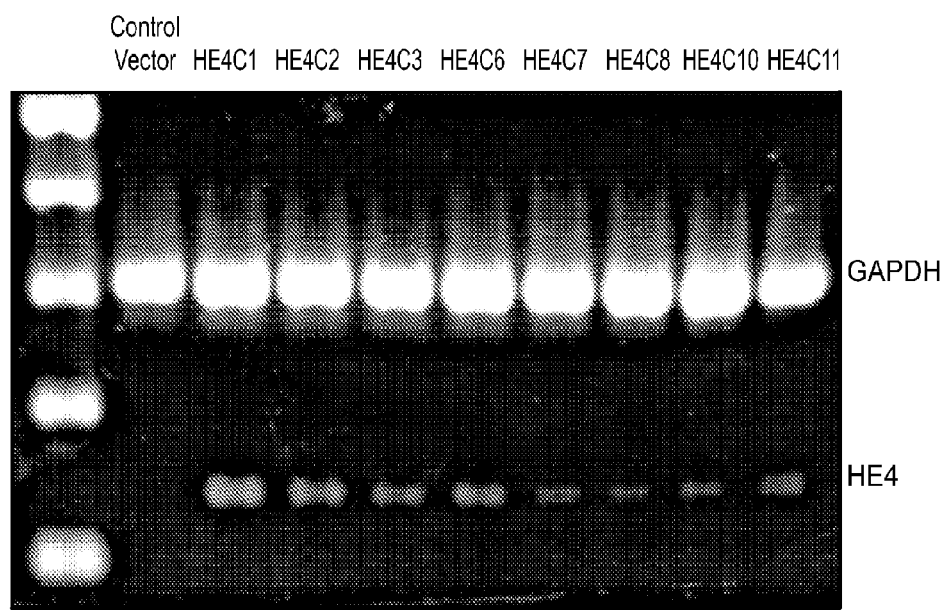
In FIG. 2A, SKOV-3 cells were transfected with eukaryotic expression vector pCMV6 carrying the coding sequence of human HE4, cloned, and the expression of HE4 determined by semiquantitative RT-PCR along with GAPDH expression as control.

Cloning, Growth and Cell-cycle Progression of WFDC2/pCMV6 Transfected (HE4 Overexpressing) SKOV-3 Cells SKOV-3 cells were transfected with expression vector pCMV6 carrying the coding sequence of human HE4 and were cultured under selective antibiotic pressure and cloned. The expression of HE4 along with GAPDH expression as a control was determined by semiquantitative RT-PCR for a panel of clones (FIG. 2A). The PCR conditions were established to reveal differences in the HE4 expression levels between clones. Three clones that presented a high (HE4C1), moderate (HE4C3), and low level (HE4C7) of HE4 overexpression were evaluated further.

Figure 2B:
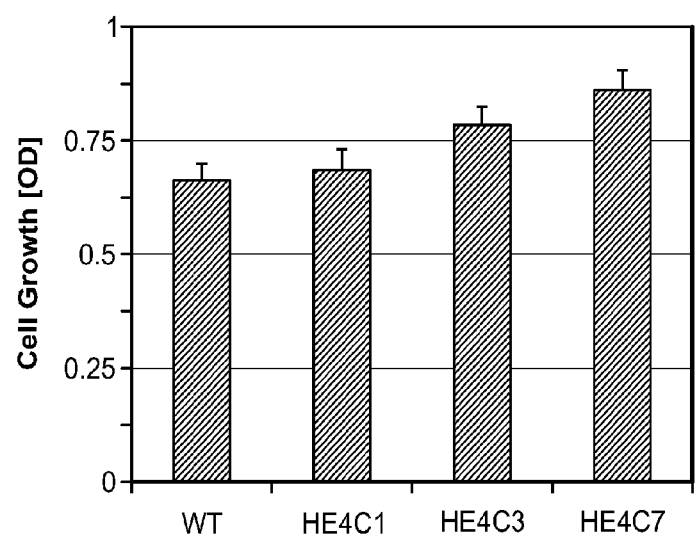
In FIG. 2B, growth of HE4 overexpressing SKOV-3 clones HE4C1, -C3, -C7 in comparison to parental/wild type (WT) cells was determined in an MTS assay. Experiments are expressed as the mean of triplicate determinations (X±SD) of a representative experiment in OD.
Figure 3A:
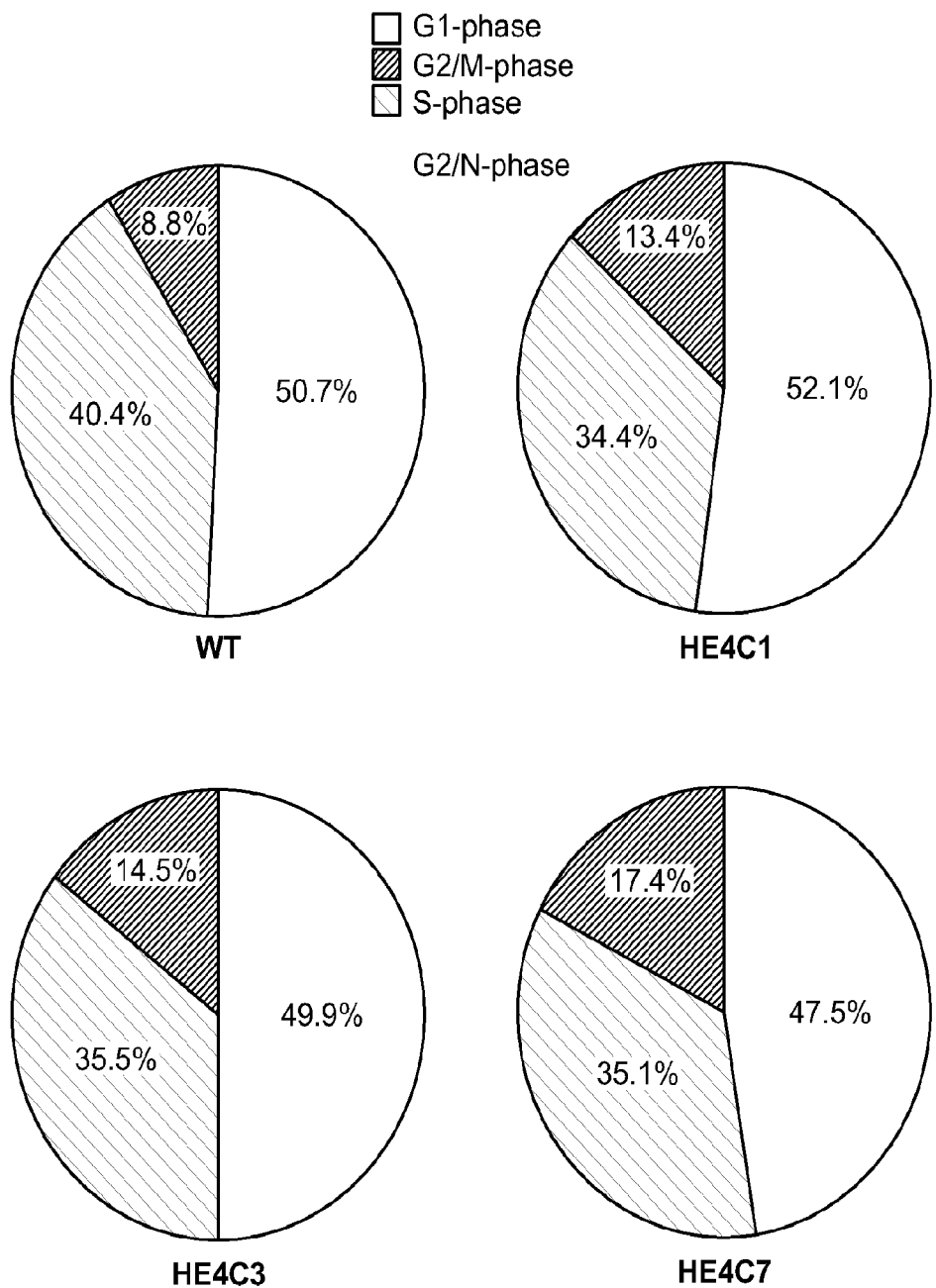
FIG. 3 is a series of pie charts, line graphs, and photomicrographs illustrating cell-cycle analysis of HE4 overexpressing SKOV-3 ovarian cancer cells. Cell-cycle analysis of HE4 overexpressing SKOV-3 cell clones in comparison to WT cells was carried out by flow cytometry, standardized gating was applied, $1 \times 10^4$ events were analyzed for each sample. Data are presented in % of cells in a diagram in FIG. 3A or as the relative fluorescence intensity of cell subpopulations in the 2-dimensional FACS-profile in FIG. 3B.
FIG. 3C shows the analysis of cell-cycle regulators in cell lysates of HE4 overexpressing SKOV-3 cell clones. Analysis was carried out by PAGE and Western Blot analysis with suiting primary antibodies. As an internal standard for equal loading the blots were probed with an anti-GAPDH antibody.
Figure 3B:
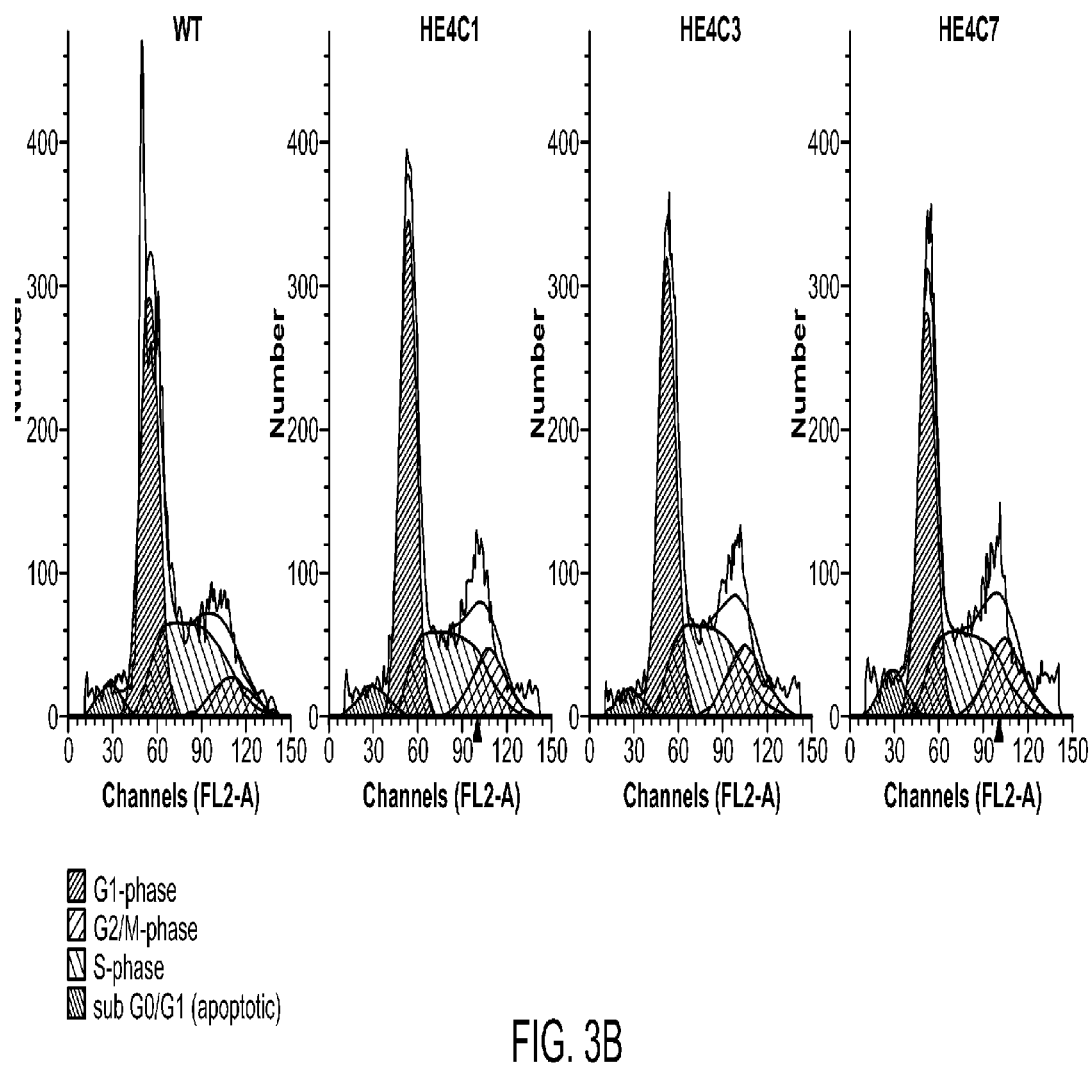
Figure 3C:
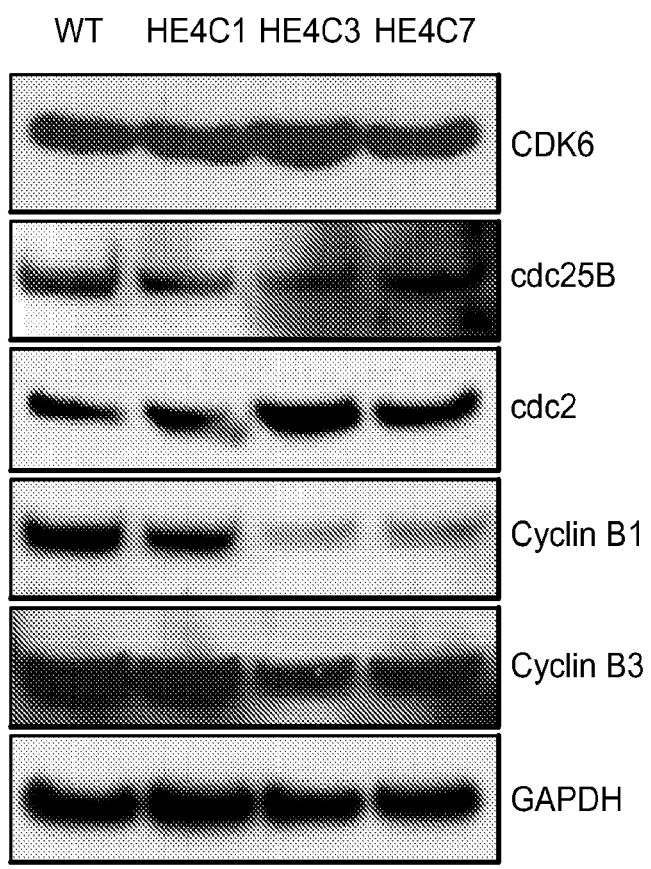

Comparison of the cell growth of HE4 over-expressing versus parental SKOV-3 cells was conducted by a MTS viability assay and by flow cytometry analysis. HE4C1, -3 and -7 as well as other clones consistently presented a slightly higher growth rate as compared to the parental cells, reflected by a higher optical density after seeding an equal number of cells and 24 h culture (FIG. 2B). No correlation was seen between altered growth and level of HE4 overexpression. For example, HE4C1 displayed a similar growth, yet had the highest level of HE4 expression when compared to parental/wild type SKOV-3 cells. Similarly, flow cytometry analysis revealed a comparable profile of cell-cycle phases for clones and parental cells as presented by percentage of cells in a given sub-population (diagram, FIG. 3A) or as the relative fluorescence intensity (2-dimensional FACS-profile, FIG. 3B). Some differences were seen in progression of clones through the S phase (4.9-6.0% less counts than parental SKOV-3) and G2/M phase (4.6-8.6% more counts). Analysis of cell-cycle regulators in cell lysates of HE4 overexpressing SKOV-3 cell clones was carried out by Western Blot analysis. Significant differences were not observed between clones and parental cells in the expression of CDK6, a member of the cyclin-dependent protein kinase (CDK) family that is essential for G1 progression and G1/S transition. By contrast, changes in the expression of cdc2, cdc25B and Cyclin B1 and -3 which are all essential for G2 progression and G2/M transitions were observed. Cdc25B was downregulated and cdc2 upregulated in all three clones analyzed. Cyclin B1 was strongly and cyclin B3 slightly downregulated in all clones as compared to the expression in the parental SKOV-3 cells (FIG. 3C). The observed effects on cell cycle regulators cdc2, cdc 25B, cyclin B1 and -B2 were less prominent for HE4C1 with the highest level of HE4 expression when compared to HE4C3, and HE4C7. In summary, stable transfection of SKOV-3 cells with WFDC2/pCMV6 did result in a slightly higher growth rate and changes in the expression of cell cycle regulators implicated in G2/M transition.

Figure 4A:
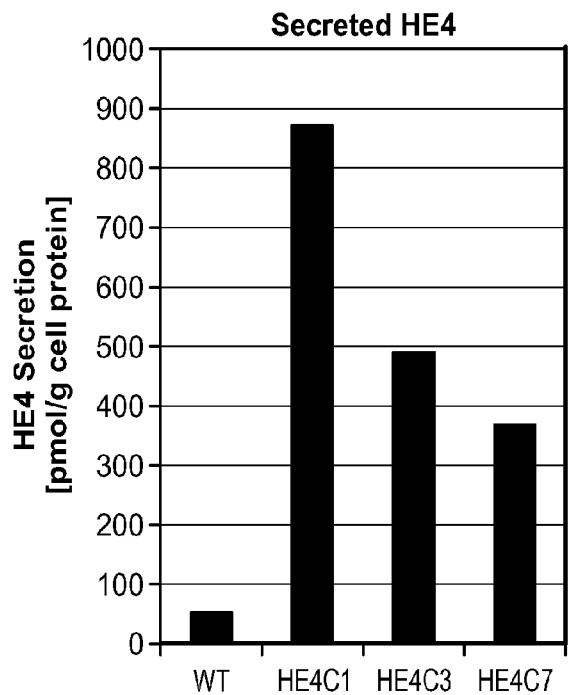
FIG. 4A shows HE4 amounts in supernatants.
Figure 4B:
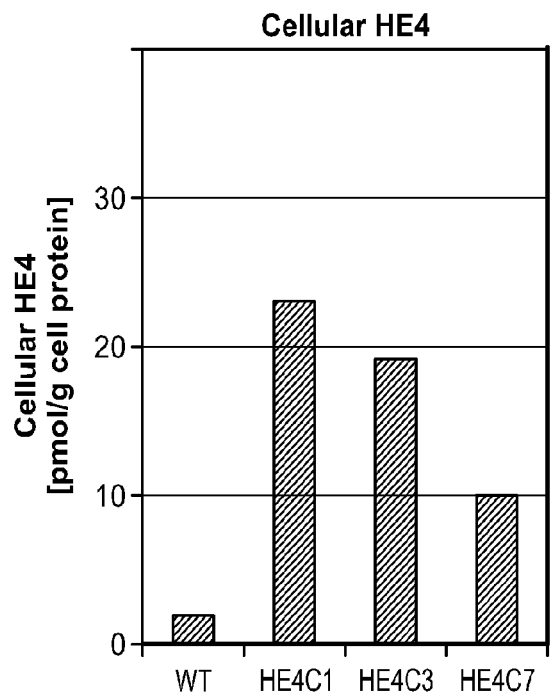
FIG. 4B shows HE4 amounts in cellular lysates. Data are presented as pmol HE4/g total cellular protein.
Figure 5A:
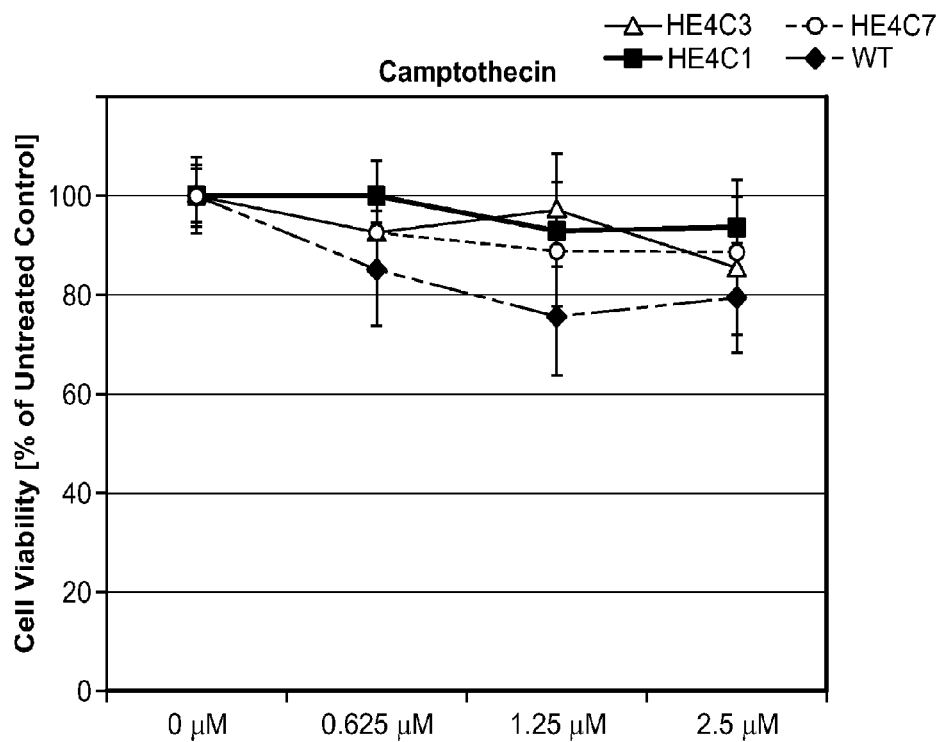
FIG. 5 is a series of line graphs showing decreased sensitivity of HE4 over-expressing ovarian cancer cells to chemotherapeutic drugs. Wild-type SKOV-3 or HE4 overexpressing clones HE4C1, -C3, -C7 were treated with camptothecin (FIG. 5A), paclitaxel (FIG. 5B), cisplatin (FIG. 5C) or doxorubicin (FIG. 5D) for 24 h in concentrations as indicated and the cell viability evaluated in an MTS assay Data are expressed as the mean of the triplicate determinations (X±SD) compared to untreated cells [=100%].
Figure 5B:
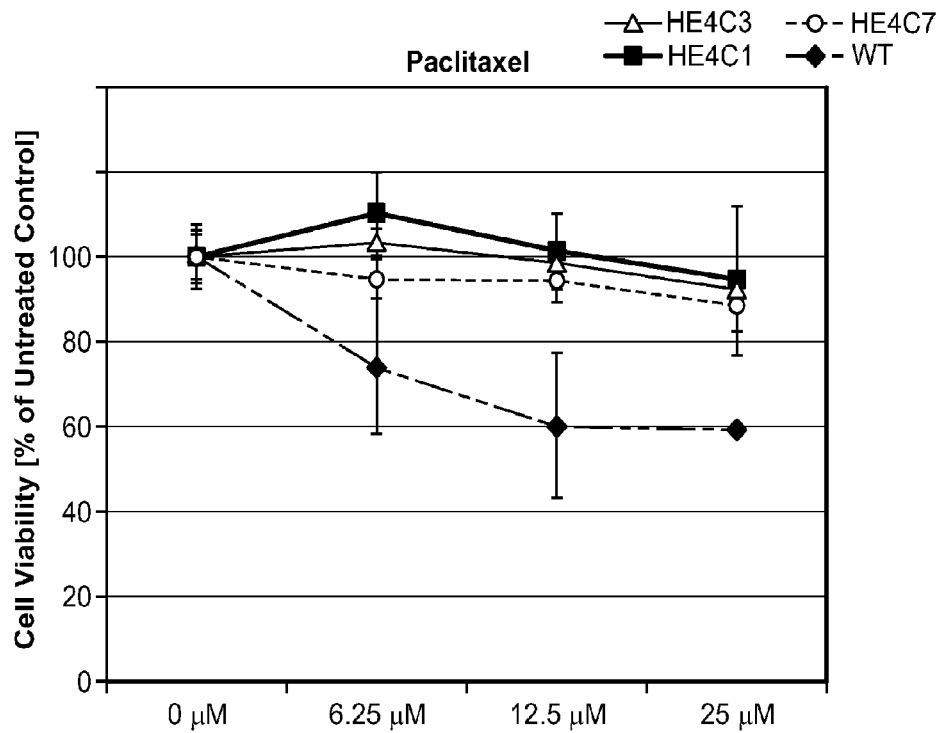
Figure 5C:
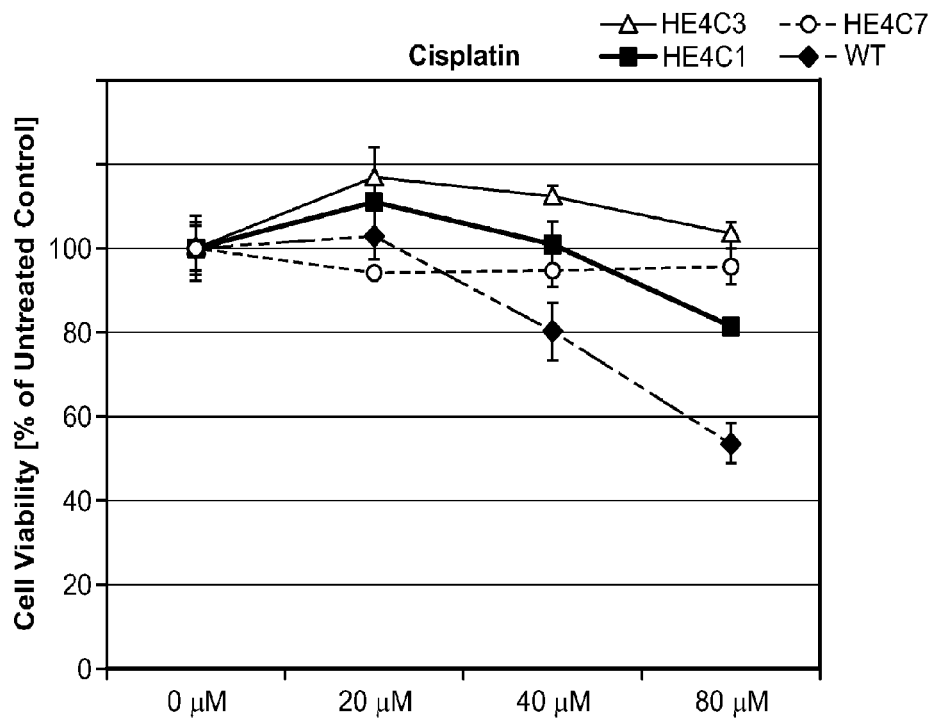
Figure 5D:
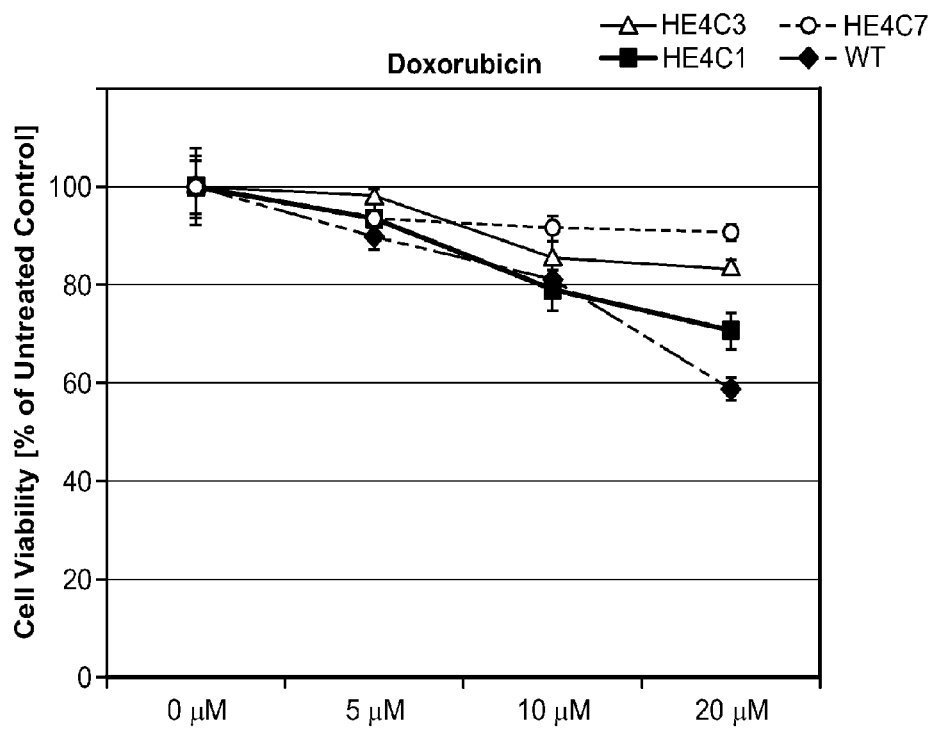

Stable Transfected SKOV-3 Cell Clones Display Increased HE4 Production and Decreased Sensitivity to Cisplatin, Paclitaxel, Doxorubicin and Camptothecin The production and secretion of HE4 by SKOV-3 clones HE4C1, -C3, -C7 was measured by comparative EIA analysis. Depending on the clone studied the amount of secreted HE4 in 24 h was 7 to 16 fold (FIG. 4A) and the cellular amount of HE4 was 6 to 12 fold (FIG. 4B) elevated as compared to the parental cell line. Wild-type cells produced a total of 55 pmol HE4 and HE4C1 cells 895 pmol HE4 per gram total cellular protein (He4C3: 510 pmol HE4/g protein; HE4C7 382 pmol HE4/g protein).

To analyze the potential biological relevance of elevated HE4 production for ovarian cancer cells the efficacy of commonly used anticancer drugs was examined in a viability assay (FIG. 5). SKOV-3 clones or parental cells were treated with cisplatin, paclitaxel, doxorubicin, or camptothecin for 24 h in various concentrations as indicated and the cytotoxicity evaluated. For camptothecin at all concentrations tested (0.625, 1.25, 2.5 µM) wild-type cells consistently displayed a lower viability than HE4C1, -3, and -7 even though the maximum difference observed (at 1.2 µM) did not exceed 21% (FIG. 5A). Treatment with 6.25, 12.5 or 25 nM paclitaxel or 40 or 80 µM cisplatin reduced the viability of wild-type SKOV-3 cells drastically. In contrast, the three HE4 overexpressing clones examined did not display a significantly altered viability after paclitaxel treatment (FIG. 5B). Similarly, two clones did not respond to cisplatin treatment and one clone (HE4C1) displayed minor sensitivity to cisplatin only at a higher drug concentration (80 µM) (FIG. 5C). A difference in the response of parental SKOV-3 versus HE4 overexpressing clones was also observed after treatment with 20 µM doxorubicin (wild-type: 58%, HE4C1 70%, HE4C3 84%, HE4C7 91% viability) (FIG. 5D). As for cisplatin, the clone with the highest HE4 production (HE4C1) displayed a greater response to doxorubicin (at 20 µM) than the other two clones tested. Thus, no clear correlation was seen between the degree of desensitization to a drug and the absolute level of HE4 production. However, all tested clones produced at least a 7 fold higher amount of HE4 than the parental cell line and all tested clones displayed a reduced sensitivity to all drugs tested.

The present reports describes the correlation of the overexpression of the human epididymal secretory protein 4 (HE4) by ovarian cancer cells with an increased resistance to chemotherapeutic drugs. To establish stably transfected ovarian cancer cell lines that overexpress HE4, platinum resistant SKOV-3 cells were utilized as model system since their basal expression level is moderate, as determined by EIA analysis (present report) and indicated by RT-PCR analysis on a panel of ovarian cancer cell lines. To examine the response of HE4 overexpressing SKOV-3 clones to anticancer drugs cisplatin, paclitaxel, doxorubicin and camptothecin were utilized. These common anticancer drugs are used to treat a variety of malignancies including EOC and endometrial cancers.

The efficacy of cisplatin and paclitaxel in HE4 overexpressing ovarian cancer cells was reduced when compared to drug cytotoxicity in the parental cell line. To a lesser extent and depending on the drug concentration, HE4 overexpressing SKOV-3 clones also displayed a reduced response to doxorubicin and camptothecin. This desensitization to all drugs tested occurred in all clones producing at least a 7 fold higher amount of HE4 than the parental cell line. High HE4 serum levels (>150 pM) are observed in a subset of endometrial cancer, in a significant number of breast cancer, and in most ovarian cancer patients with levels often exceeding 500 pM (Moore R G et al., 2009 Gynecol Oncol, 112:40-6; Moore R G et al., 2008 Gynecol Oncol; 110:196-201). For endometrial cancer it has been shown that high HE4 levels are correlated with an aggressive phenotype of the disease (Bignotti E et al., 2011 Br J Cancer, 104:1418-25).

The present report also reveals that HE4 overexpressing SKOV-3 cell clones displayed differences in cell-cycle progression through S phase and G2/M phase. Changes in the expression of cyclin B1, -B3, cdc25B, and cdc2 were observed. Cdc25 proteins control progression through S and predominantly G2 phase by activation of CDKs and of cdc2. The timing of the following entry into the mitosis entry depends on the regulation of cyclin B/cdc2. The observation that HE4 overexpression in SKOV-3 cancer cells affected regulators of the cell-cycle machinery might be of significance for treatment options. In general, cancer cells feature alterations in cell-cycle regulation and targeting checkpoints has been suggested as an supplemental approach to anticancer therapies (Kristjánsdóttir K, et al., 2004 Chem Biol, 11:1043-51; Hartwell L H and Kastan M B, 1994 Science, 266:1821-8). For example, the analysis of ovarian tissues revealed a high expression of cdc25 and cdc2 in tumors and tumorigenic ovarian cancer cell lines (D'Andrilli G et al., 2004 Clin Cancer Res, 10:8132-41). Moreover, cdc25 expression is correlated to an unfavorable outcome in a large number of ovarian cancer patients (Broggini M et al., 2000 Anticancer Res, 20:4835-40) and serves as a candidate for therapeutic molecular targeting. Taken together, these observations and the studies suggest that targeting key regulators of cell cycle progression might especially benefit in the treatment of tumors with high HE4 production.

Growth factors such as the epidermal growth factor (EGF), insulin growth factor (IGF) and vascular endothelial growth factor (VEGF) constitute principal growth-promoting signals in ovarian cancer cells and targeting their signaling is a promising approach to treat ovarian tumors. EGF receptor (EGFR) overexpression is associated with resistance to chemotherapy and in pre-clinical models and clinical trials EGFR inhibitors revealed efficacy especially in platinum-resistant settings. In preliminary studies, changes are observed in the expression of various cell signaling factors in HE4 over-expressing ovarian cancer cell clones such as a constitutive increase of the epidermal growth factor (EGF)-, insulin growth factor (IGF)- and in some cell clones of the vascular endothelial growth factor (VEGF) receptor activation/phosphorylation. If the HE4 production and growth signaling in ovarian cancer cells is bilaterally linked, then growth factor receptor targeting is a promising supplementary treatment option, especially for cancer patients with high HE4 production. Three whey-acidic-protein genes products (HE4, SLPI, Elafin) are overexpressed and secreted by ovarian tumors, and a recent study suggested that Elafin production is not only correlated with poor survival but can be enhanced by cytokine activity via activation of the nuclear factor kappaB pathway (Clauss A, et al., 2010 Neoplasia, 12:161-72).

Based on the data described herein, whey-acidic-proteins such as HE4 feature biological functions with a significant role in cancer progression and drug resistance. The present study indicates that cellular functions of HE4 are linked to the resistance of gynecological cancer cells to chemotherapeutic drugs. The therapy of gynecological cancer patients presenting high levels of HE4 is optimized when cellular targets of this protein are defined and functions can be blocked.

EXAMPLE 2

The Cause and Impact of HE4 Overexpression in Oncogenesis and Chemoresistance of Epithelial Ovarian Cancer (EOC) in Animal Models and Human Patients The biomarker HE4 (WFDC2) is highly over-expressed in the epithelial ovarian cancer (EOC). Serum HE4 levels was shown as a sensitive marker for differentiating malignant pelvic masses from benign neoplasms. Recently, the FDA approved HE4 as a biomarker for the early detection and monitoring of ovarian cancer. Prior to the invention described herein, the biological effects HE4 overexpression has on ovarian cancer development, chemoresistance and overall survival (OS) rate or disease free survival (DSF) rate was unknown.

As described herein, to study the functional impact of HE4 overexpression in EOC, a panel of stable HE4 overexpressing ovarian cancer cell lines was cloned with differential HE4 secretion and cellular production levels. The HE4 over-expressing clones showed significantly reduced efficacy response against Taxol, Cisplatin, Doxorubicin and Camptothecin in-vitro indicating that HE4 overexpression in ovarian cancer cells can promote chemoresistance against drugs targeting DNA chelation, tubulin and topoisomerase targets. Moreover, HE4 overexpressing clones displayed a highly aggressive phenotype of ovarian cancer with enhanced activation of Epidermal Growth Factor Receptor (EGFR), Insulin-like Growth Factor Receptor (IGF1R), Phosphoinositide-3kinase(PI-3K)/AKT and Bcl2 family oncogenes that promote chemoresistant ovarian cancer cells. On the other hand, lethal levels of HE4 production via pCMV6-HE4 vector suppressed ovarian and endometrial cancer cells proliferation and caused strong apoptosis, MAP Kinase activation and cell cycle arrest in SKOV-3 cells and revealed downregulation of oncogenic Bcl2, EGFR/PI-3K/AKT oncogenic proteins. Similarly, exogenous recombinant HE4 caused cytotoxicity to SKOV-3 cells and enhanced cisplatin response. The dichotomous dual functions of HE4 offers unique opportunity to unravel the ovarian cancer pathogenesis impacted by HE4 overexpression to optimize ovarian cancer chemotherapy outcome by identifying pharmacologic inhibitors and neutralizing HE4 antibodies or targeted HE4 genomic activation alone or in combination with standard chemotherapeutics or multi-modal treatment regimens.

Each year in the United States approximately 22,000 women are diagnosed with epithelial ovarian cancer (EOC) resulting in over 15,000 deaths annually. Prior to the invention described herein, there were no effective screening strategies to detect EOC in the early stages, and the absence of symptoms results in the majority of women being diagnosed with advanced stage disease at stages which are fundamentally incurable. Although current chemotherapy regimens have increased the 5 year survival rate to 40 to 50% the overall cure rate remains unchanged. Prior to the invention described herein, the surveillance of women with EOC to detect early recurrence of disease includes frequent clinical exams, monitoring biomarkers such as CA125 and HE4 and imaging. Women diagnosed with recurrent disease within the first six months of completing primary chemotherapy by definition present platinum resistant disease and have decreased responses to further chemotherapy.

Eventually, the majority of EOC patients will develop chemorefractory disease and ultimately succumbing to their disease. Thus, there is an urgent need for the development of novel therapeutic agents, drug responsive molecular targets, biomarkers, and gene therapy approaches to improve the outcome of therapy and overall survival for EOC patients.

HE4 is a Biomarker that is Overexpressed in Early and Late Stage EOC

Normal surface epithelium of the ovary does not express the HE4 protein, but is abundantly expressed in various histologic subtypes of EOC including 93% serous, 100% endometrioid and 50% of clear cell tumors. Elevated levels of the HE4 protein have been detected in the serum of women with EOC. Recently, the combination of HE4 and CA125 has been shown to differentiate benign ovarian cysts or pelvic masses from malignant ones with high sensitivities and specificity. HE4 is often not elevated in the benign gynecologic neoplasms when compared to serum CA125 and can differentiate endometriomas from malignant ovarian tumors. In patients with endometrial malignancies, HE4 overexpression correlated with aggressive malignancies and poor survival, HE4 overexpression has also been shown to be associated with lymph node metastasis, and lowered disease free survival in patients with breast cancer and pulmonary cancers.

HE4 Expression is Enriched in Inflammatory or Injury Prone Tissues in Humans

In contrast to HE4 overexpression in ovarian cancer, HE4 is not expressed in normal ovarian surface epithelium, early or late corpus luteum and fallopian tube epithelium. Notably, HE4 is expressed in a number of normal human tissues including the male epididymis, lung, respiratory tract, nasal and oral epithelium, and is highly enriched in saliva. HE4 is elevated in wounds and protects from inflammatory conditions. HE4 functions in the host defense mechanism of the respiratory tract and altered expression of HE4 may influence host defense capabilities of the ovarian surface epithelium, a common site of periodic injury and inflammation directly linked with ovarian cancer etiology. The presence of several inflammatory responsive elements including NFkB, Ikaros and LYF-1 in the HE4 promoter region and the upregulation of NFkB in ovarian cancer and its role in chemoresistance cells supports the potential impact of HE4 in the onset of ovarian cancer.

HE4 Overexpression is Related to Decreased Survival of High Expressor Patients

Elevated HE4 expression is linked to reduced survival among endometrial, breast and pulmonary cancer patients. The five-year disease-free survival in HE4-positive breast cancer patients was significantly lower (58.6%) than in the HE4 negative group (85.6%, p=0.04) and HE4 overexpressor patients showed significantly higher rates of metastasis.

Similarly, HE4 expression is associated with a worse prognosis of lung adenocarcinomas in which the five-year disease-free survival in the HE4-positive group was significantly lower (44.6%) than in the HE4 negative group (82.3%, p=0.001). The five-year overall survival rate was 60.1% in the HE4-positive group compared with 90.8% in the HE4-negative group (p=0.001). Even though HE4 is overexpressed in 93% of serous, 100% of endometrioid epithelial ovarian cancers, and 50% of clear cell (not mucinous) ovarian carcinomas, the disease free or overall survival rate of HE4 overexpressor versus HE4 non-expressor ovarian cancer population is not known.

Rationale for Targeting HE4 to Optimize Chemotherapy Response in Ovarian Cancer

In the U.S., one in 70 women is likely to be diagnosed with EOC. EOC has the highest mortality rate of all gynecologic malignancies with five year survival rates below fifty percent. Unfortunately the majority of women with EOC will eventually develop chemoresistant tumor and ultimately succumb to their disease. For these reasons, the development of targeted therapies and novel biologics for the treatment of this disease are desperately need.

HE4 is a Potential Immunotherapeutic or Pharmacological Target

Figure 8:
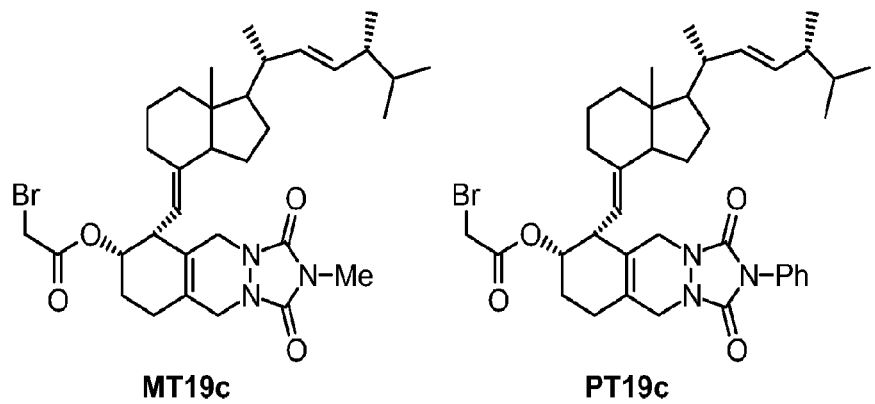
FIG. 8 is a series of chemical structures and a bar chart demonstrating that the impact of HE4 overexpression significantly sensitized the SKOV-3 clones to MT19c treatment. The HE4 over-expressor SKOV-3 clones showed 4 fold or higher response to MT19c treatment compared to parental SKOV-3 cells.
Figure 8:
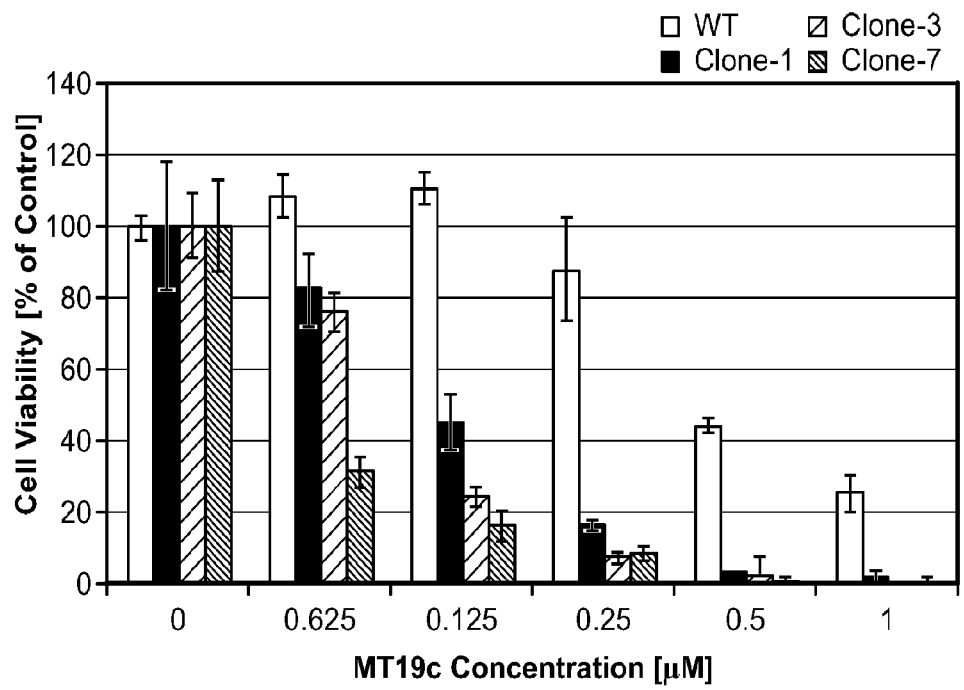

Studies examining gene expression array of ovarian tumors identified HE4 as a potential immunotherapeutic or pharmacological target. Targeting HE4 either through targeted immunotherapeutics or via a specific pharmacologic HE4 inhibitor significantly enhances the efficacy of chemotherapy or on their own be an effective treatment agent for ovarian cancer patients. Such immunotherapeutics or pharmacologic HE4 inhibitors/modulators may be designed de novo or identified from existing library screenings. As a proof, a limited in-vitro cell viability based screening of a library of anticancer agents against HE4 overexpressor ovarian cancer cells identified MT19c and PT19c as HE4 inhibitors. While 7 standard anticancer agents including cisplatin, Taxol, Adriamycin, etoposide and camptothecin lost efficacy up to 4-8 fold due to HE4 overexpression in SKOV-3 cells (FIGS. 2, 4, and 5), it was observed that HE4 overexpressing cells displayed (<4-8 fold) enhanced response to MT19c and PT19c treatment (FIG. 8). Prior to the invention described herein, the cause of enhanced response of HE4 overexpressor ovarian cancer cells to novel vitamin-d derivatives (HE4) was unknown. HE4 overexpressing clones exhibited a muted response to the cytotoxic agents compared to parental cells. The experiments described herein aim to determine if MT19c or PT19c is a specific inhibitor or modulator of HE4 or related signaling cascade in ovarian cancer cells. Based on the data, MT19c treats HE4 overexpressing EOC tumors, and acts as a pathway modulator to enhance the efficacy of clinically used drugs in EOC (cisplatin, Taxol, doxorubicin or camptothecin and etoposide) by counteracting the HE4 induced chemoresistance and promotion of EOC to improve the survival rate in ovarian cancer patients.

HE4 is Associated with Aggressive Phenotypes of Ovarian Cancer and Promotes Chemoresistance Described herein are results that reveal how HE4 overexpression contributes to aggressive phenotypes of EOC and promotes chemoresistance against chemotherapeutics in ovarian cancer. The biological functions and impact of HE4 overexpression on ovarian cancer oncogenesis, signaling pathways and chemoresistance have not been studied to date. As described herein, HE4 overexpression evolves a highly aggressive phenotype of ovarian cancer cells that are highly chemoresistant to the treatment of Cisplatin, Taxol, Doxorubicin and camptothecin. Unfortunately, current chemotherapy regimens are centered around these drugs that target tubulin, topoisomerase enzymes or cause DNA damage or chelation and HE4 overexpression muted these therapeutic targets. As described herein, HE4 induced enhanced chemoresistance partly due to higher constitutive activation of oncogenes or growth factor receptors such as EGFR, IGF1R, PI3K/AKT, BCl2 family proteins when compared to parental ovarian cancer cells. These factors alone or together with increased expression of DNA repair genes, multi-drug resistant (MDR) proteins, EGFR/PI-3K pathway, p53 status and regulation of NFκB promote ovarian cancer chemoresistance especially to cisplatin. The presence of several inflammatory responsive elements (NF-kB, Ikaros, LYF-1) in the HE4 promoter and participation of NF-kB in platinum chemoresistance indicates the existence of intricate role of HE4 in chemoresistance and progression of ovarian cancer.

HE4 is a Potential Genomic Therapy Tool for the Treatment of Ovarian Cancer

Based on high constitutive and localized HE4 transcriptional activity, HE4 promoter (e.g., pHE4-652) selectively activates reporter gene expression with minimum vector concentration and toxicity in an ovarian cancer specific manner. Several candidate promoters have been used to control therapeutic gene expression in ovarian cancer cells. The human chorionic gonadotropin (hCG) promoter subcloned upstream of diphtheria toxin-A chain gene in a retrovirus, showed selective killing of ovarian cancer cell lines with minimal toxicity to normal ovary and fibroblasts. Similarly, serine leukocyte protease inhibitor-1 (SLP1) promoter that drove herpes simplex virus thymidine kinase (HSVTK) in SKOV-3 cells and cancer-specific telomerase gene promoter (human telomerase reverse transcriptase, hTERT) have been examined as gene therapies for ovarian cancer.

Production of High Levels of HE4 Causes Selective Cell Death and Apoptosis in Ovarian Cancer Cells.

Ovarian cancer cells can be induced to produce lethal levels of HE4 production beyond a threshold HE4 level via a transient transfection with overexpression vector (pCMV6-HE4, Origene Inc) or an inducible vector (pTRE-hyg-HE4) under antibiotic control. Notably, the tolerable threshold for HE4 levels varies significantly among the cell phenotypes and source of the cell. For example, EOC SKOV-3 cells and endometrial (ECC-1 cells) showed significant cell death, apoptosis, inhibition of cell cycle arrest and activation of MAP kinases and downregulation of BCl2 family proteins within 24 hrs when lethal levels of HE4 production was induced via a pCMV6-HE4 overexpression vector compared to parental control. Under similar conditions, non-transformed cells (HK-2) were not affected. Moreover, the exogenous recombinant HE4 also showed significant cytotoxicity to ovarian cancer cell-lines. To test the potential of genomic activation via production of lethal cellular levels of HE4 in animals an inducible vector (pTRE-hyg) incorporating HE4 gene in multi-cloning site, under doxycycline negative control has been ligated in SKOV-3 cells. This indicates that progression of the tumors in the pTRE-hyg-HE4 versus pTRE-hyg or parental control can be suppressed.

The invention described herein quantitates the impact of HE4 in the progression and chemoresistance profile of EOC in cultured cell, animal or human patient models, based on the observation that HE4 overexpression caused chemoresistance against cisplatin, Taxol, doxorubicin or camptothecin. As described herein, biologics or immunotherapeutic HE4 modulators (e.g., inhibitor) that may act on their own or as sensitizers to improve the efficacy of cytotoxic chemotherapeutics in EOC patients.

The data described herein provides primary mechanistic evidences that HE4 expression awarded chemoresistance and significantly muted the cytotoxic effects of cisplatin, Taxol, doxorubicin, camptothecin in SKOV-3 cell lines. Based on the study, innovative biologics (small molecule, pharmacologic inhibitors, immunotherapeutic agents or neutralizing antibodies) can now be designed/developed to suppress HE4 induced chemoresistance in EOC patients. As an example, it was demonstrated that the molecule MT19c had a 4-8 fold increase in cytotoxicity in HE4 overexpressing cell line clones as compared to the parental SKOV-3 (FIG. 3). Furthermore, the genomic analysis and the response of xenografts of stably overexpressing HE4 clones versus the parental cell-line towards cisplatin can reveal novel molecular targets and their role or contribution in chemoresistance of ovarian cancer tumors.

Additionally, this study examines a genomic therapy protocol for ovarian cancer treatment. As described herein, induction of higher levels of HE4 production caused cytotoxicity to ovarian cancer cells in vitro. To test the efficacy of induced HE4 production to suppress the progression of ovarian cancer in animal models, an inducible vector (pTRE-hyg) incorporating HE4 gene in multi-cloning site, under Doxycycline antibiotic negative (off) control has been incorporated in SKOV-3 cell lines. The proposed animal model will compare the progression of tumors in the HE4 high producer group versus the null vector group and or parental group. The volume of tumor growth will determine the efficacy of this approach.

Epithelial ovarian cancer is the leading cause of death from gynecologic cancer, in part because of the lack of effective early detection methods. Although alterations of several genes, e.g., c-erb-B2, c-myc, and p53, have been identified in a significant fraction of ovarian cancers, none of these mutations are diagnostic of malignancy or predictive of tumor behavior. HE4 overexpression negatively correlated with survival rate in endometrial, breast and lung cancer patients. In ovarian cancer, the biological role and impact of HE4 overexpression on various pathological parameters of EOC such as metastasis, chemoresistance, survival rates and other secondary clinical manifestations has yet to be determined. HE4 is a biomarker for early diagnosis and monitoring of EOC in patients. Serum HE4 levels was shown as a sensitive marker for differentiating malignant pelvic masses from benign neoplasms. HE4 is often not elevated in the benign gynecologic neoplasms when compared to serum CA125 and can differentiate endometriomas from malignant ovarian tumors.

Described herein are the dependent functions of HE4 network genes and signal transductions in ovarian cancer cells and in EOC in patients that facilitate ovarian cancer tumors onset and progression. Moreover, described herein are biologic agents to improve EOC treatment outcome either as single agents or as sensitizers in combination with other agents.

HE4 a whey-acidic (WAP) protein is highly overexpressed in EOC tumors. Prior to the invention described herein, the biological impact of HE4 overexpression on the pathogenisis of EOC was unknown. In endometrial, breast and lung cancer patients, HE4 overexpression is associated with signficantly reduced survival rates. By contrast, HE4 expression is highly enriched in human epidyemic, saliva, trachea, nasal and pulomonary tissues, and in sites of inflammation. A dichotomous dual function of HE4 has been observed in ovarian cancer cells where on one hand HE4 overexpression promotes strong chemoresistance, and on the other hand induced production of higher levels of HE4 was highly lethal to proliferating cancer cells Determination of Relative HE4 Production and Secretion Levels in a Panel of Cancer Cell-lines and Normal Human Cell Lines The expression of HE4 in variety of cancer tissue types has been shown by gene expression profiling, and immunohistochemistry. But the cellular HE4 production and secretion levels in various cancer cell types or normal cells have not been shown prior to the invention described herein. An ELISA showed that cellular HE4 production and secretion levels are cell-type specific but not tissue type specific. Both cancer cells and normal cells produce/secrete differential levels of HE4. For example, CaOV-3, an ovarian cancer cell line showed higher HE4 production and secretion in media than SKOV-3 cells. Similarly, third trimester extravillous trophoblasts (TCL-1) cells showed higher levels of HE4 production and secretion than their more invasive counterpart HTR-8 cells. Non-malignant human kidney cells (HK2) also showed HE4 production/secretion. Breast cancer (MCF-7), prostate cancer (PC-3) and neuroblastoma (IMR-32) cells did not show lower levels of HE4 production or secretion.

Identification of Factors that Affect HE4 Levels in Ovarian Cancer Cells

Figure 6A:
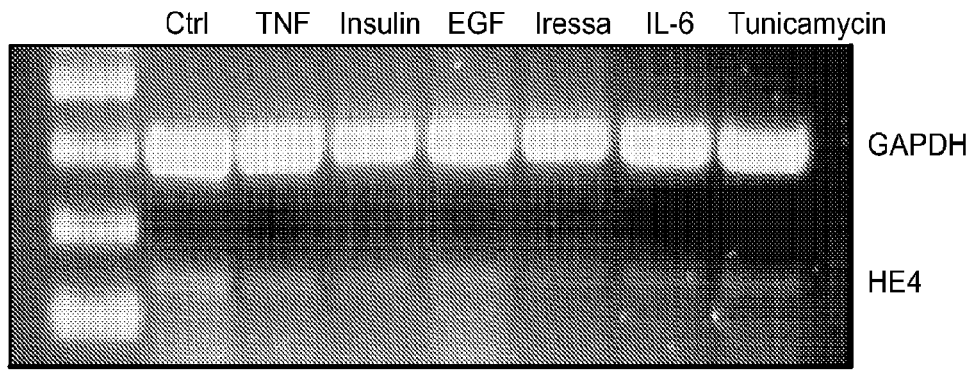
FIG. 6A shows the results of SKOV-3 cells stimulated with TNF (10 nM), Insulin (100 nM), EGF (10 nM), IL-6 (10 nM) and Tunicamycin (5 uM) in serum free DMEM and HE4 mRNAs.
Figure 6B:
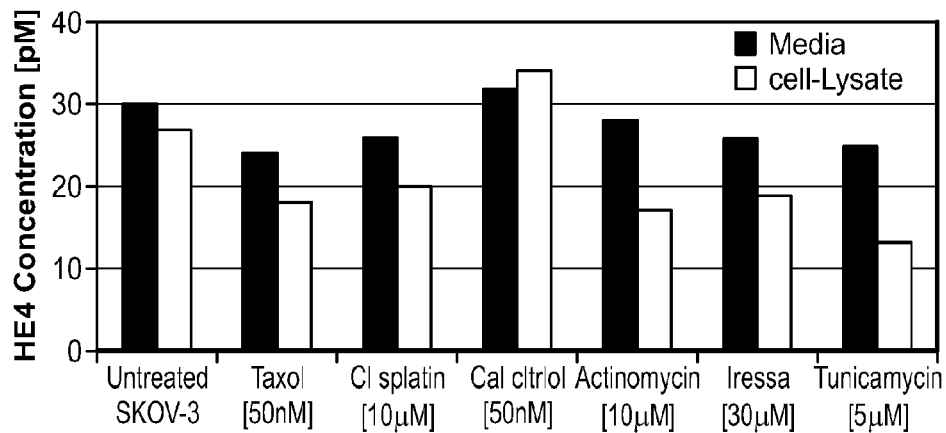
FIG. 6B shows the results of SKOV-3 cells treated with chemotherapeutics for 24 hrs in serum free DMEM media. HE4 levels in cell lysates and media were evaluated by a sandwich ELISA.

Molecular factors that affect/regulate HE4 expression (production+secretion) in ovarian cancer cells have not been determined prior to the invention described herein. Stimulation with growth factors (Insulin-like growth factor: IGF, EGF, TGF, Insulin), cytokines (IL-6 and TNF-a) did not affect mRNA expression of HE4 in SKOV-3 cells (FIG. 6). These factors contribute to inflammation, ovarian cancer progression and chemoresistance. Cytotoxic agents: Taxol, cisplatin, Iressa Actinomycin-D and Tunicamycin, a N-glycosidase inhibitor suppressed HE4 levels in SKOV-3 indicating that HE4 is a candidate prosurvival factor or oncogene. Calcitriol treatment upregulated HE4 expression compared to the untreated controls.

HE4 Overexpression Enhanced Chemoresistance and Evolved Highly Aggressive Phenotype of Ovarian Cancer A panel of stably higher HE4 overexpressing SKOV-3 cell clones(SKOV-3HE4C1, SKOV-3HE4C3, SKOV-3HE4C7) via pCMV6-HE4 vector was developed. Differential HE4 mRNA levels among clones versus parental SKOV-3 cells were detected by semi-quantitative PCR, while a sandwich ELISA (Fujirebio Diagnostics Inc.) was employed to estimate the cellular HE4 production (in cell-lysates) and secretion levels of HE4 (in media). Out of 10 high expressor clones, three clones with gradient increase in HE4 production/secretion levels (clone-1>clone-3>clone-7) were selected as models for the study in parallel with parental SKOV-3 cell-line (FIGS. 2, 4, and 5). The impact of HE4 overexpression on the response of cisplatin, Taxol, doxorubicin and camptothecin was determined by a cell viability assay. HE4 overexpression muted the response of cisplatin, Taxol, doxorubicin, camptothecin, significantly. The HE4 overexpressor clones of SKOV-3 cells showed ~4-8 fold lower response to cisplatin, Taxol, Doxorubicin and camptothecin treatment compared to parental SKOV-3 cells.

HE4 Overexpression Enhanced Oncogenic/Growth Factor Receptor Activation

Figure 7:
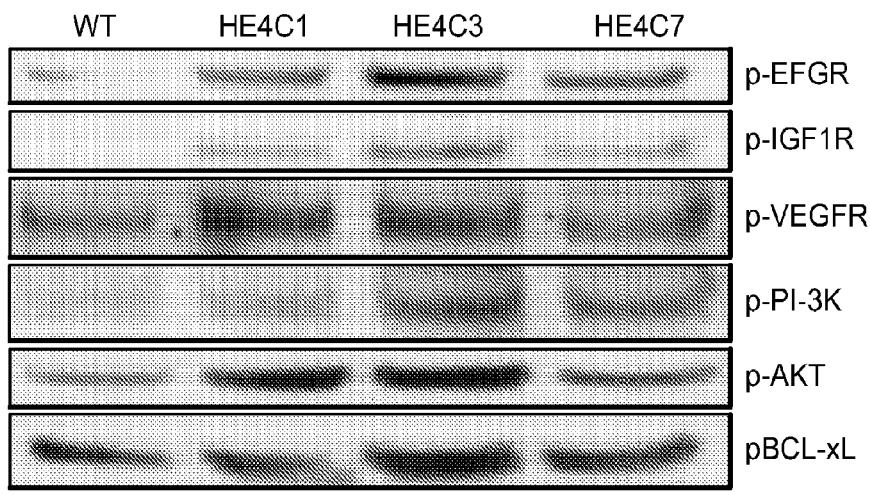
FIG. 7 is a series of photomicrographs showing HE4 overexpressing clones (1, 3 and 7) show higher activation levels of oncogenic epidermal growth factor receptor (EGFR), Insulin-like growth factor (IGF1R), VEGFR and PI-3K/AKT compared to parental SKOV-3 cells.

To determine the cause of enhanced chemoresistance among HE4 overexpressing ovarian cancer cells, it was identified that high expressor clones carried higher constitutive activation/phosphorylation of EGFR, IGF1R, PI-3K/AKT, BCl2 family proteins when compared to the parental SKOV-3 cells (FIG. 7). Notably, these oncogenes/growth factors are strongly implicated in the pathogenesis of ovarian cancer and the development of chemoresistant phenotypes of ovarian cancer. Targeted therapies against these molecular targets are currently undergoing clinical trials to treat epithelial ovarian cancer (EOC).

HE4 Overexpressing SKOV3 Cloned Cells Compared to Parental Cells Showed Faster G2/M Entry and Proliferation Rate CDC25B is the key regulator for G1/S phase progression in ovarian cancer cells. HE4 clones showed higher G2/M phase and lower G1 phase cell population. The cell lysate of the wild type SKOV-3, HE4C1, C3 and C7 clones were probed for the expression of key regulators of G1/S or G2/M phases of the cell cycle (FIG. 3). Compared to parental SKOV-3 cells, HE4 overexpressors showed higher proliferation rate, enhanced G2/M entry in consonance with enhanced CDC2 and suppressed cyclin-B1 and CDC25B (FIG. 3).

MT19c Showed Enhanced Sensitivity to HE4 Over Expressing SKOV3 Cloned Cells Compared to Parental Cells Various anticancer agents showed faced strong chemoresistance upon HE4 overexpression in SKOV-3 cells (FIG. 8). By contrast, a cell viability screen of a library of compounds revealed that HE4 overexpressing clones were up to 8 fold more sensitive to MT19c and PT19c two biologics. While the mechanism of the enhanced sensitivity of HE4 over expressing clones towards MT19c and PT19c has yet to be determined, as described herein, MT19c is utilized to treat HE4 over expressing sub group of epithelial ovarian cancers.

Figure 9A:
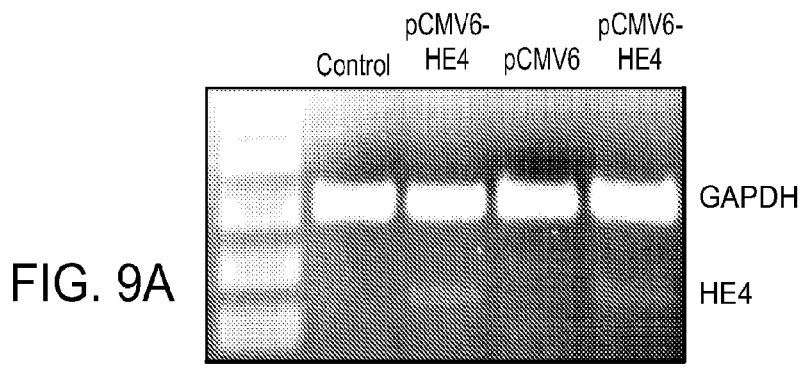
FIG. 9 is a series of photomicrographs, bar graphs and line graphs demonstrating the cytotoxic features of induced HE4 production. pCMV6-HE4 overexpressing vector induced HE4 activation was verified by RT-PCR (FIG. 9A) and sandwich ELISA (FIG. 9B). Transient production of HE4 suppressed the proliferation of ovarian (SKOV-3) and endometrial (ECC-1) cells (FIG. 9C) but human kidney cells (Hk2) were not affected (FIG. 9D). Induced HE4 production caused apoptosis and activated caspase-3, -8 and 9 followed by PARP-1 cleavage (FIG. 9E) followed by MAPKinase activation and suppression of pro-survival Bcl2 family proteins (FIG. 9F). Transient HE4 activation produced lethal levels of ROS in SKOV-3 cells (green=control; blue=pCMV6-HE4 transfected SKOV-3 cell.
FIG. 9G). (LIP: lipofectamine).
Figure 9B:
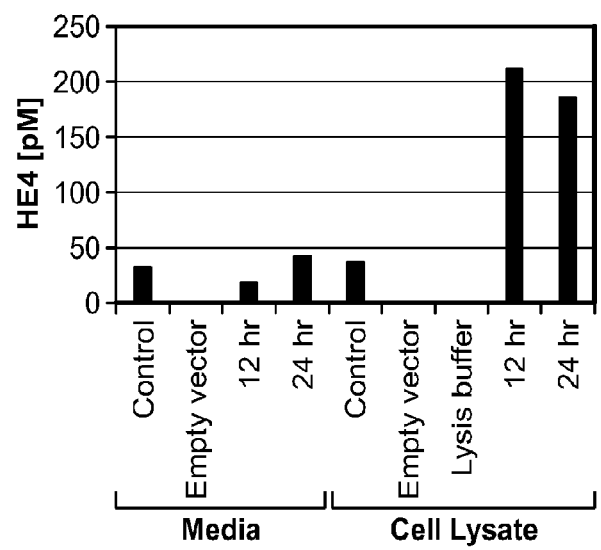
Figure 9C:
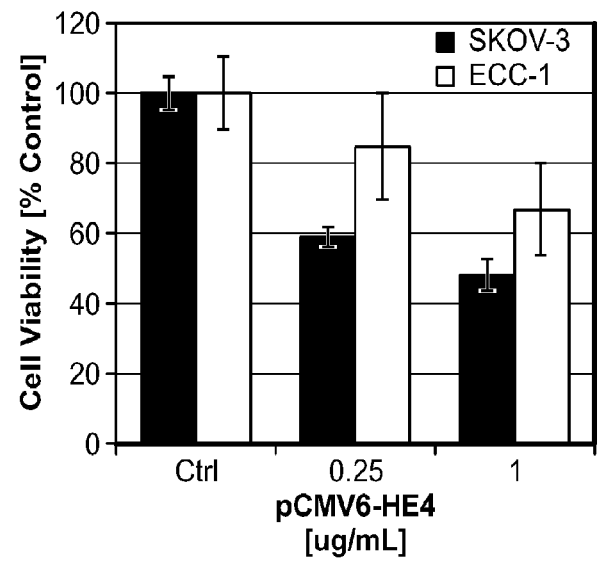
Figure 9D:
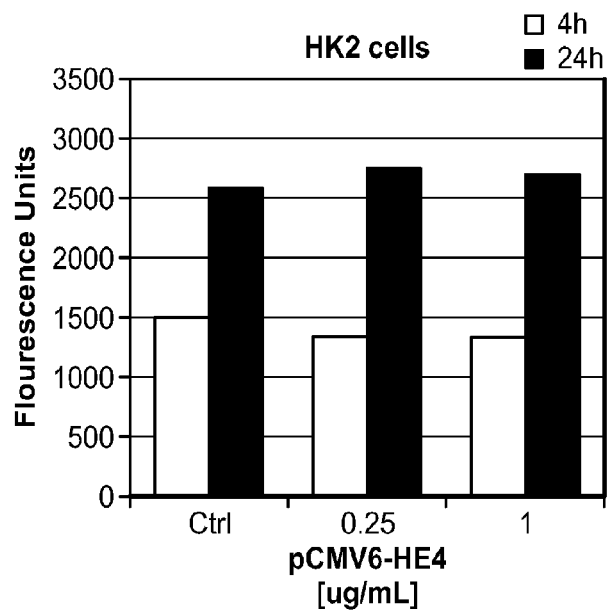
Figure 9E:
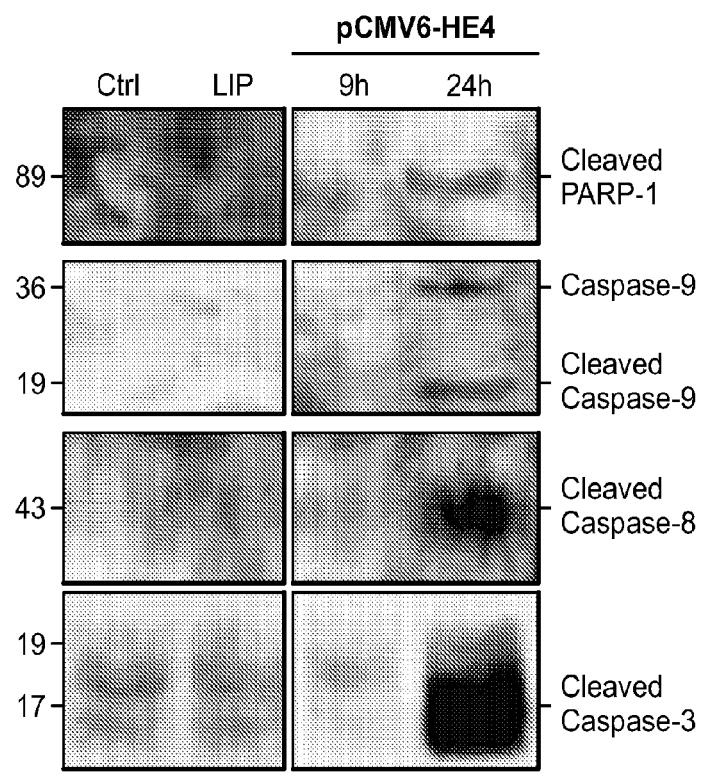
Figure 9F:
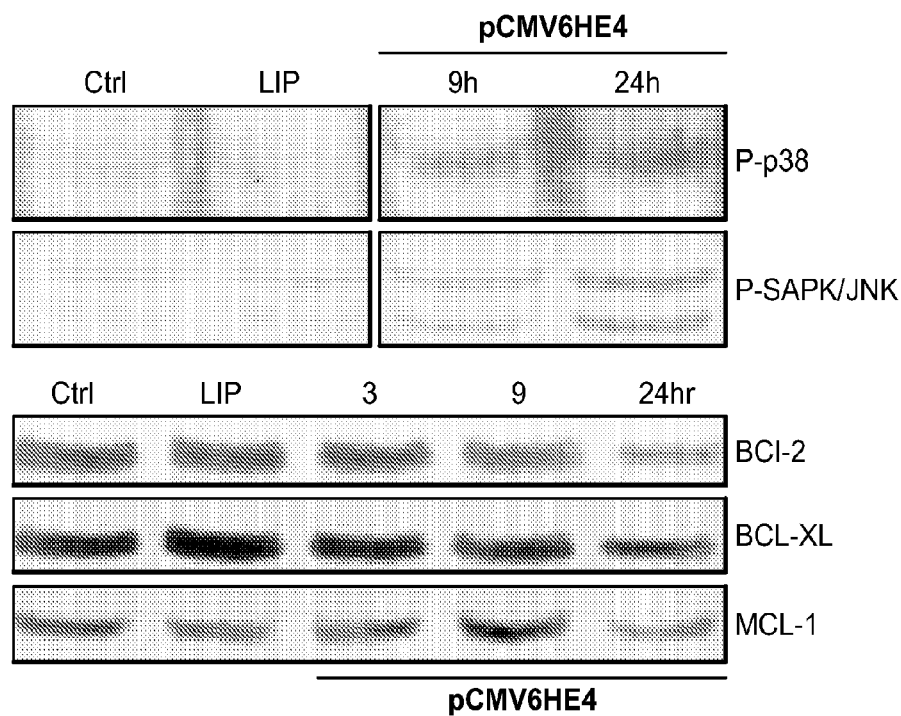
Figure 9G:
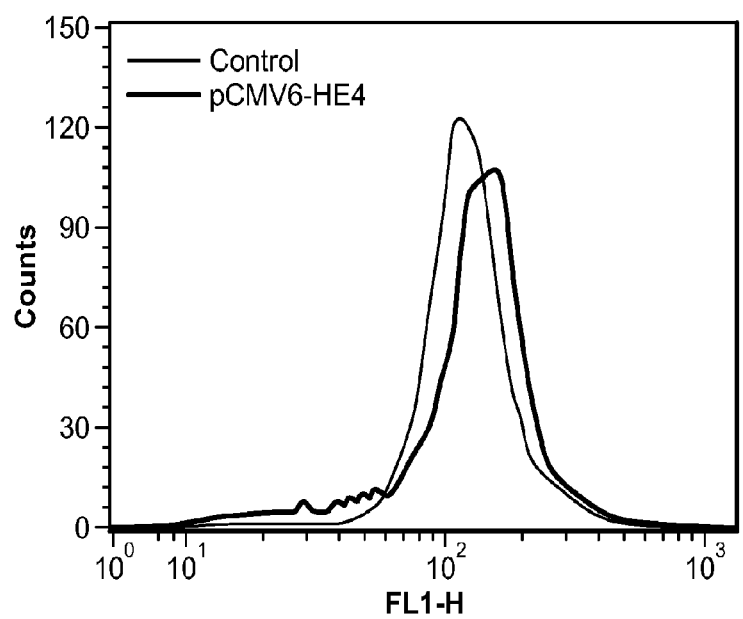

Induction of Higher Levels HE4 of HE4 Production is Selectively Cytotoxic to Ovarian Cancer Cells Induction of higher HE4 cellular production via pCMV6-HE4 vector (FIG. 9A-B) was highly toxic to ovarian and endometrial cancer cells (C) but non-cytotoxic to human kidney (HK2) (D), mouse kidney cell (MES 13) and trophoblastic cells. Lethal levels of HE4 production caused apoptotic events such as DNA fragmentation, chromatin condensation, caspase and MAPkinase activation followed by downregulation of BCl2 family protein expression in SKOV-3 cells (FIG. 9E-G). Induced HE4 activation arrested SKOV-3 cells in $G_0/G1$ phase and produced lethal reactive oxygen species (ROS) (FIG. 9H). To further investigate the potential of inducing lethal levels of HE4 to target ovarian cancer cell death in animal models, an inducible vector pTRE-hyg-HE4-SKOV under Doxycycline (−ve) control was developed.

Figure 10A:
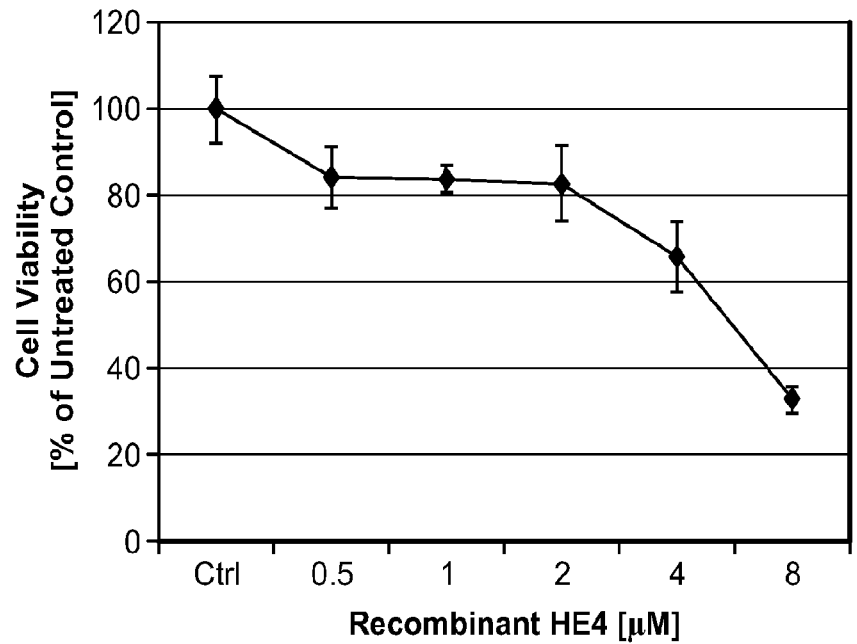
FIG. 10A shows that recombinant HE4 suppressed the viability of SKOV-3 cells within 24 hours.
Figure 10B:
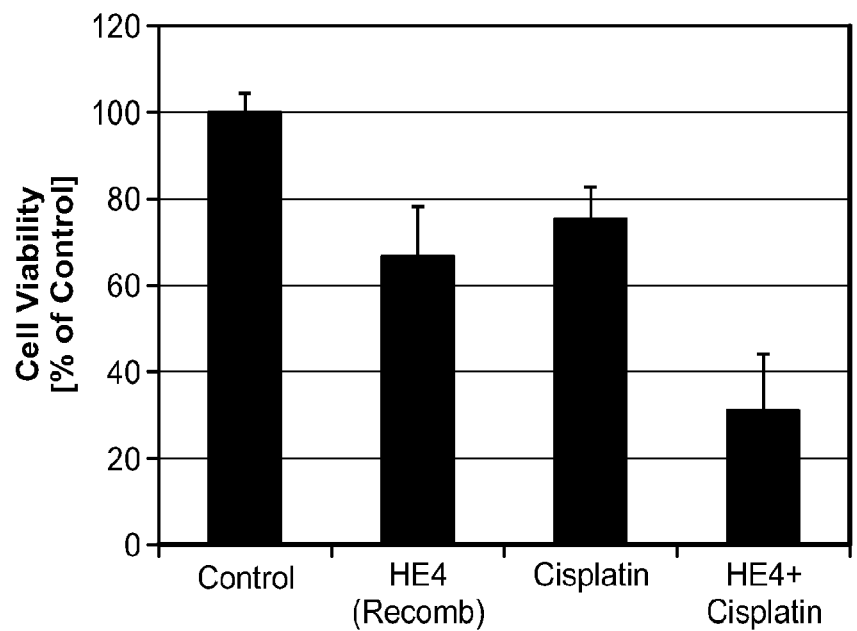
FIG. 10B shows that pretreatment with HE4 (4 ng/mL) enhanced the efficacy of cisplatin in SKOV-3 cells.

Recombinant HE4 is Selectively Cytotoxic to Cancer Cells and Synergizes the Cisplatin Response Exogenous recombinant HE4 treatment suppressed the viability of ovarian cancer (SKOV-3, CaOV-3) selectively (FIG. 10). Similar effects were observed with endometrial cancer cell-lines (ECC-1). The viability of human kidney (HK2) was not affected in the dose range tested. It was also observed that a pre-treatment with exogenous recombinant HE4 enhanced the efficacy of cisplatin in SKOV-3 cells.

EXAMPLE 3

The Functional Impact of HE4 Overexpression Ovarian Cancer

Prior to the invention described herein, the cause and biological impact of HE4 overexpression in ovarian cancer was unknown. In endometrial, breast and lung cancers, HE4 overexpression correlated with significantly lower survival rates and worse prognosis. In ovarian cancer models, as described herein, constitutive HE4 overexpression muted the response of cisplatin, Taxol, doxorubicin and camptothecin (FIGS. 2, 4, and 5) and displayed highly aggressive phenotype blessed with higher activation levels of chemoresistance and oncogenic effector protein/genomic factors (EGFR, IGF1R and VEGFR), PI-3K/AKT or Bcl2 family proteins compared to parental SKOV-3 cells.

The Biological Impact of HE4 Overexpression in the Pathogenesis and Propagation of Ovarian Cancer The chemoresistance and oncogenic effects of stable HE4 overexpression is validated in animal models of ovarian cancer. To accomplish this objective, a panel of HE4 overexpressing SKOV-3 clones (pCMV6-HE4$^+$) with differentially higher HE4 production and secretion levels compared to parental SKOV-3 cell-lines has been generated. The chemotherapy response of xenografts derived from the clones versus parental lines highlights the correlation of HE4 levels with the chemotherapy, response.

A panel of stable HE4 overexpressing SKOV-3 cell clones via pCMV6-HE4 vector was developed. These clones displayed strong chemoresistance to Taxol, Cisplatin, or Doxorubicin treatment compared to parental SKOV-3. To validate the role of HE4 overexpression in chemoresistance and ovarian cancer progression, xenografts of SKOV-3/WT and SKOV-3HE4$^+$ clones are developed in animals and then treated with various chemotherapeutic regimens. Similarly, Luciferase$^+$-SKOV3-HE4$^{++}$ clones are developed to elucidate the impact of HE4 overexpression on ascites, metastasis, angiogenesis and invasion characteristics of ovarian cancer. Genomewide mRNA in parental versus SKOV-3HE4+ groups are analyzed to identify chemoresistance targets against cisplatin. HE4 pharmacologic inhibitors are identified by library screening to combat HE4 role in progression and chemoresistance in ovarian cancer.

Prior to the invention described herein, the biological impact of HE4 overexpression in ovarian cancer patients was not known. HE4 is overexpressed in EOC. Similarly, prior to the invention described herein, the impact of HE4 overexpression in ovarian cancer was unknown in cultured cell or in vivo models. HE4 overexpression negatively correlated with significantly reduced survival of endometrial, breast and lung cancer patients. In ovarian cancer cell models, it was observed that HE4 overexpressing SKOV-3 cell clones showed a 20 fold increase in resistance to cytotoxic chemotherapeutics including Taxol, Cisplatin, Doxorubicin and camptothecin treatment. Stably HE4 overexpressing ovarian cancer cell (SKOV-3) clones compared to parental SKOV-3 cells displayed highly aggressive phenotype blessed with higher activation levels of chemoresistance and oncogenic effector protein/genomic factors (EGFR, IGF1R and VEGFR), PI-3K/AKT or Bcl2 family proteins compared to parental SKOV-3 cells.

To study the role of HE4 overexpression in chemotherapy resistance and ovarian cancer progression, xenografts of HE4 overexpressing SKOV-3 clones and parental SKOV-3 cells are developed in animals and treated with cisplatin. Measurement of tumor volume and Kaplan-Meier analysis of the survival of the animal subject defines the extent of chemoresistance arising due to HE4 overexpression. A Gene Set Enrichment Analysis (GSEA) of the genome wide mRNA isolated from HE4$^{++}$ clones and parental cell derived subcutaneous ovarian cancer xenograft tumor treated with cisplatin identifies the genes and define the role of HE4 in chemoresistance and oncogenesis of ovarian cancer.

To determine the role of HE4 in ovarian cancer metastasis and proliferation, Luc$^+$-SKOV- 3 cells are stably trans-formed into HE4 overexpressing clones. The subcutaneous animal xenografts of Luc-SKOV-3-HE4+ cells versus vector control Luc-SKOV-3 cells are grown in mice and cisplatin treatment is applied. This arm of study quantitates the extent of metastasis promotion linked to HE4 overexpression by an In-vivo imaging system. Migration characteristics of HE4 overexpressing clones versus null vector Luc-SKOV-3 cells are assessed by a QCM-Collagen I Quantitative Cell Migration Assay kit (Chemicon, Temecula, Calif.). Migrated cells on the bottom of the insert membrane are dissociated, collected and detected with CyQuant GR dye (chemicon) at 80 nm by a fluorescence microplate reader. The migrated cells in both groups are calculated as a percentage of the control value obtained for the parental cells. Experiments are repeated in triplicate and appropriate statistical gating is applied to assess the significance of the experiments. Similarly, Invasion characteristics of HE4 overexpressing clones versus null vector SKOV-3 cells is quantified via a Boyden chamber (8 μm pore size) coated with Matrigel (BD Biosciences, Bedford, Mass.). The cells that migrated through the membrane to the lower surface are fixed, stained with Hematoxylin and counted by 4 quadrants under a light microscope. At least three independent experiments are carried out and results are expressed as mean of +/−SD. Group means are compared using two-sided two sample Student's T-test.

The role of HE4 overexpression in chemoresistance, metastasis, angiogenesis and invasion/migration characteristics of ovarian cancer cells in animal models is revealed for the first time. The Gene Set Enrichment Analysis (GSEA) of the genome wide mRNA reveals the key genes and their functional role in the evolution of chemoresistance and promotion of metastasis of ovarian cancer due to HE4 overexpression. Based on the identification of genes and their functions, novel therapeutic strategies/agents are developed to counter those effects and improve the treatment outcome in ovarian cancer.

Evaluation of the Cytotoxic Effects of HE4 Genomic Activation in Ovarian Cancer Models Described in detail below is the outcome of the genomic HE4 activation via an inducible vector (pTRE-hyg-HE4) under (−ve) Doxycycline control in animal models. It was observed in cultured ovarian cancer cells that genomic activation of HE4 via pCMV6-HE4 vector suppressed ovarian cancer cell viability and survival and caused apoptosis and cell cycle arrest.

Inhibition of ovarian and endometrial cancer cell proliferation, apoptosis and death was achieved by inducing toxic level of HE4 production in cancer cells via pCMV6-HE4 vector. Normal cells (e.g., HK2, human kidney cells) with similar proliferation rate were not affected. To target ovarian cancer cell death by genomic activation of HE4, an inducible vector (pTRE-hyg) incorporating HE4 gene in multi-cloning site, under Doxycycline antibiotic negative (off) control was ligated in SKOV-3 cells. The xenografts of pTRE-hyg-HE4 and pTRE-hygSKOV-3(null vector) and SKOV-3(WT) cells are developed and Doxycycline deprivation applied. The tumor size, ascites, metastasis characteristics determine the outcome of genomic HE4 activation alone or in combination with cisplatin in a separate arm of the study in animals.

Ovarian cancer is normally confined to the abdominal and pelvic cavities with involvement of the peritoneal surfaces. HE4 expression is enriched locally on the peritoneal surfaces targeted HE4 activation is likely to be an efficient genomic therapy approach to treat ovarian cancer. The cultured ovarian cancer cells upon genomic activation of HE4 via pCMV6-HE4 vector suppressed the ovarian cancer cell viability and caused apoptosis, arrested cell cycle progression in $G_0/G1$ phase and down regulated expression of EGFR/PI-3k/akt and pros-survival Bcl2 family proteins. Described in detail below is the outcome of the genomic HE4 activation via an inducible vector (pTRE-hyg-HE4) under (−ve) Doxycycline control in animal models.

Inducible vector (pTRE-hyg-HE4) was incorporated in SKOV-3 cells to conditionally activate HE4 under Doxycycline (−ve) control. To study the outcome of induced HE4 activation in ovarian cancer progression, xenografts of pTRE-hyg-HE4$^+$ SKOV-3 clones and parental or null vector (pTRE-hyg-SKOV-3) cell clones are developed in animals and doxycycline deprivation applied. The measurement of the tumors, weight and other physical parameters determines the outcome of the approach.

In a separate arm the xenograft tumors are also treated with cisplatin to examine the therapeutic potential of combination therapy combined with genomic HE4 activation. Measurement of tumor volume and Kaplan-Meier analysis of the survival of the animal subject reveals the potential of induced HE4 activation in genomic therapy of ovarian cancer.

A Gene Set Enrichment Analysis (GSEA) of the genome wide mRNA isolated from HE4$^{++}$ clones and parental cell/null vector derived subcutaneous ovarian cancer xenograft tumor treated or vehicle treated with cisplatin and Taxol identifies the target genes and define their roles in the application of HE4 genomic activation in ovarian cancer treatment. The effect of genomic HE4 activation on the migration characteristics of (pTRE-hyg-HE4) clones under (−ve) Doxycycline versus null vector SKOV-3 cells is assessed by a QCM-Collagen I Quantitative Cell Migration Assay kit (Chemicon, Temecula, Calif.). Migrated cells on the bottom of the insert membrane are dissociated, collected and detected with CyQuant GR dye (chemicon) at 80 nm by a fluorescence microplate reader. The migrated cells in both groups are calculated as a percentage of the control value obtained for the parental cells. Experiments are repeated in triplicate and appropriate statistical gating is applied to assess the significance of the experiments. Similarly, Invasion characteristics of (pTRE-hyg-HE4) under (−ve) Doxycycline clones versus null vector SKOV-3 cells are quantified via a Boyden chamber (8 μ pore size) coated with Matrigel (BD Biosciences, Bedford, Mass.). The cells that will have migrated through the membrane to the lower surface are fixed, stained with Hematoxylin and counted by 4 quadrants under a light microscope. At least three independent experiments are carried out and results are expressed as mean of +/−SD. Group means are compared using two-sided two sample Student's T-test.

This study reveals the therapeutic potential of HE4 genomic activation to target ovarian cancer either as a standalone genomic therapy or in combination with cytotoxic agents such as cisplatin. Various gene and their putative role in suppression of chemoresistance to cisplatin, metastasis, angiogenesis and invasion/migration characteristics of ovarian cancer due to induced HE4 activation are revealed by a Gene Set Enrichment Analysis (GSEA) of the genome wide mRNA of the harvested tumors in both groups. Based on the identification of genes and their functions, novel therapeutic strategies/agents are developed to optimize the therapy outcome in ovarian cancer patients.

HE4 as a Marker for Chemoresistance and Poor Prognosis in Epithelial Ovarian Cancer Patients Described in detail below are experiments that delineate the impact of HE4 overexpression on the 'Disease Free Survival' (DSF) rate/'Overall Survival' (OS) rate and chemoresistance status in human EOC patients. The body fluids and tumor specimens at various stages of EOC patients are assessed for HE4 levels by ELISA, 1HC, RT-PCR and the relationship of HE4 overexpression at diagnosis, surgery, during the chemotherapy rounds, and post chemo status until death are correlated statistically to identify the role of HE4 in EOC pathogenesis in patients.

The objective is to evaluate HE4 expression levels in EOC patient's specimen and correlate it with chemoresistance and its impact on survival (OS) rates. In cultured ovarian cancer cells HE4 overexpression showed strong chemoresistance against chemotherapeutic regimens. A prospective collection of body fluids (serum, plasma, urine) and fresh/frozen tissues of EOC patients is analyzed and quantitated for HE4 levels by ELISA, immunohistochemistry and RT-PCR techniques. The body fluids/tumor specimens of the EOC patients are collected preoperatively, at surgery, before and during first, second and third chemotherapy and every third month until patients die. The primary cells from tissues are isolated and chemosensitivity assessed by a cell viability assay, and expression of oncogenes and chemoresistance markers are assessed by RT-PCR or immunoblotting. To examine if overexpression of HE4 protein induces neoplastic transformation due to genetic mutations in patients, sequence EOC patients tumor/body fluid specimens are sequenced to detect mutations in the coding sequence/highly conserved region of HE4 gene.

HE4 overexpression and its relationship and role with chemoresistance and disease free survival (DFS) and overall survival (OS) in EOC patients is examined. As described above, in cultured ovarian cancer cells HE4 overexpression emerged as a potential chemoresistance marker. In endometrial, breast and lung cancers patients, HE4 overexpression correlated with significantly lower survival rates.

A prospective collection of body fluids (serum, plasma, urine) and fresh/frozen tissues of EOC patients is analyzed and quantitated for HE4 levels by ELISA, immunohistochemistry and RT-PCR techniques. The body fluids/tumor specimens of the EOC patients are collected preoperatively, at surgery, before and during first, second and third chemotherapy and every third month until the patient dies. The primary cells from tissues are isolated and chemosensitivity assessed by a cell viability assay, and expression of oncogenes and chemoresistance markers is assessed by RT-PCR or immunoblotting. To examine if overexpression of HE4 protein induces neoplastic transformation, EOC patients tumor/body fluid specimens are sequenced to detect, mutations in the coding sequence/highly conserved region for HE4 gene.

The survival rate of patients is determined by Kaplan-Meier Analysis. Gene Set Enrichment Analysis (GSEA) and Ingenuity System Pathway Analysis (IPA) of the genome wide mRNA expressions in the harvested tumors identifies the HE4 linked molecular targets/factors and their role in awarding chemoresistance against chemotherapy regimens (e.g., the platinum and Taxol) in EOC patients. Identification of molecular targets aids in designing novel HE4 inhibitors to combat HE4 role in progression and chemoresistance in ovarian cancer patients to optimize response of chemotherapies in EOC patients.

This study reveals the impact of HE4 overexpression on chemotherapy response, disease free survival (DSF) or overall survival (OS) in the EOC patients. The observation that HE4 overexpression affords chemoresistance against cisplatin, Taxol, doxorubicin and camptothecin is validated in human patients. Various chemoresistance, metastasis, angiogenesis and invasion/migration genes/proteins and their putative role impacted by HE4 overexpression is identified by a Gene Set Enrichment Analysis (GSEA) and IPA analysis of the genome wide mRNA of the harvested tumors and other biological specimens. Based on the identification of genes and their functions, novel therapeutic strategies and agents are identified to optimize the therapy outcome in HE4 impacted ovarian cancer patients.

Human Studies

Described herein is a prospective study of one hundred (100) chemotherapy and surgery naïve human ovarian cancer patients. A prospective collection of body fluids (serum, plasma, urine) and fresh/frozen tissues of EOC patients is analyzed and quantified for HE4 levels by ELISA, immunohistochemistry and RT-PCR techniques. The body fluids/tumor specimens of the EOC patients are collected preoperatively, at surgery, before and during first, second and third chemotherapy and every third month until patients die. The primary cells from tissues are isolated and chemosensitivity assessed by a cell viability assay, and expression of oncogenes and chemoresistance markers is assessed by RT-PCR or immunoblotting. To examine if overexpression of HE4 protein induces neoplastic transformation due to genetic mutations in HE4 gene in patients, EOC in the patient's tumor/body fluid specimens are sequenced to detect mutations in the coding sequence/highly conserved region of HE4 gene.

Figure 12A:
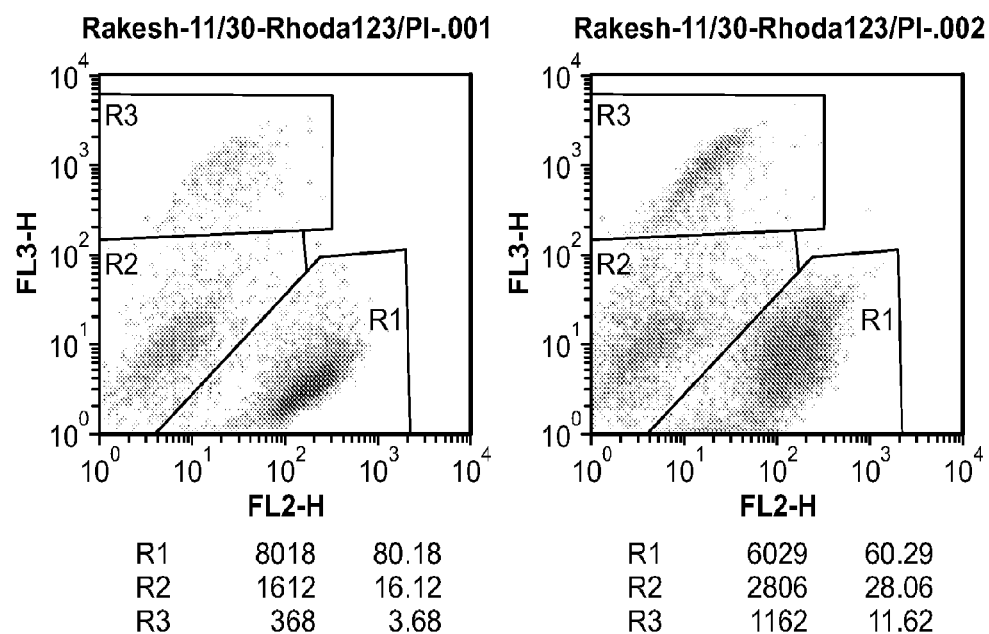
FIGS. 12A-12B is a series of fluorescence-activated cell sorting (FACS) graphs and a bar chart demonstrating that HE4over-expression causes apoptosis in a representative ovarian cancer cell line (SKOV-3).
Figure 12B:
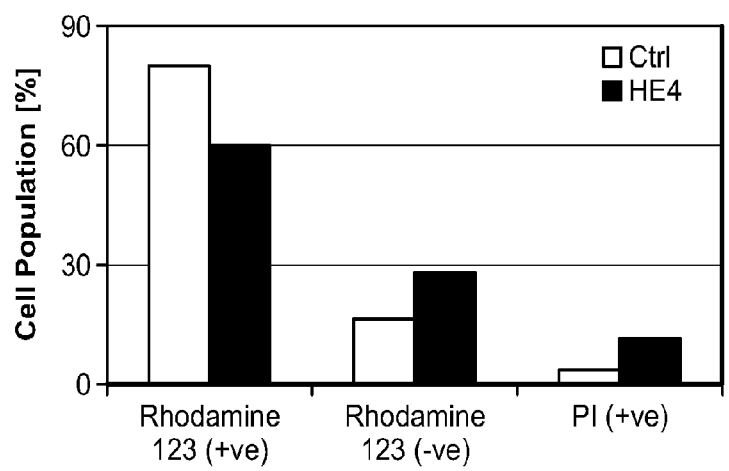
Figure 13A:
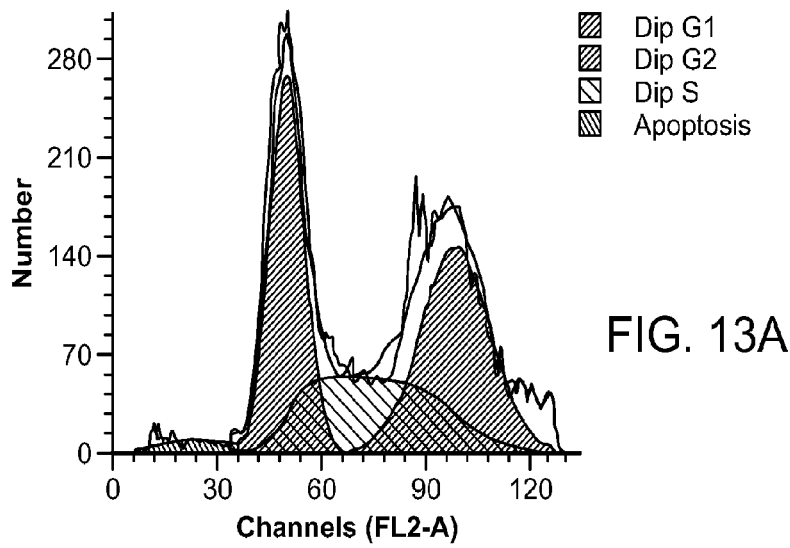
FIGS. 13A-13D is a series of fluorescence-activated cell sorting (FACS) graphs and a bar chart demonstrating that HE4over-expression Sub-G1 arrest in SKOV-3 cells.
Figure 13B:
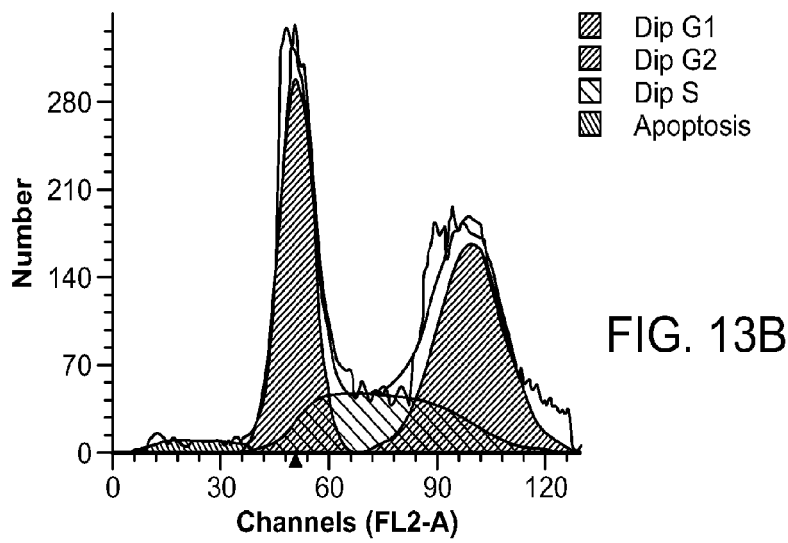
Figure 13C:
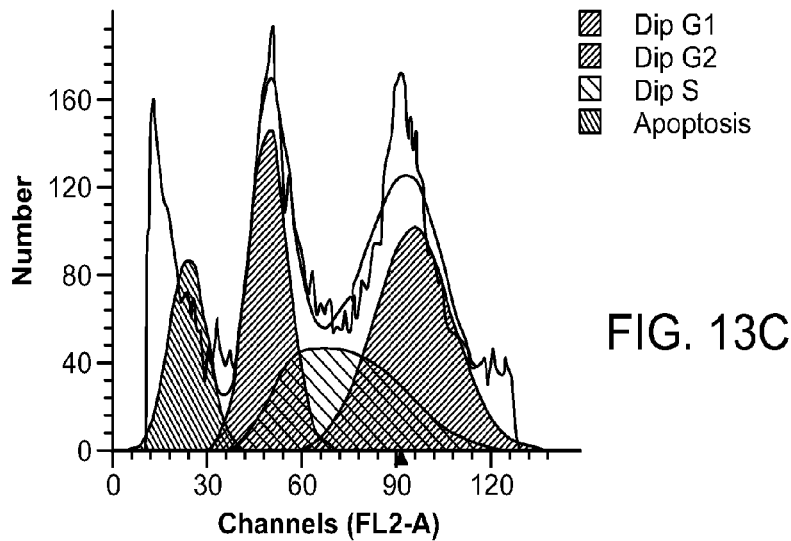
Figure 13D:
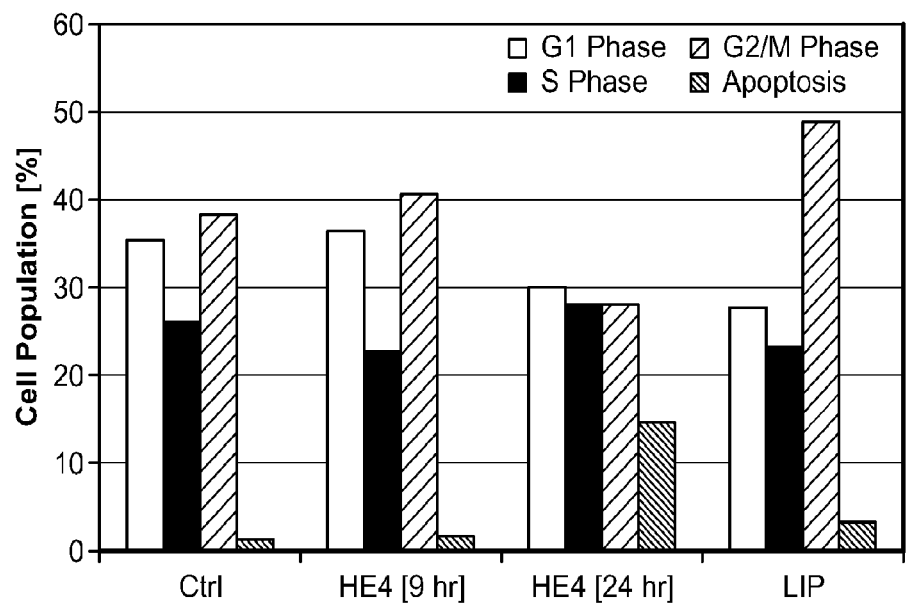

The results in FIG. 12 show that HE4 over-expression causes apoptosis in a representative ovarian cancer cell line (SKOV-3). SKOV-3 cells (1 million) were seeded in petri dishes and allowed to adhere overnight in DMEM media supplemented with 10% fetal bovine serum (FBS) without antibiotic. In a separate tube, HE4 cDNA was complexed with lipofectamine (Invitrogen) for 1 min-2 hrs in Optimem media (Invitrogen). HE4 cDNA-Lipofectamine complex dissolved in Optimem media were added to the cells. Lipofectamine and no drug were used as control. After 24 hours, media was removed and cells were trypsinized and collected after centrifugation. Cells were washed with PBS and resuspended in RPMI complete media. Resuspended cells were incubated with Rhodamine 123 dye (1-20 µM) for 30 minutes-1 hour and Propidiniun Iodide (PI) solution (1-20 µM) was added and incubated for 30 minutes. The cell population positive for rhodamine123 and PI was analyzed using FACS with appropriate gating sets. FIG. 12 shows that HE4 overexpression leads to the increase in the PI positive cells (indication of apoptosis) and decrease in Rhodamine 123 positive population (sign of early apoptosis).

The results presented in FIG. 13 show that HE4 overexpression Sub-G1 arrest in SKOV-3 cells. Ovarian cancer cells (SKOV-3) (1 million) were seeded in petri dishes and allowed to adhere overnight in DMEM media supplemented with 10% Fetal Bovine serum without antibiotic. In a separate tube, HE4 cDNA pre-was complexed with lipofectamine (Invitrogen) for 1 min -2 hrs in Optimem media (Invitrogen). HE4 cDNA-Lipofectamine complex dissolved in Optimem media were added to the cells. Lipofectamine and no drug were used as control. Cells were harvested at different intervals (9 hrs and 24 hr) and fixed in 70% EtOH. The cells were centrifuged and the cell pellets were treated with propidinium iodide (PI) and cell population was analyzed as described previously (Singh R K, et al, Br Journal of Cancer, 2008, 99:1823-1831). The histogram shows that while lipofectamine induced a G2/M phase arrest, HE4 over-expression led to the sub-G1 phase arrest (<15%).

Figure 14A:
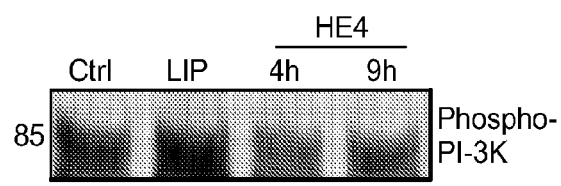
FIGS. 14A-14B is a series of photomicrographs of western blots demonstrating that HE4 overexpression caused downregulation of pro-survival PI-3k/AKT signaling.
Figure 14B:
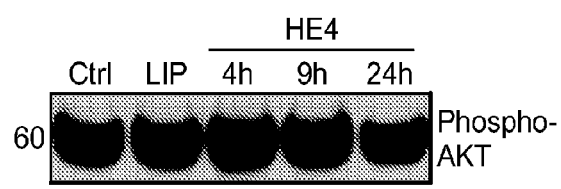

FIG. 14 shows that HE4 overexpression caused down-regulation of pro-survival PI-3k/AKT signaling. HE4 over-expression causes deactivation of pro-survival mitochondrial proteins in SKOV-3 cells. Ovarian cancer cells (SKOV-3) (1 million) were seeded in petri dishes and allowed to adhere overnight in DMEM media supplemented with 10% Fetal Bovine serum without antibiotic. In a separate tube, HE4 cDNA was complexed with lipofectamine (Invitrogen) for 1 min-2 hrs in Optimem media (Invitrogen). HE4 cDNA Lipofectamine complex dissolved in Optimem media were added to the cells. Lipofectamine and no drug were used as control. At different time points (4 hrs, 9 hrs and 24 hr), cells were collected and lysed using lysis buffer. The protein concentration was estimated using the Bradford assay. The western blot analysis of the lysates was performed as described previously (Singh R K, et al, Br Journal of Cancer, 2008, 9:1823-1831). The blot was probed with monoclonal or polyclonal anti-BCl-xL, anti-Bcl2, and anti-MCl-1 antibodies. Actin was used as an internal control. Effect of HE4 activation on PIP2-PIP3 conversion was assessed by lipid kinase assay (Yano N. et al. Biochem. J. (2009) 423 (129-143).

Figure 15:
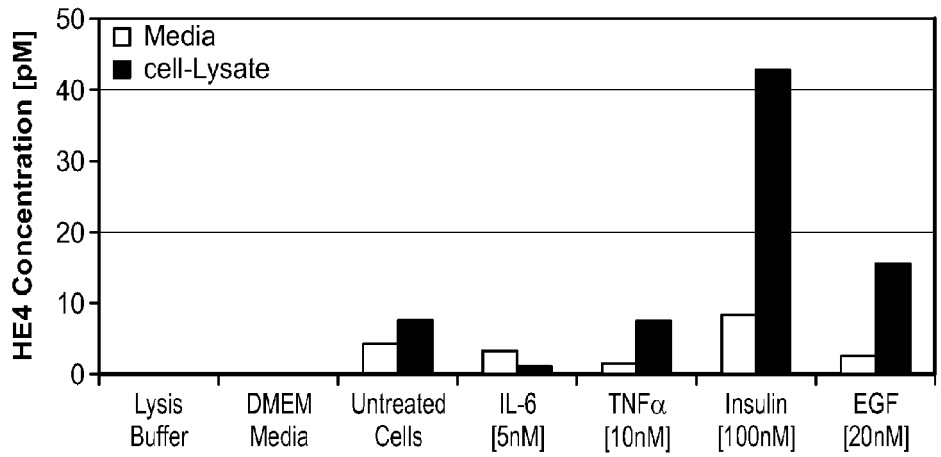
FIG. 15 is a bar chart demonstrating that treatment with growth factors and cytokines affect the HE4 levels in ovarian cancer cells.
Figure 16:
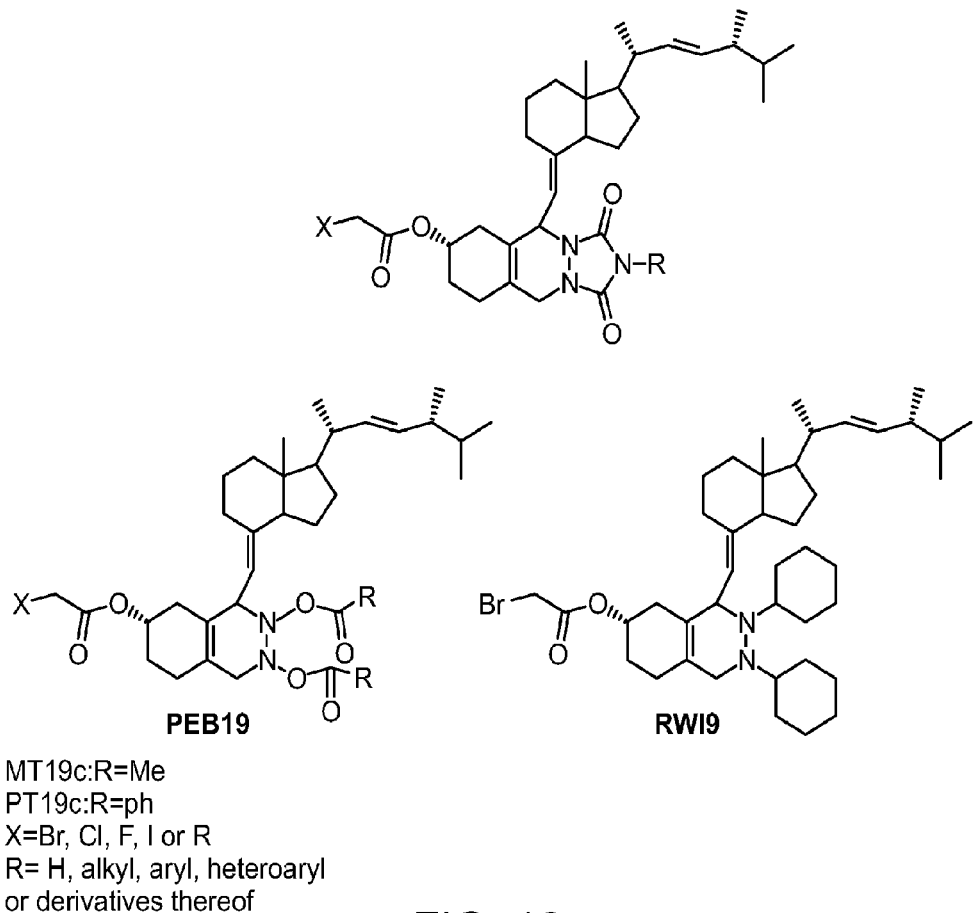
FIG. 16 is a series of structures showing vitamin D derivatives.
Figure 17A:
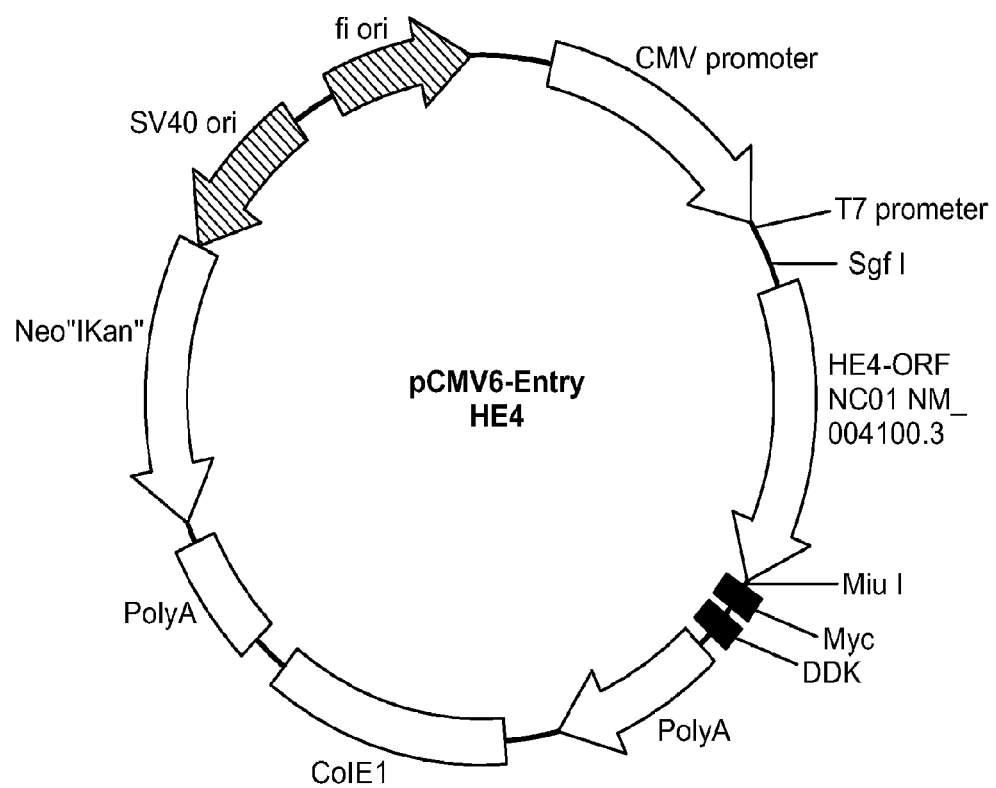
FIG. 17 is a series of schematics, photographs, bar charts, and line graphs demonstrating that HE4 activation confers chemoresistance. Specifically, HE4 overexpression significantly muted the response to Cisplatin and Paclitaxel. (A,B): A panel of HE4 overexpressing SKOV-3 cell clones stably transfected with pCMV6-HE4 was developed. (C,D): HE4 overexpression (both secretion and production) was confirmed by sandwich ELISA. (E,F): The HE4 overexpressing SKOV-3 clones showed significantly reduced response to Cisplatin and Paclitaxel treatment compared to parental SKOV-3 cells.
Figure 17B:
Figure 17C:
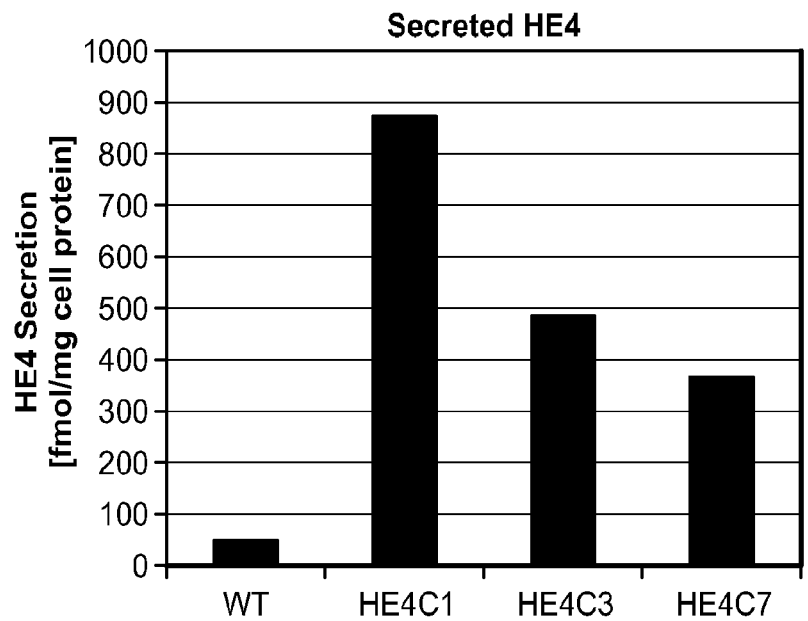
Figure 17D:
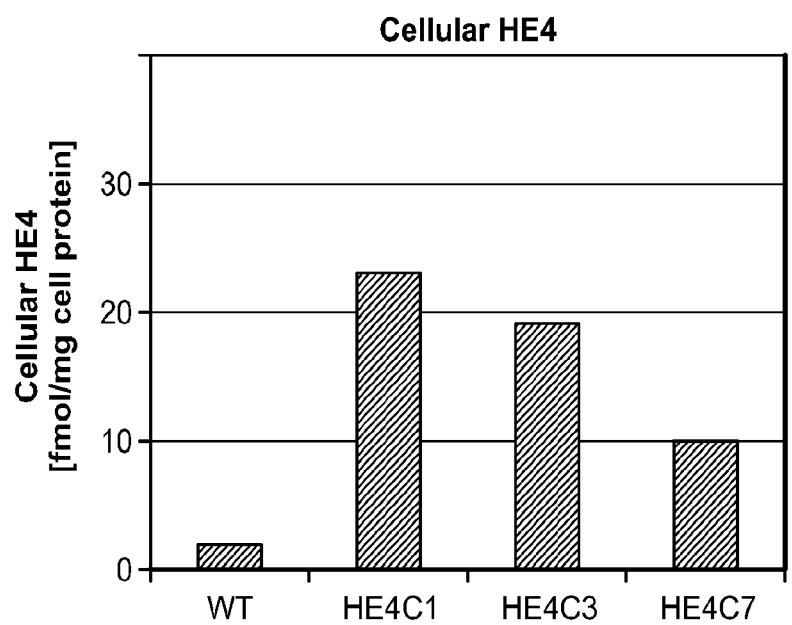
Figure 17E:
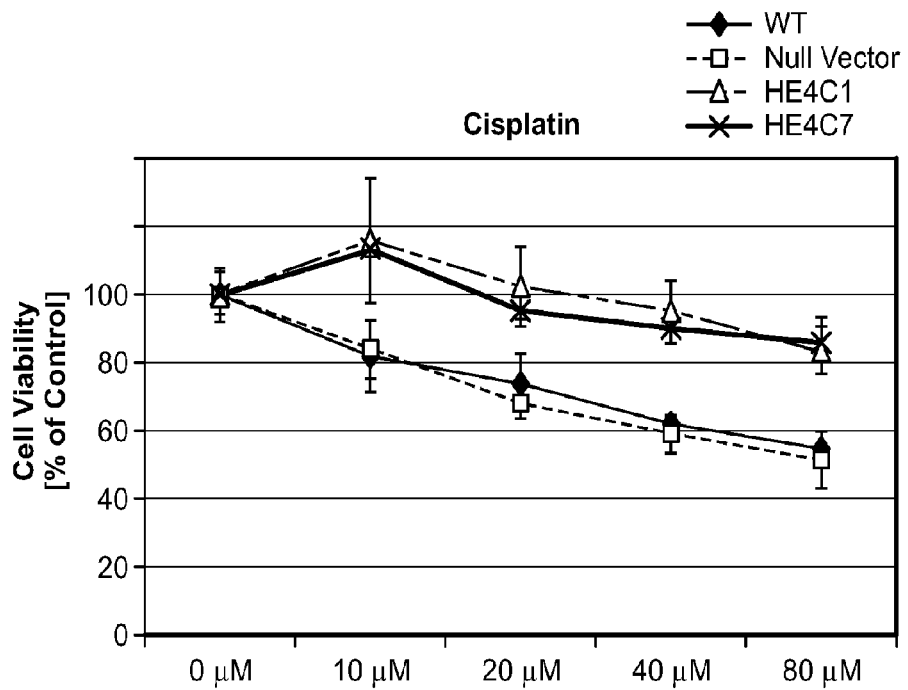
Figure 17F:
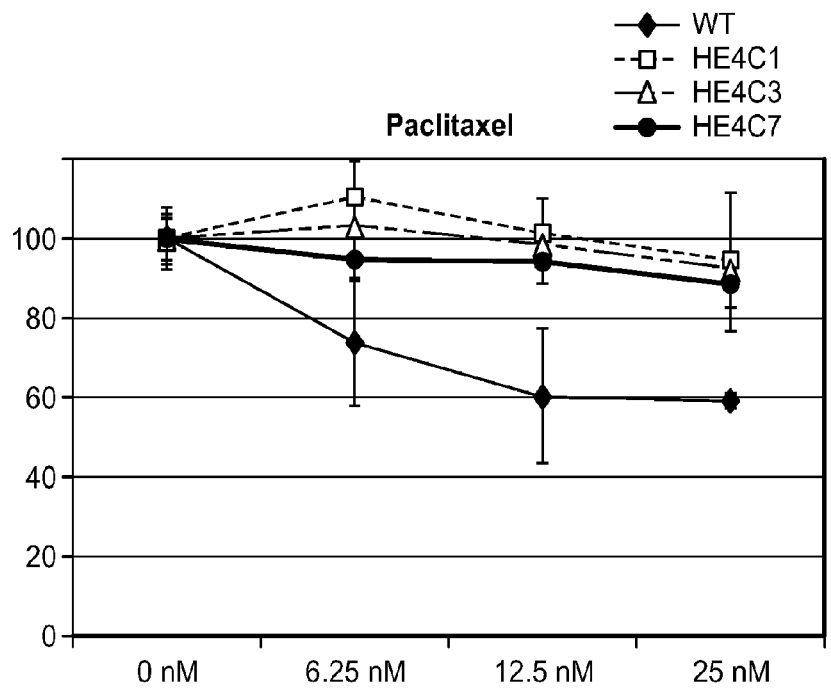

FIG. 15 is a bar chart showing that treatment with growth factors and cytokines affect the HE4 levels in ovarian cancer cells. SKOV-3 cells (1 million each) were seeded in 100 mm dishes and incubated overnight. The cells were treated with an array of factors (IL-6, Insulin, TNFa, EGF) and incubated for another 6 hours. The media was collected and cells were lysed using the cell lysis buffer. The HE4 content in the media or in the cell-lysate was examined by a HE4 sandwich ELISA kit. As shown in FIG. 15, the treatment with growth factors (Insulin and EGF) elevate HE4 levels while treatment with TNFa does not alter HE4 levels but a treatment with IL-6 suppresses the HE4 levels in ovarian cancer cells.

EXAMPLE 4

The Functional Impact of HE4 Overexpression Endometrial Cancer

Endometrial cancer refers to several types of malignancies that arise from the endometrium, or lining, of the uterus. Endometrial cancers are one of the most common gynecologic cancers in the United States, with over 35,000 women diagnosed each year. The most common subtype, endometrioid adenocarcinoma, typically occurs within a few decades of menopause, is associated with excessive estrogen exposure, often develops in the setting of endometrial hyperplasia, and presents most often with vaginal bleeding. Endometrial carcinoma is the third most common cause of gynecologic cancer death (behind ovarian and cervical cancer). A total abdominal hysterectomy (surgical removal of the uterus) with bilateral salpingo-oophorectomy is the most common therapeutic approach. Thus, there is a pressing need for new therapies for endometrial cancer.

As shown in FIG. 1, HE4 is present in the cell supernatant and cell lysate of ECC-1 cells, an endometrial cancer cell line, demonstrating that these cells produce ECC-1. Moreover, as shown in FIG. 9C, overexpression of HE4 suppressed the proliferation of ECC-1 cells.

EXAMPLE 5

Characterization of HE4 Overexpression Induced Chemoresistance and Identification of Small Molecules Targeting HE4 Overexpressing Epithelial Ovarian Cancer (EOC) Cells The biomarker HE4 (WFDC2) is highly overexpressed in epithelial ovarian cancer (EOC). Serum HE4 levels are a sensitive marker for differentiating malignant pelvic masses from benign neoplasms. The FDA cleared HE4 as a biomarker and a ROMA algorithm for monitoring EOC patients undergoing treatment and for recurrence of disease. Prior to the invention described herein, the biological mechanism of HE4 overexpression in ovarian cancer development, chemoresistance, and overall survival (OS) rate or disease free survival (DSF) rate was unknown.

Described in detail below are experiments that delineate the biological functions of HE4 and its role in EOC pathogenesis and chemoresistance. Also described is the identification of small molecules targeting HE4 overexpressing ovarian cancer cells to optimize chemotherapy in epithelial ovarian cancer patients.

A panel of stable HE4 overexpressing ovarian cancer SKOV-3 cell lines were developed by incorporation of pCMV6-HE4 vector. Inducible HE4 overexpression was achieved by pTet-Off vector (VP 16 vector). The cell viability was measured by MTS assay. Basal reactive oxygen species (ROS) production were measured by FACS analysis. In vitro Phosphoinositide-3-kinase (PI-3K) activity was measured by an immuno-precipitation PIP-3 assay. An Inductively Coupled Plasma-Mass spectrometry (IPC-MS) analysis was carried out to estimate Cisplatin binding to DNA in cells. Mitochondria, rough ER and myelin figures were examined by Electron microscopy (EM). The screening of in-house library of compounds was carried out by MTS assay.

Figure 18A:
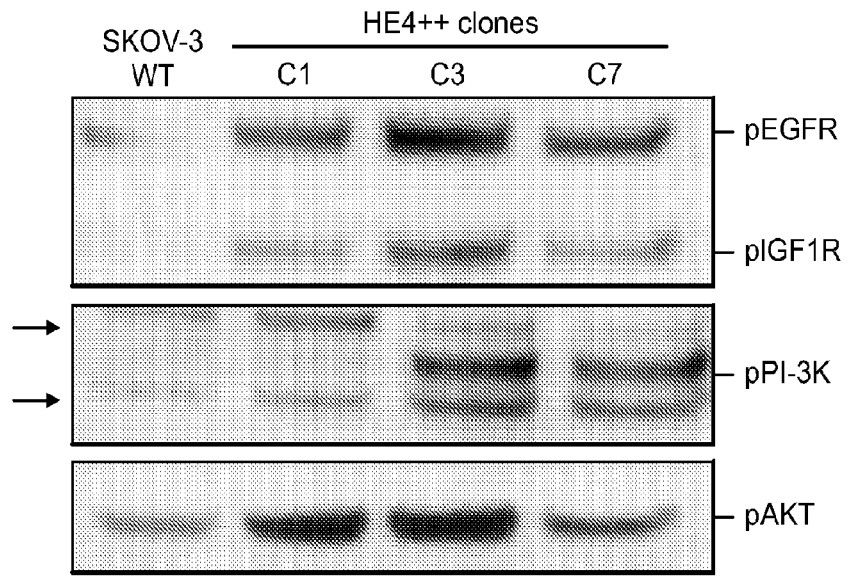
FIG. 18 is a series of photographs and a schematic illustrating that HE4 regulates EGFR/PI-3K signaling in ovarian cancer cells. (A): HE4 overexpressing clones (1, 3 and 7) showed elevated activation of oncogenic EGFR, PI-3K, AKT activation compared to parental SKOV-3 cells. (B) An in vitro immunoprecipitation lipid kinase assay shows that HE4 overexpressing clones produce up to 1.6 fold higher amount of phosphoinositidyl-3,4,5-triphosphate (PIP-3) and Cisplatin treatment resulted in further enhancement of PIP-3 synthesis. (C) Mechanistic model of HE4 overexpression induced chemoresistance against Cisplatin via activation of EGFR and PI-3K and its signaling product PIP-3.
Figure 18B:
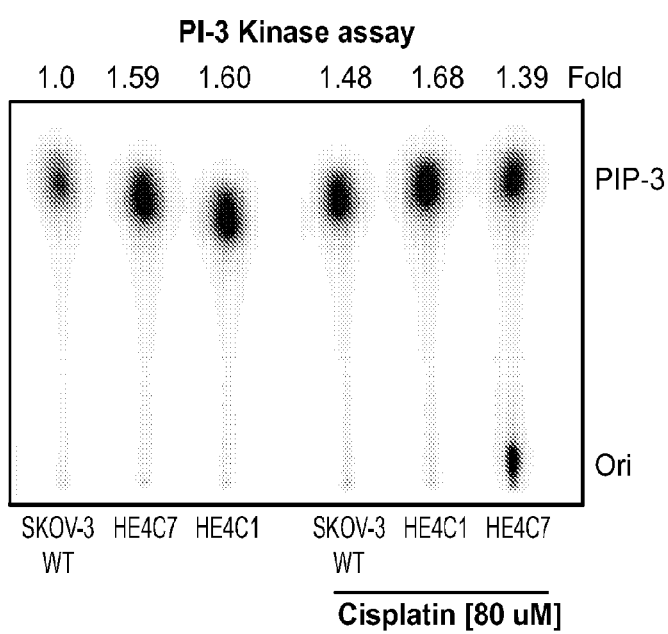
Figure 18C:
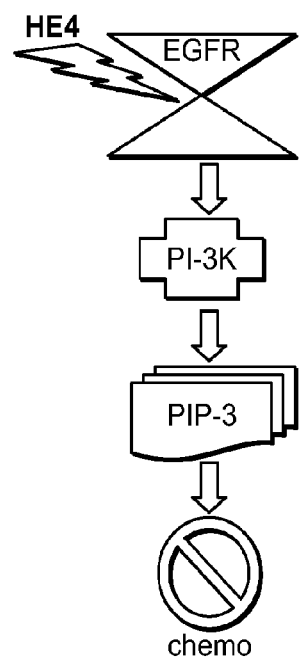
Figure 19A:
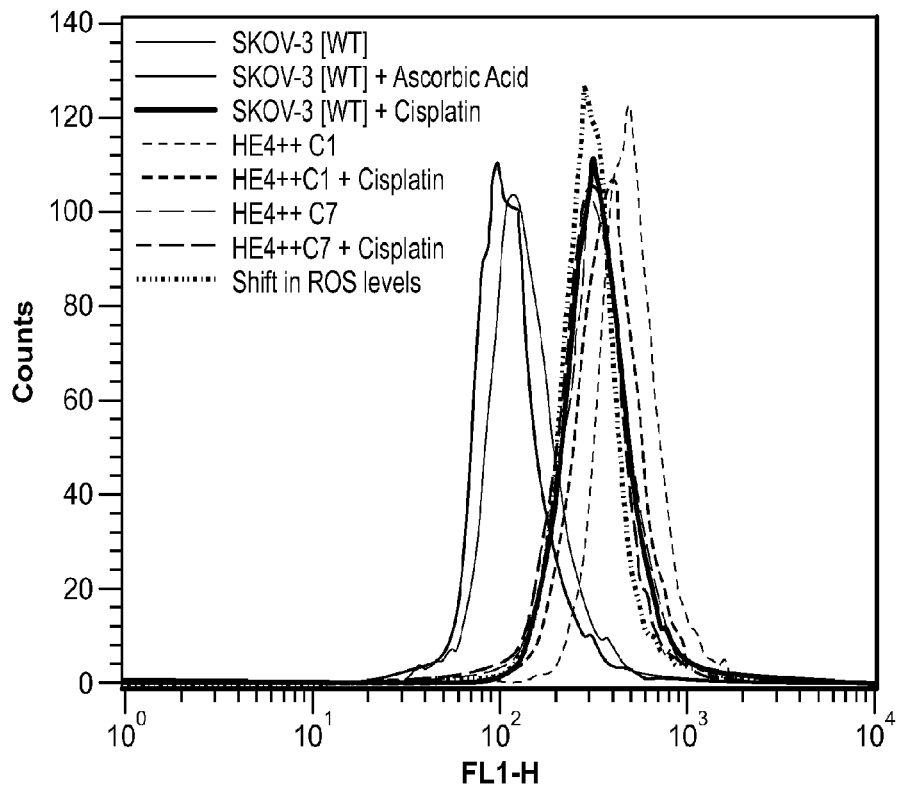
FIG. 19 is a series of line graphs demonstrating that HE4 regulates ROS levels in ovarian cancer cells. (A) HE4++ cells showed elevated ROS production. (B): RNAi of HE4 reduced ROS production in HE4 overexpressing ovarian cancer cells.
Figure 19B:
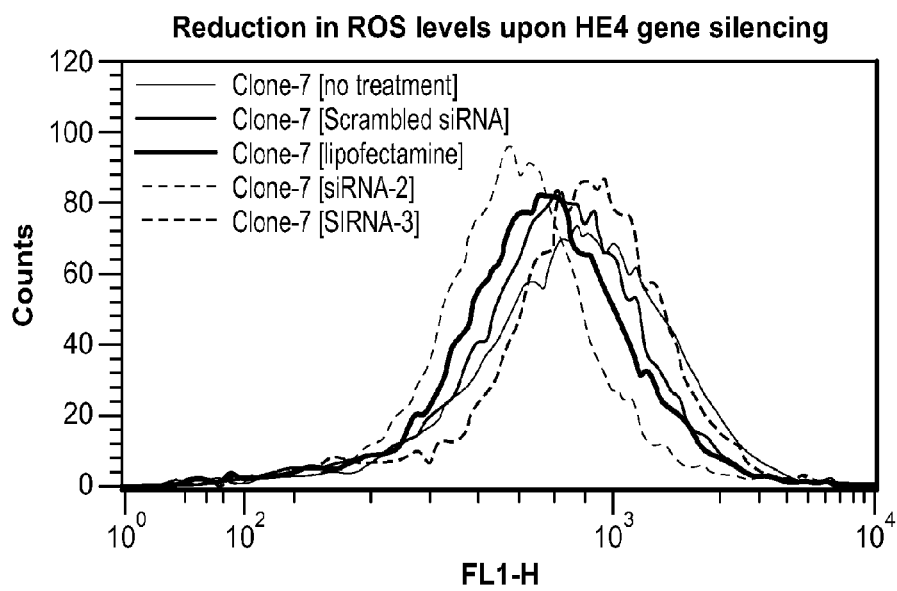
Figure 20A:
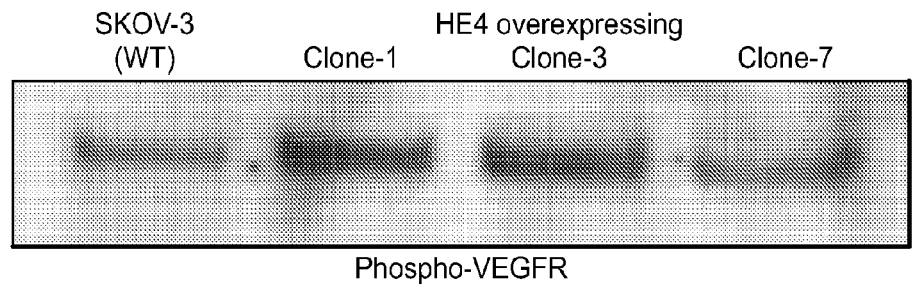
FIG. 20 is a series of photographs showing that HE4 promotes angiogenesis. (A) HE4++ cells showed elevated ROS production. (B): RNAi of HE4 reduced ROS production in HE4 overexpressing ovarian cancer cells.
Figure 20B:
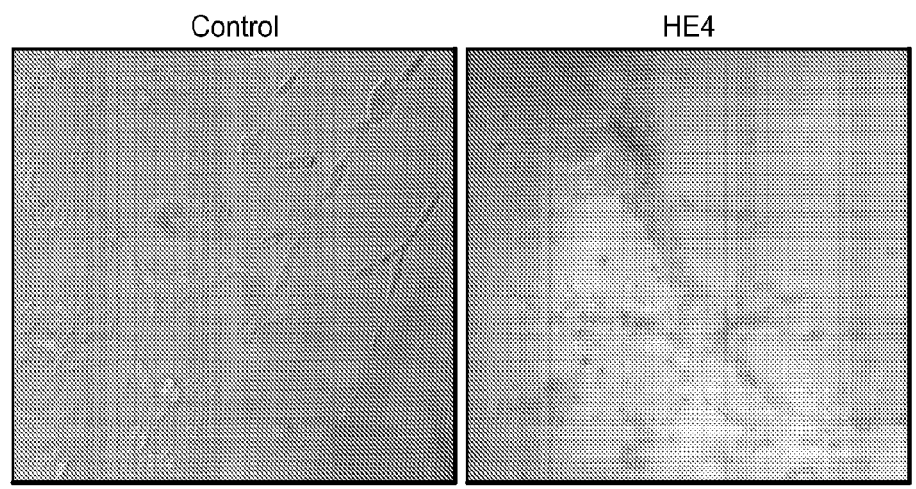
Figure 21:
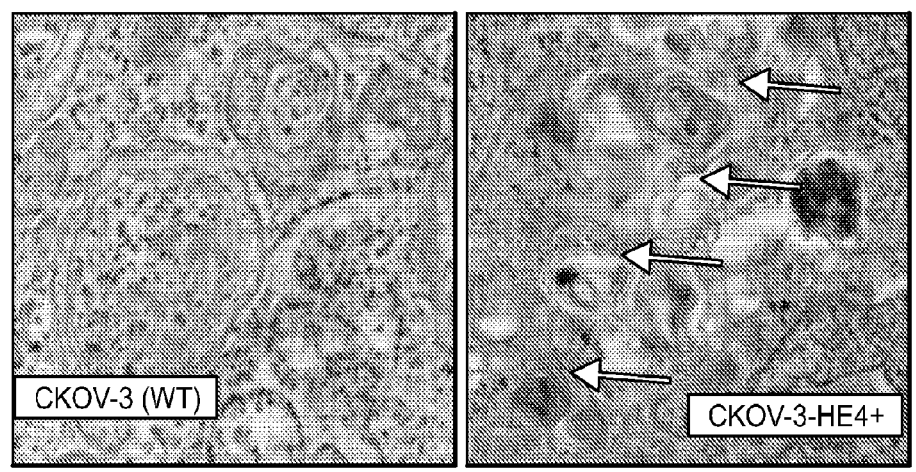
FIG. 21 is a photograph showing that HE4 overexpressing cells (right) showed abundance of myelin Figures (phospholipids and lipoproteins) compared to wild type (left). The myelin figures were possibly disorganized by gluteraldehyde (EM, 18000×).
Figure 22:
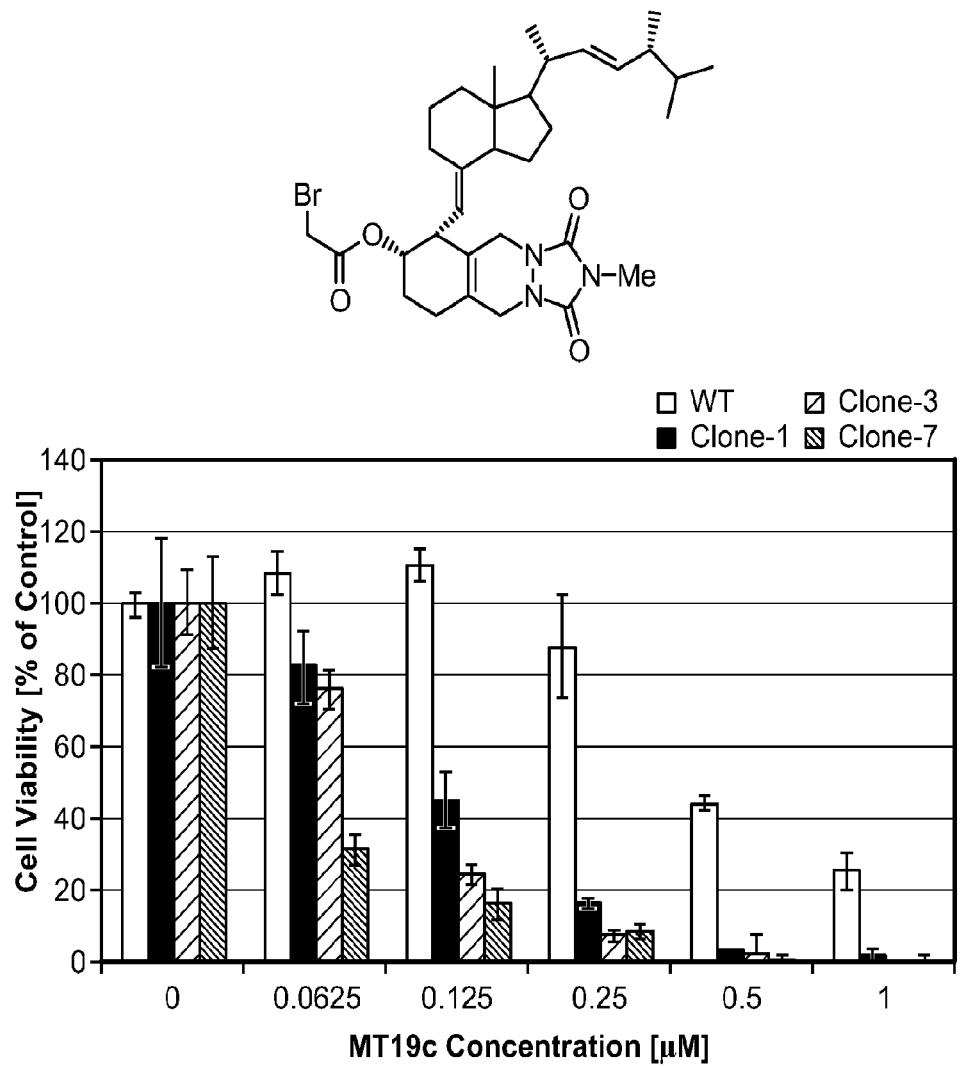
FIG. 22 is a schematic and a bar graph illustrating that MT19c is a lead molecule that targets HE4 overexpressing ovarian cancer cells. Specifically.

As described in FIG. 17, HE4 overexpressing clones (HE4+) showed reduced efficacy response against Paclitaxel, Cisplatin, Doxorubicin and Camptothecin. HE4+ clones displayed an aggressive phenotype with elevated basal reactive oxygen species (ROS) production and showed resistance towards Cisplatin-induced ROS production (FIG. 19). Silencing of the HE4 gene indicated that HE4 regulates ROS production. HE4+ clones demonstrated activation of EGFR/PI-3K including PIP-3 production and Fatty Acid synthesis in SKOV-3 cells (FIG. 18). An Inductively Coupled Plasma-Mass spectrometry (IPC-MS) analysis of HE4+ clones showed reduced Cisplatin binding to DNA than parental SKOV-3 cells. The results described herein also show that HE4 promotes angiogenesis (FIG. 20). As shown in FIG. 21, HE4 overexpressing cells show an abundance of phospholipids and lipoproteins (myelin figures). Screening of in-house library of anticancer small molecules identified MT19c as potential lead molecule targeting HE4 overexpressing ovarian cancer cells (FIG. 22).

Taken together, HE4 overexpression promotes chemoresistance against Cisplatin and Paclitaxel in EOC. Specifically, as described herein, HE4 overexpression confers strong chemoresistance against Cisplatin, Taxol and Doxorubicin mediated by an exacerbated oncogenic EGFR/PI-3K/FAS pathway. HE4 induced chemoresistance in EOC is mediated by exacerbated EGFR/PI-3K signaling. HE4 directly regulates ROS production in ovarian cancer cells. Thus, MT19c is a small molecule that can target HE4 expressing epithelial ovarian cancer cells. Additionally, selective antisense nucleotides (AONs), neutralizing antibodies, and small molecule inhibitors/modulators of the HE4 gene also target HE4 expression.

EXAMPLE 6

HE4 Overexpression Enhanced Chemoresistance Against Cisplatin In Vitro

Figure 23A:
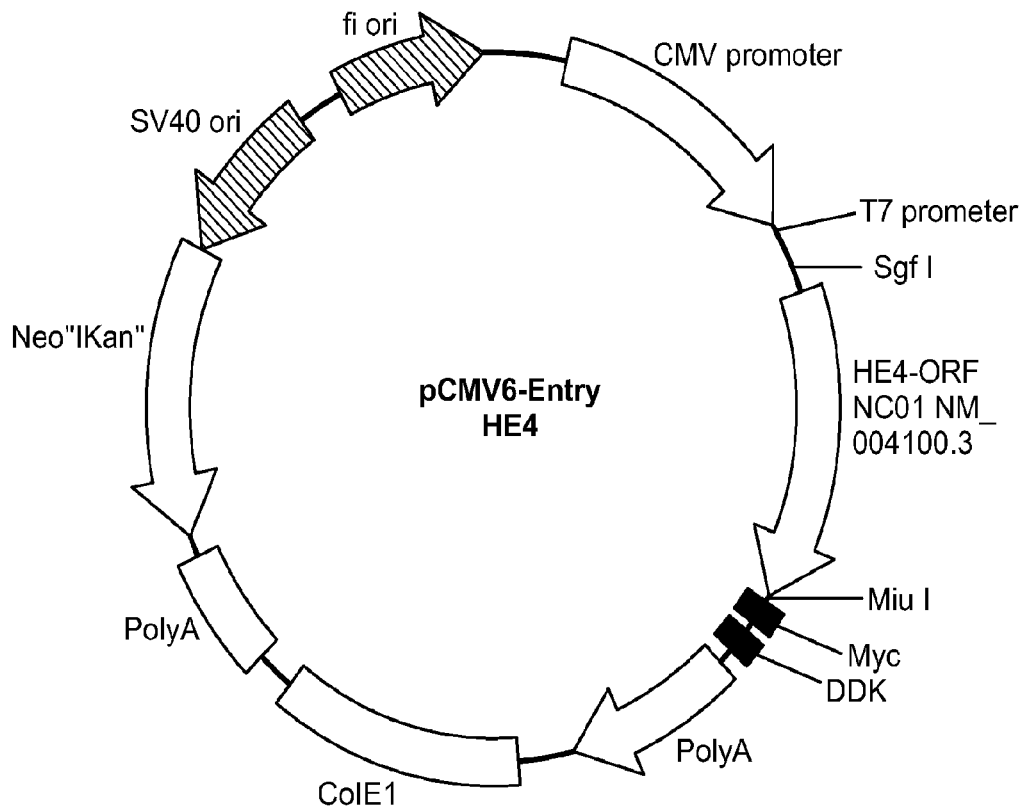
FIG. 23A is plasmid map showing a panel of HE4 overexpressing SKOV-3 cell clones stably transfected with pCMV6-HE4.
Figure 23B:
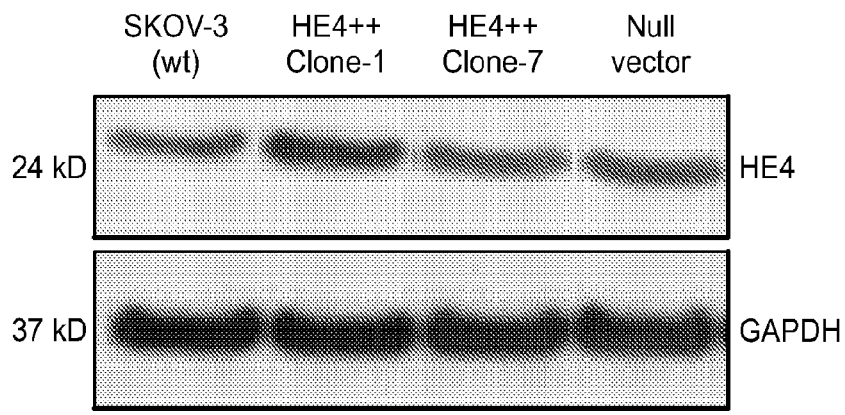
FIG. 23B is a photomicrograph of a western blot analysis showing the differential levels of HE4 protein expression.
Figure 23C:
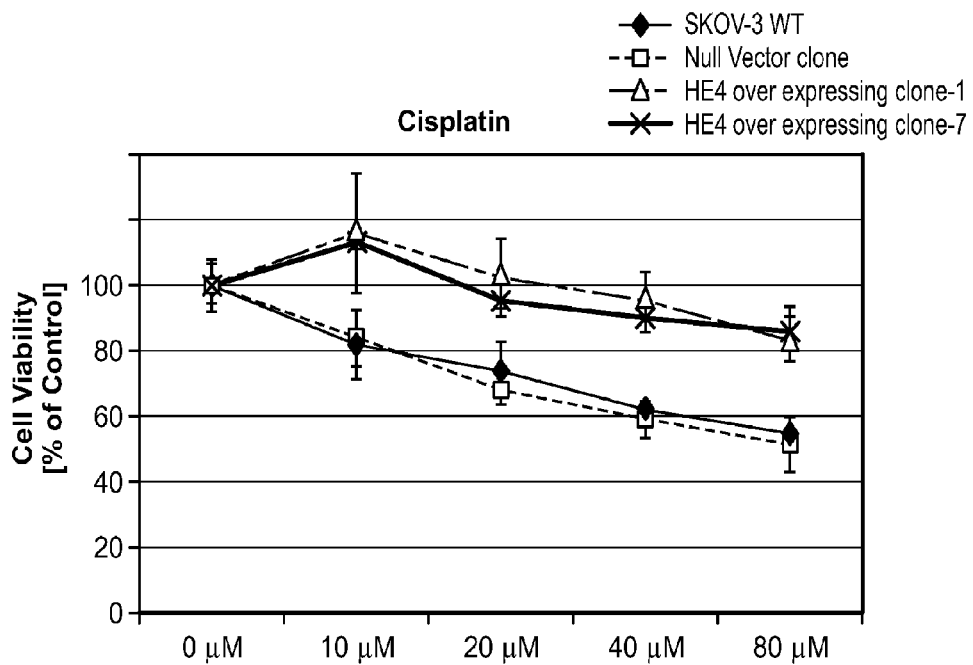
FIG. 23C is a line graph showing that the HE4 overexpressing SKOV-3 clones showed significantly reduced response to cisplatin treatment compared to parental SKOV-3 or empty construct ovarian cancer cell clones.

A panel of HE4 overexpressing SKOV-3 cell clones stably transfected with pCMV6-HE 4 was developed as shown in FIG. 23A. The differential HE4 expression was validated by western blot (FIG. 23B), PCR, and EIA/ELISA. Stable HE4 overexpressing SKOV-3 cell clones (HE4C1) showed >2-4 fold chemoresistance against cisplatin compared to the parental and ovarian cancer cells stably transfected with null vector.

HE4 Overexpression Enhanced the Tumor Burden in Ovarian Cancer Xenograft Animal Models.

Figure 24:
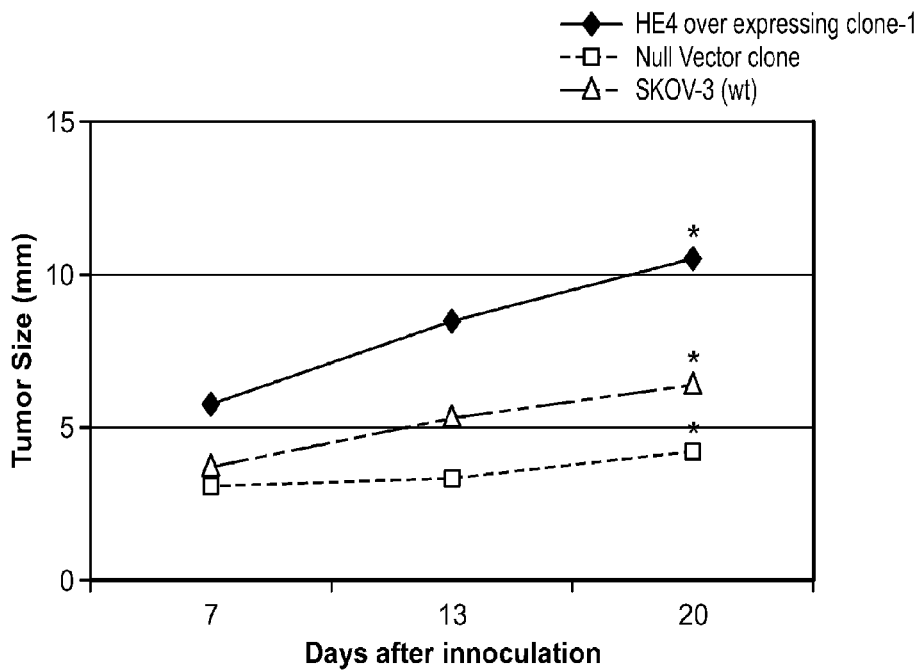
FIG. 24 is a line graph showing the evaluation of relative tumor burden in animals due to HE4 overexpression. HE4 overexpressing clones (blue) formed most progressive xenograft tumor compared to parental wild type ovarian cancer cells (SKOV-3) (green) and null vector clones (red). The pairwise group differences (Turkey-adjusted p values) showed statistical significance among the groups.

To ascertain the role of HE4 in the progression of ovarian cancer, the xenografts of stable HE4 overexpressing (pCMV6-HE4) clones, SKOV-3 (wild type) and the null vector clones (pCMV6) cells were raised in nude mice (strain 088, Nu/Nu). The tumor size was measured weekly. The data showed that HE4 overexpression generated the most progressive tumors in mice as compared to null vector clones and parental SKOV-3 cells (FIG. 24).

HE4 Overexpressing Clones Secreted Higher HE4 Protein Levels in Animals, and Cisplatin Treatment had Animal Specific Changes in HE4 Levels.

Figures 25, 26:
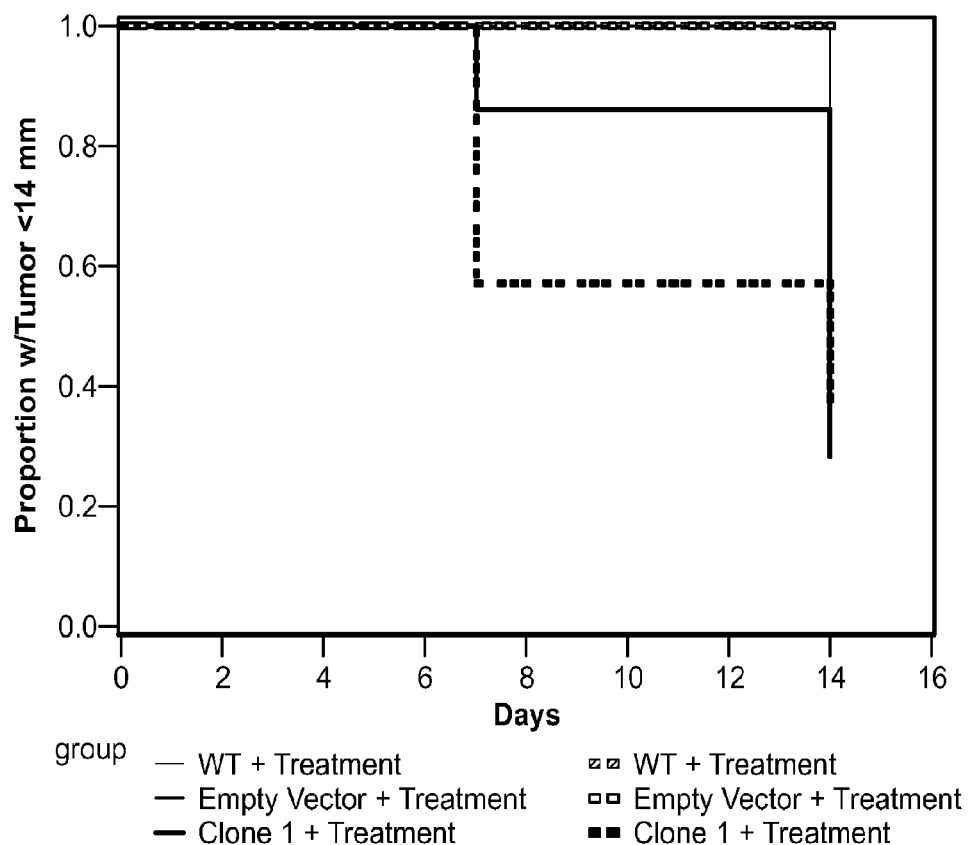
FIG. 25 is a table showing secretion levels of HE4 in animals xenografted with HE4 overexpressing clones compared to parental SKOV-3 and null vector clones. Cisplatin treatment caused animal specific change in HE4 levels. However, HE4 levels in cisplatin (5 mg/kg bwt) treated groups were not significantly different from the vehicle treated animals.
FIG. 26 is a graph showing a Kaplan-Meier analysis of survival of HE4 overexpressing clones versus parental ovarian cancer SKOV-3 cells and null vector clones treated with vehicle or cisplatin. The Kaplan-Meier analysis showed that HE4 overexpression conferred strong chemoresistance against cisplatin.
Figure 27A:
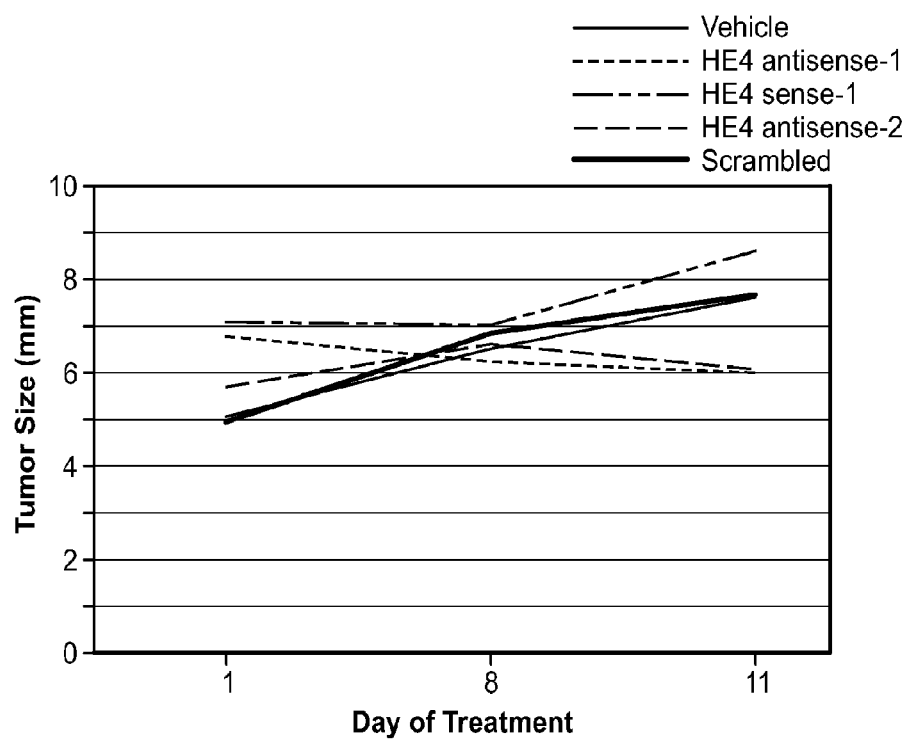
FIGS. 27A-27B is a series of line graphs showing that antisense HE4 oligos suppressed the progression of ovarian tumor growth in animals and did not cause any toxicity in animals. Left: Effect of treatment of antisense HE4 oligos ("HE4 antisense 1" corresponds to SEQ ID NO:2 and "HE4 antisense 2" corresponds to SEQ ID NO:4; red and violet, respectively), sense HE4 oligos (green), vehicle, and scrambled sequences (7 mg/kg bwt, IP) 5 days/week on the tumor size in animals xenografted with ovarian cancer (SKOV-3) cells. Right: the weight of the animals treated with oligos progressed as the day progressed, and no toxicity was observed.
Figure 27B:
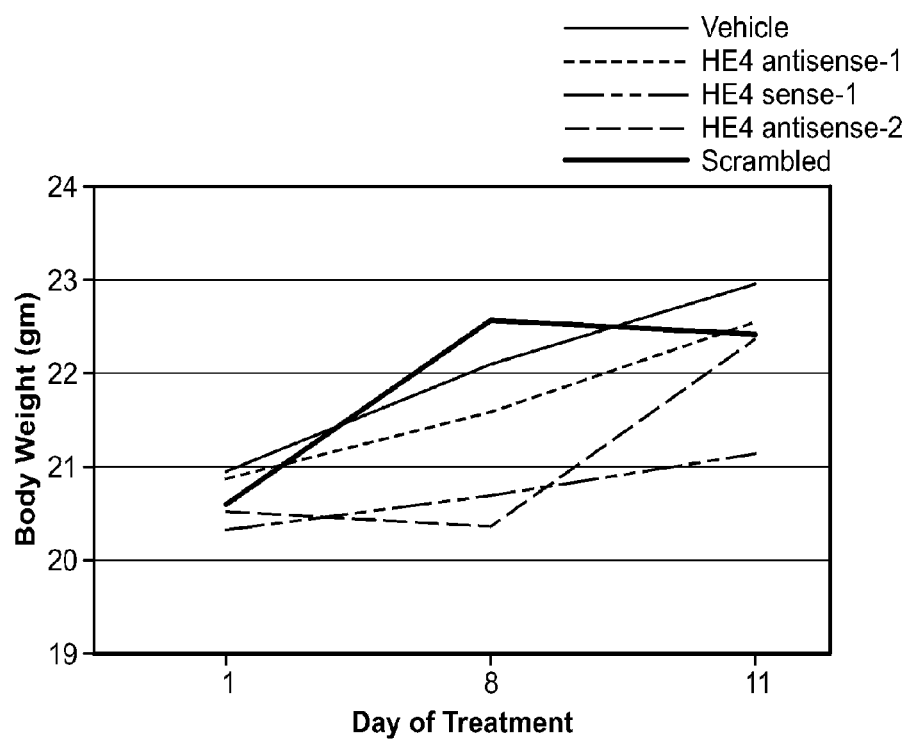
Figure 28:
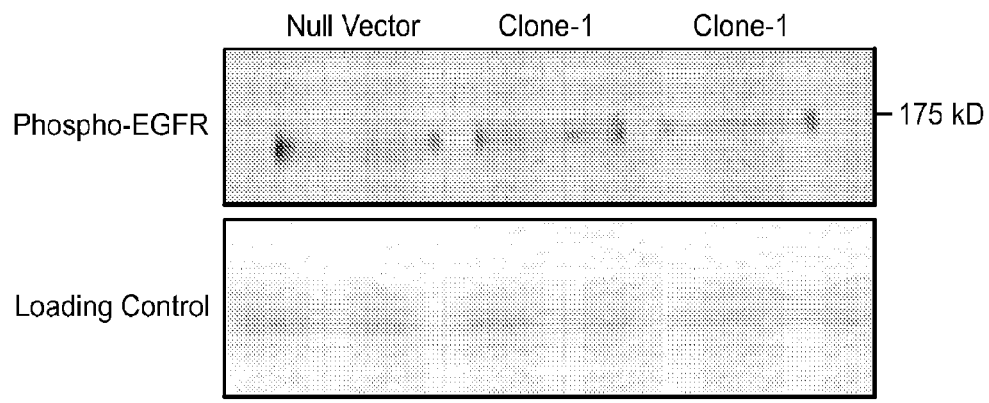
FIG. 28 is a photograph of a immunoblot showing the co-immunoprecipitation of HE4 with activated EGFR in HE4 overexpressing ovarian cancer clone and xenograft tissues harvested from animals.
Figure 29:
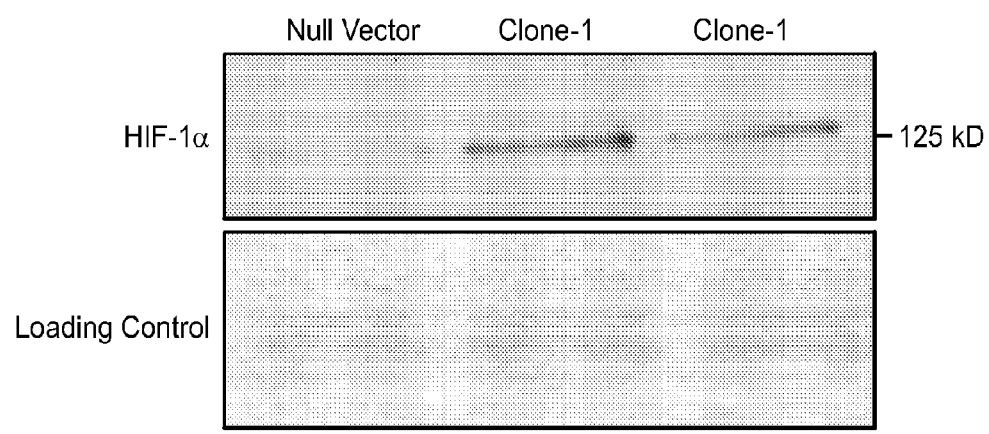
FIG. 29 is a photograph showing the co-immunoprecipitation of HE4 with hypoxia-inducible factor 1α (HIF1α) in HE4 overexpressing ovarian cancer clone and null vector xenograft tissues harvested from animals. HE4 overexpressing clones showed significantly higher interaction with HIF1α than null vector clones.

Because HE4 is a secretory protein, the secretion levels of HE4 were measured in animals by an EIA ELISA (Fujirebio Inc). HE4 overexpressing clones showed significantly higher levels of HE4 secretion in nude mice (FIG. 25). Further, groupwise, HE4 levels in cisplatin (5 mg/kg bwt) treated groups did not differ significantly from the vehicle-treated animal group; however, animal specific elevations or reductions in HE4 levels due to cisplatin was observed.

HE4 Overexpression Reduced Survival of Animals and Promoted Chemoresistance Against Cisplatin.

The survival rate, tumor size, and the cisplatin or vehicle treatment response of animals xenografted with HE4 overexpressing clone-1, parental SKOV-3, and null vector clones was determined. The Kaplan-Meier analysis of the animals showed that animals xenografted with parental ovarian cancer (SKOV-3) or null vector (pCMV6) clones did not reach the tumor size 14 mm within 14 days of observation (FIG. 26). On the other hand, ~60% animals xenografted with HE4 overexpressing clones that received cisplatin reached terminal tumor size (≥14 mm), opposed to ~85% of vehicle treated HE4 overexpressing clone xenografted animals that did not reach terminal tumor size within 14 days. Therefore, HE4 overexpression imparted chemoresistance against cisplatin treatment in animals.

Antisense Inhibition of HE4 Reduced the Tumor Burden in Platinum Resistant Ovarian Cancer Xenografted Animals.

HE4 overexpression promoted ovarian cancer burden in animals (FIG. 24), and caused strong chemoresistance against cisplatin in animals (FIG. 26). Thus, a set of antisense oligos were designed to knockdown the expression levels of HE4 in animals xenografted with ovarian cancer (SKOV-3) cells. Treatment at 5 days/week with antisense HE4 phosphorothio oligos suppressed the tumor progression in animals compared to scrambled or sense HE4 oligos and vehicle treated control within 28 days of the treatment.

The sequence of novel HE4 modulating phosphorothio oligos is set forth below:

```
                                           (SEQ ID NO: 1)
5' G*A*C*A*C*C*T*T*C*C*C*A*C*A*G*C*C*A*T*T 3'

(SEQ ID NO: 2)
5' G*A*C*A*C*C*T*T*C*C*C*A*C*A*G*C*C*A*T*T*G 3'

(SEQ ID NO: 3)
5' G*A*C*A*C*C*T*T*C*C*C*A*C*A*G*C*C*A*T 3'

(SEQ ID NO: 4)
5' A*C*A*C*C*T*T*C*C*C*A*C*A*G*C*C*A*T*T*G 3'

(SEQ ID NO: 5)
5' A*C*A*C*C*T*T*C*C*C*A*C*A*G*C*C*A*T*T 3'
```

Oligonucleotide with the sequence of SEQ ID NO:4 demonstrated a strong reduction in tumor burden in two different phenotypes of ovarian cancer, followed by the oligonucleotide with the sequence of SEQ ID NO:2. Oligos with the sequences of SEQ ID NO:1, 3, and 5 also showed tumor inhibitory activity.

HE4 Co-immunoprecipitated with Activated Epidermal Growth Factor Receptor (Phospho-EGFR) in Both SKOV-3 Xenograft and Cultured HE4 Overexpressing Clones.

Prior to the invention described herein, the molecular function of HE4 in ovarian cancer was unknown. As described herein, secreted HE4 interacts with membrane bound receptor tyrosine kinase (e.g., EGFR). A co-immunoprecipitation of HE4 with activated form of EGFR (phospho EGFR) in xenograft tumor tissues was performed and null vector was used as control. HE4 co-immunoprecipitated with phospho-EGFR in both cultured HE4 overexpressing ovarian cancer cells and xenograft tumor tissues, suggesting that HE4 may interact with receptor tyrosine kinases to activate epidermal growth factor receptor (EGFR). Activated epidermal growth factor (EGFR) contributes to ovarian cancer progression and chemoresistance against cisplatin via activation of phosphotidyl-inositol-3kinase (PI-3K) and AKT.

HE4 Co-immunoprecipitated with HIF1α in HE4 Overexpressing Clones. HE4 is Highly Secreted by Ovarian Cancer Cells.

As described herein, HE4 interacts with HIF1α in the tumor microenvironment to contribute to ovarian cancer progression. A co-immunoprecipitation of HE4 with HIF1α in HE4 overexpressing xenograft tumor tissues was performed and null vector was used as control. HE4 co-immunoprecipitated with HIF1α selectively in HE4 overexpressing tumor tissues indicating that HE4 interacts with HIF1α protein complex. HIF1α contributes to ovarian cancer progression and chemoresistance against cisplatin via enhanced angiogenesis and metabolic reprogramming to support the survival of solid tumor.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof,

What is claimed is:

1. A method of suppressing chemoresistant ovarian tumor cell growth in a subject comprising:
   identifying a subject with at least one HE4-expressing chemoresistant ovarian tumor cell; and
   modulating the level of human epididymal secretory protein E4 (HE4) in said tumor cell by administering an HE4 inhibitor to said tumor cell, wherein said inhibitor is an antisense macromolecule, MT19c, or PT19c,
   thereby suppressing chemoresistant ovarian tumor cell growth in said subject.

2. The method of claim 1, wherein said chemoresistant ovarian tumor cell is a malignant tumor cell.

3. The method of claim 1, wherein said chemoresistant ovarian tumor cell is a cancer progenitor cell or a cancer stem cell.

4. The method of claim 1, wherein said antisense macromolecule is an oligonucleotide selected from the group consisting of SEQ ID NO: 2 and SEQ ID NO: 4.

5. The method of claim 1, further comprising administering a chemotherapeutic agent selected from the group consisting of an alkylating agent, an antimetabolite, an anthracycline, an antitumor antibiotic, a monoclonal antibody, a platinum agent, a plant alkaloid, a topoisomerase inhibitor, a vinca alkaloid, a taxane, and an epipodophyllotoxin.

6. The method of claim 1, further comprising administering a chemotherapeutic agent selected from the group consisting of cisplatin, carboplatin, paclitaxel, docetaxel, doxorubicin, camptothecin, and etoposide.

7. The method of claim 1, further comprising administering a TP53 gene under the control of an HE4 promoter to said tumor cell.

8. A method of suppressing chemoresistant ovarian tumor cell growth in a subject comprising:
   diagnosing said subject with an HE4-expressing chemoresistant ovarian tumor; and
   modulating the level of HE4 in or on said chemoresistant ovarian tumor in said subject by administering an HE4 inhibitor to said tumor cell, wherein said inhibitor is an antisense macromolecule, MT19c, or PT19c,
   thereby suppressing chemoresistant ovarian tumor cell growth in said subject.

9. A method of suppressing chemoresistant ovarian tumor cell growth in a subject comprising:
   identifying a subject that has been diagnosed with an HE4-expressing chemoresistant ovarian tumor; and
   modulating the level of HE4 in or on said chemoresistant ovarian tumor in said subject by administering an HE4 inhibitor to said tumor cell, wherein said inhibitor is an antisense macromolecule, MT19c, or PT19c,
   thereby suppressing chemoresistant ovarian tumor cell growth in said subject.

10. The method of claim 8, wherein the level of HE4 is detected via a western blot.

11. The method of claim 8, wherein the level of HE4 is detected via an immunoassay kit or a fluorescent antibody.

12. The method of claim 1, wherein said antisense macromolecule is selected from the group consisting of SEQ ID NO:1, SEQ ID NO:2, SEQ ID NO:3, SEQ ID NO:4, and SEQ ID NO:5.

13. The method of claim 8, wherein said HE4 inhibitor is selected from the group consisting of SEQ ID NO:1, SEQ ID NO:2, SEQ ID NO:3, SEQ ID NO:4, and SEQ ID NO:5.

14. The method of claim 9, wherein said HE4 inhibitor is selected from the group consisting of SEQ ID NO:1, SEQ ID NO:2, SEQ NO:3, SEQ ID NO:4, and SEQ ID NO:5.

15. The method of claim 1, wherein the chemoresistance in the ovarian tumor cell is mediated by HE4.

16. The method of claim 1, wherein the chemoresistant ovarian tumor cell comprises higher constitutive activation of one or more of Epidermal Growth Factor Receptor (EGFR), Insulin-like Growth Factor Receptor (IGF1R), Phosphoinositide-3kinase (PI-3K)/AKT, or Bcl2 family oncogenes compared to parental ovarian cancer cells.

17. The method of claim 1, wherein the chemoresistant ovarian tumor cell resistant to one or more of cisplatin, taxane, doxorubicin or camptothecin.

18. The method of claim 17, further comprising administering cisplatin to the subject.

19. The method of claim 17, further comprising administering a taxane to the subject.

20. The method of claim 17, further comprising administering doxorubicin to the subject.

21. The method of claim 17, further comprising administering camptothecin to the subject.

22. The method of claim 8, wherein the chemoresistance in the ovarian tumor cell is mediated by HE4.

23. The method of claim 8, wherein the chemoresistant ovarian tumor cell comprises higher constitutive activation of one or more of Epidermal Growth Factor Receptor (EGFR), Insulin-like Growth Factor Receptor (IGF1R), Phosphoinositide-3kinase (PI-3K)/AKT, or Bcl2 family oncogenes compared to parental ovarian cancer cells.

24. The method of claim 8, wherein the chemoresistant ovarian tumor cell resistant to one or more of cisplatin, taxane, doxorubicin or camptothecin.

25. The method of claim 24, further comprising administering cisplatin to the subject.

26. The method of claim 24, further comprising administering a taxane to the subject.

27. The method of claim 24, further comprising administering doxorubicin to the subject.

28. The method of claim 24, further comprising administering camptothecin to the subject.

\* \* \* \* \*